United States Patent
Moore et al.

(10) Patent No.: US 7,157,467 B2
(45) Date of Patent: Jan. 2, 2007

(54) THERAPEUTIC USE

(75) Inventors: Nelly Corine Moore, Macclesfield (GB); Keith Oldham, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/496,464

(22) PCT Filed: Nov. 20, 2002

(86) PCT No.: PCT/GB02/05217

§ 371 (c)(1),
(2), (4) Date: May 24, 2004

(87) PCT Pub. No.: WO03/045364

PCT Pub. Date: Jun. 5, 2003

(65) Prior Publication Data

US 2005/0014773 A1     Jan. 20, 2005

(30) Foreign Application Priority Data

Nov. 23, 2001 (GB) ................................ 0128109.6

(51) Int. Cl.
*A61K 31/517* (2006.01)
*A61P 29/00* (2006.01)
*C07D 401/00* (2006.01)
*C07D 239/72* (2006.01)

(52) U.S. Cl. .............. 514/266.24; 514/266.2; 514/266.4; 544/284; 544/293

(58) Field of Classification Search ........... 514/266.24, 514/266.2, 266.4; 544/284, 293
See application file for complete search history.

(56) References Cited

U.S. PATENT DOCUMENTS 6,046,206 A * 4/2000 Pamukcu et al. ...... 514/266.21

FOREIGN PATENT DOCUMENTS

| EP | 1 052 254 A | 11/2000 |
|----|-------------|---------|
| WO | 98/13354 A  | 4/1998  |
| WO | 00/47212 A  | 8/2000  |
| WO | 02/16352 A  | 2/2002  |

OTHER PUBLICATIONS

Tobe, M., et al., "Structure-activity relationships of quinazoline derivatives: dual-acting compounds with inhibitory activities toward both TNF-alpha production and T Cell proliferation", Bioorganic & Medicinal Chemistry Letters, vol. 11, No. 4, Feb. 26, 2001, pp. 545-548, XP004230055, ISSN: 0960-894X.

Myers, et al., "The preapration and SAR of 4-(anilino), 4-(phenoxy), and 4-(thiophenoxy)-quinazolines: inhibitors of p56 and EGF-R tyrosine kinase activity", Bioorganic & Medicinal Chemistry Letters, vol. 7, No. 4, Feb. 18, 1997, pp. 417-420, XP004136037, ISSN: 0960-894X.

* cited by examiner

*Primary Examiner*—James O. Wilson
*Assistant Examiner*—Tamthom N. Truong
(74) *Attorney, Agent, or Firm*—Morgan Lewis & Bockius LLP

(57) ABSTRACT

The invention concerns the use of the quinazoline derivatives of Formula (I) Wherein each of m, $R_1$, n, $R_2$ and $R_3$ have any of the meanings defined in the description in the manufacture of a medicament for use in the prevention or treatment of T cell mediated diseases or medical conditions such as autoimmune diseases like transplant rejection or rheumatoid arthritis in a warm-blooded animal.

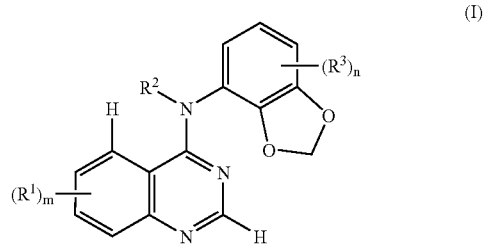

8 Claims, No Drawings

THERAPEUTIC USE

This invention concerns a new therapeutic use of certain quinazoline derivatives, or pharmaceutically-acceptable salts thereof. The compounds have been found to possess pharmacological properties of use in the treatment of autoimmune diseases or medical conditions, for example T cell mediated disease such as transplant rejection or rheumatoid arthritis.

A critical requirement of the immune system is the ability to differentiate between "self" and "non-self" (i.e. foreign) antigens. This discrimination is required to enable the immune system to mount a response to foreign proteins such as those on the surface of pathogens whilst maintaining tolerance to endogenous proteins and thereby preventing damage to normal tissues. An autoimmune disease results when self-tolerance breaks down and the immune system reacts against tissues such as the joints in rheumatoid arthritis or nerve fibres in multiple sclerosis. Stimulation of the human immune response is dependent on the recognition of protein antigens by T cells. However T cells do not become activated by and respond to antigen alone but are only triggered into action when the antigen is complexed with major histocompatibility complex (MHC) molecules on the surface of an antigen-presenting cell such as a B cell, macrophage or dendritic cell. Thus T cell activation requires the docking into the T cell receptor of the peptide/MHC complex expressed on an antigen-presenting cell. This interaction, which confers the antigen specificity to the T cell response, is essential for full activation of T lymphocytes. Subsequent to this docking, some of the earliest signal transduction events leading to full T cell activation are mediated through the action of multiple tyrosine-specific protein kinases (E. Hsi et al., *J. Biol. Chem.*, 1989, 264, 10836) including $p56^{lck}$ and ZAP-70. The tyrosine kinase $p56^{lck}$ is a lymphocyte specific member of the src family of non-receptor protein tyrosine kinases (J. D. Marth et al, *Cell*, 1985, 43, 393). The enzyme is associated with the inner surface of the plasma membrane where it binds to the T cell receptor associated glycoproteins CD4 (in helper T cells) and CD8 (in cytotoxic or killer T cells) (C. E. Rudd et al, *Proc. Natl. Acad. Sci. USA*, 1988, 85, 5190 and M. A. Campbell et al., *EMBO J.* 1990, 9, 2125).

It is believed that $p56^{lck}$ tyrosine kinase plays an essential role in T cell activation as, for example, the loss of $p56^{lck}$ expression in a human Jurkat T cell line prevents the normal T cell response to stimulation of the T cell receptor (D. B. Straus et al., *Cell*, 1992, 70, 585) and a deficiency in $p56^{lck}$ expression causes severe immune deficiency in humans (F. D. Goldman et al., *J. Clin. Invest.*, 1998, 102, 421).

Certain autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes are believed to be associated with inappropriate T cell activation (see, for example, J. H. Hanke et al., *Inflamm. Res.*, 1995, 44, 357). In addition the acute rejection of transplanted organs can also be interpreted as a consequence of inappropriate T cell activation. Therefore, compounds which modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase, are expected to provide therapeutic agents for such pathological conditions.

Without wishing to imply that the compounds disclosed in the present invention possess pharmacological activity only by virtue of an effect on a single biological process, it is believed that the compounds modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase.

In particular, the quinazoline derivatives disclosed in the invention are expected to be useful as immunoregulation or immunosuppressive agents for the prevention or treatment of organ rejection following transplant surgery.

Agents of this kind would offer therapy for transplant rejection and autoimmune diseases whilst avoiding toxicities associated with the commonly used, less selective immunosuppressants. The leading agent for the prevention or treatment of transplant rejection is cyclosporin A which, although effective, is often associated with side-effects such as renal damage and hypertension which results in kidney failure in a substantial number of patients. It is contemporary practice to treat rheumatoid arthritis initially with symptom relief agents such as NSAIDs, which do not have any beneficial effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

As stated above, the present invention is based, in particular, on the discovery that the quinazoline derivatives disclosed in the invention modulate T cell activation by way of inhibition of one or more of the multiple tyrosine-specific protein kinases which are involved in the early signal transduction steps which lead to full T cell activation. Accordingly compounds disclosed in the present invention possess higher inhibitory potency against particular non-receptor tyrosine kinases such as $p56^{lck}$ tyrosine kinase than against other non-receptor tyrosine kinases or against receptor tyrosine kinases (RTKs) such as epidermal growth factor (EGF) RTK and/or VEGF RTK. In general, the quinazoline derivatives disclosed in the invention possess sufficient potency in inhibiting non-receptor tyrosine kinases such as $p56^{lck}$ tyrosine kinase that they may be used in an amount sufficient to inhibit, for example, $p56^{lck}$ tyrosine kinase whilst demonstrating reduced potency, preferably whilst demonstrating no significant activity, against RTKs such as EGF RTK or VEGF RTK. Thus the quinazoline derivatives disclosed in the invention can be used in the clinical management of those particular diseases which are sensitive to inhibition of such non-receptor tyrosine kinases, for example autoimmune diseases or medical conditions, for example T cell mediated disease such as transplant rejection or rheumatoid arthritis.

According to one aspect of the invention there is provided the use of a quinazoline derivative of the Formula I

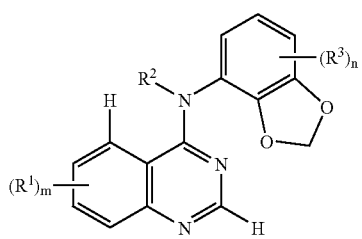

wherein m is 0, 1, 2 or 3;

each R¹ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^1$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a R¹ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl or, when the inserted group is $N(R^5)$, $R^5$ may also be (2–6C)alkanoyl, and wherein any $CH_2$=CH— or HC≡C— group within a R¹ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a R¹ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on R¹ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)allyl, or from a group of the formula:

—$X^5$-$Q^4$ wherein $X^5$ is a direct bond or is selected from O, $N(R^{10})$ and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on R¹ optionally bears 1 or 2 oxo or thioxo substituents;

R² is hydrogen or (1–6C)alkyl;

n is 0, 1, 2 or 3; and

R³ is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-

[(1–6C)alkyl]sulphamoyl, (1–6C)alkanesulphonylamino and N-(1–6C)alkyl-(1–6C)alkanesulphonylamino, or from a group of the formula:

wherein $X^6$ is a direct bond or is selected from O and $N(R^{12})$, wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

wherein $X^7$ is a direct bond or is selected from O, S, SO, $SO_2$, $N(R^{13})$, CO, $CH(OR^{13})$, $CON(R^{13})$, $N(R^{13})CO$; $SO_2N(R^{13})$, $N(R^{13})SO_2$, $C(R^{13})_2O$, $C(R^{13})_2S$ and $N(R^{13})C(R^{13})_2$, wherein $R^{13}$ is hydrogen or (1–6C)alkyl, and $Q^5$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which maybe the same or different, selected from halogeno, (1–6C)alkyl, (2–8C)alkenyl, (2–8C)alkynyl and (1–6C)alkoxy, and any heterocyclyl group within $Q^5$ optionally bears 1 or 2 oxo or thioxo substituents, or a pharmaceutically-acceptable salt thereof;

in the manufacture of a medicament for use in the prevention or treatment of T cell mediated diseases or medical conditions in a warm-blooded animal such as man.

We have found that the compounds disclosed in the present invention are of use in the prevention or treatment of autoimmune diseases or medical conditions, for example T cell mediated disease such as transplant rejection, rheumatoid arthritis or multiple sclerosis. We have further found that these effects are believed to arise by virtue of inhibition of one or more of the multiple tyrosine-specific protein kinases which are involved in the early signal transduction steps which lead to full T cell activation, for example by way of inhibition of the enzyme $p56^{lck}$. Accordingly the compounds disclosed in the present invention are expected to be useful in the prevention or treatment of T cell mediated diseases or medical conditions. In particular the compounds disclosed in the present invention are expected to be useful in the prevention or treatment of those pathological conditions which are sensitive to inhibition of one or more of the multiple tyrosine-specific protein kinases which are involved in the early signal transduction steps which lead to T cell activation, for example by way of inhibition of $p56^{lck}$ tyrosine kinase. Further, the compounds disclosed in the present invention are expected to be useful in the prevention or treatment of those diseases or medical conditions which are mediated alone or in part by inhibition of the enzyme $p56^{lck}$, i.e. the compounds may be used to produce a $p56^{lck}$ enzyme inhibitory effect in a warm-blooded animal in need of such treatment. Specifically, the compounds disclosed in the present invention are expected to be useful in the prevention or treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds disclosed in the present invention are expected to be useful in the prevention or treatment of the acute rejection of transplanted tissue or organs.

According to a further feature of this aspect of the invention there is provided a method for the prevention or treatment of T cell mediated diseases or medical conditions in a warm-blooded animal, such as man, in need of such treatment which comprises administering to said animal an effective amount of a quinazoline derivative of the Formula I, or a pharmaceutically-acceptable salt thereof, as defined hereinbefore.

According to a further feature of the invention there is provided the use of a quinazoline derivative of the Formula L or a pharmaceutically-acceptable salt thereof, as defined immediately hereinbefore in the manufacture of a medicament for use in the prevention or treatment of those pathological conditions which are sensitive to inhibition of one or more of the multiple tyrosine-specific protein kinases which are involved in the early signal transduction steps which lead to T cell activation.

According to a further feature of the invention there is provided a method for the prevention or treatment of those pathological conditions which are sensitive to inhibition of one or more of the multiple tyrosine-specific protein kinases which are involved in the early signal transduction steps which lead to T cell activation which comprises administering to said animal an effective amount of a quinazoline derivative of the Formula I, or a pharmaceutically-acceptable salt thereof as defined immediately hereinbefore.

In this specification the generic term "alkyl" includes both straight-chain and branched-chain alkyl groups such as propyl, isopropyl and tert-butyl, and also (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6-Calkyl]amino includes dimethylamino, diethylamino. N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^5$) when it is aryl or for the aryl group within a 'Q' group is, for example, phenyl or naphthyl, preferably phenyl.

A suitable value for any one of the 'Q' groups ($Q^1$ or $Q^3$) when it is (3–7C)cycloalkyl or for the (3–7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$ or $Q^3$) when it is (3–7C)cycloalkenyl or for the (3–7C)cycloalkenyl group within a 'Q' group is, for example, cyclobutenyl cyclopentenyl cyclohexenyl or cycloheptenyl.

A suitable value for any one of the 'Q' groups ($Q^1$ to $Q^5$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^5$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

In structural Formula I there is a hydrogen atom at each of the 2- and 5-positions on the quinazoline ring. It is to be understood thereby that the $R^1$ substituents may only be located at the 6-, 7- or 8-positions on the quinazoline ring i.e. that the 2- and 5-positions remain unsubstituted. It is further to be understood that the $R^3$ group that may be present on the 2,3-methylenedioxyphenyl group within structural Formula I maybe located on the phenyl ring or on the methylene group within the 2,3-methylenedioxy group. Preferably, any $R^3$ group that is present on the 2,3-methylenedioxyphenyl group within structural Formula I is located on the phenyl ring thereof.

Suitable values for any of the 'R' groups ($R^1$ to $R^{13}$) or for various groups within an $R^1$ or $R^3$ substituent include:
for halogeno fluoro, chloro, bromo and iodo;
for (1–6C)alkyl: methyl, ethyl, propyl, isopropyl and tert-butyl;
for (2–8C)alkenyl: vinyl, isopropenyl, allyl and but-2-enyl;
for (2–8C)alkynyl: ethynyl, 2-propynyl and but-2-ynyl;
for (1–6C)alkoxy: methoxy, ethoxy, propoxy, isopropoxy and butoxy;
for (2–6C)alkenyloxy: vinyloxy and allyloxy;
for (2–6C)alkynyloxy: ethynyloxy and 2-propynyloxy;
for (1–6C)alkylthio: methylthio, ethylthio and propylthio;

for (1–6C)alkylsulphinyl: methylsulphinyl and ethylsulphinyl;
for (1–6C)alkylsulphonyl: methylsulphonyl and ethylsulphonyl;
for (1–6C)alkylamino: methylamino, ethylamino, propylamino, isopropylamino and butylamino;
for di-[(1–6C)alkyl]amino: dimethylamino, diethylamino, N-ethyl-N-methylamino and diisopropylamino;
for (1–6C)alkoxycarbonyl: methoxycarbonyl, ethoxycarbonyl, propoxycarbonyl and tert-butoxycarbonyl;
for N-(1–6C)alkylcarbamoyl: N-methylcarbamoyl, N-ethylcarbamoyl and N-propylcarbamoyl;
for N,N-di-[(1–6C)alkyl]carbamoyl: N,N-dimethylcarbamoyl, N-ethyl-N-methylcarbamoyl and N,N-diethylcarbamoyl;
for (2–6C)alkanoyl: acetyl and propionyl;
for (2–6C)alkanoyloxy: acetoxy and propionyloxy;
for (2–6C)alkanoylamino: acetamido and propionamido;
for N-(1–6C)alkyl-(2–6C)alkanoylamino: N-methylacetamido and N-methylpropionamido;
for N-(1–6C)alkylsulphamoyl: N-methylsulphamoyl and N-ethylsulphamoyl;
for N,N-di-[(1–6C)alkyl]sulphamoyl: N,N-dimethylsulphamoyl;
for (1–6C)alkanesulphonylamino: methanesulphonylamino and ethanesulphonylamino;
for N-(1–6C)alkyl-(1–6C)alkanesulphonylamino: N-methylmethanesulphonylamino and N-methylethanesulphonylamino;
for (3–6C)alkenoylamino: acrylamido, methacrylamido and crotonamido;
for N-(1–6C)alkyl-(3–6C)alkenoylamino: N-methylacrylamido and N-methylcrotonamido;
for (3–6C)alkynoylamino: propiolamido;
for N-(1–6C)alkyl-(3–6C)alkynoylamino: N-methylpropiolamido;
for amino(1–6C)alkyl: aminomethyl, 2-aminoethyl, 1-aminoethyl and 3-aminopropyl;
for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;
for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;
for halogeno-(1–6C)alkyl: chloromethyl, 2-chloroethyl, 1-chloroethyl and 3-chloropropyl;
for hydroxy-(1–6C)alkyl: hydroxymethyl, 2-hydroxyethyl, 1-hydroxyethyl and 3-hydroxypropyl;
for (1–6C)alkoxy-(1–6C)alkyl: methoxymethyl, ethoxymethyl, 1-methoxyethyl, 2-methoxyethyl, 2-ethoxyethyl and 3-methoxypropyl;
for cyano-(1–6C)alkyl: cyanomethyl, 2-cyanoethyl, 1-cyanoethyl and 3-cyanopropyl;
for (2–6C)alkanoylamino-(1–6C)alkyl: acetamidomethyl, propionamidomethyl and 2-acetamidoethyl; and
for (1–6C)alkoxycarbonylamino-(1–6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^1$ group. Similarly, when, for example a $CH_3$ group within a $R^1$ substituent bears a group of the formula —$X^3$-$Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q_2$-$X^2$— and —$X^7$-$Q^5$.

As defined hereinbefore, adjacent carbon atoms in any (2–6C)alkylene chain within a $R^1$ substituent may be optionally separated by the insertion into the chain of a group such as O, CON($R^5$) or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^2$-$X^2$— wherein $X^2$ is, for example, NHCO and $Q^2$ is a heterocyclyl-(1–6C)alkyl group, suitable $R^1$ substituents so formed include, for example, N-[heterocyclyl-(1–6C)alkyl]carbamoylvinyl groups such as N-(2-pyrrolidin-1-ylethyl)carbamoylvinyl or N-[heterocyclyl-(1–6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno or (1–6C)alkyl substituents, there are suitably 1 or 2 halogeno or (1–6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1–6C)alkoxy groups such as 2-hydroxy-3-piperidinopropoxy and 2-hydroxy-3-morpholinopropoxy, hydroxy-substituted amino-(2–6C)alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C)alkylamino-(2–6C)alkylamino groups such as 2-hydroxy-3-methylaminopropylamino, hydroxy-substituted di-[(1–6C)alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy, (1–6C)alkylsulphonyl-substituted (1–6C)alkoxy groups such as 2-methylsulphonylethoxy and heterocyclyl-substituted (1–6C)alkylamino-(1–6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular compounds defined in the invention include, for example, quinazoline derivatives of the Formula I, or pharmaceutically-acceptable salts thereof, wherein, unless otherwise stated, each of m, $R^1$, $R^2$, n and $R^3$ has any of the meanings defined hereinbefore or in paragraphs (a) to (k) hereinafter:

(a) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$$Q^1\text{-}X^1\text{—}$$

wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, or, when the inserted group is N($R^5$), $R^5$ may also be (2–6C)alkanoyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^2\text{-}X^2\text{—}$$

wherein $X^2$ is a direct bond or is CO or N($R^6$)CO, wherein $R^6$ is hydrogen or (1–6C)alkyl, and $Q^2$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino and N-(1–6C)alkyl-(2–6C)alkanoylamino, or from a group of the formula:

$$\text{—}X^3\text{-}Q^3$$

wherein $X^3$ is a direct bond or is selected from O, N($R^6$), CON($R^7$), N($R^7$)CO and C($R^7$)$_2$O, wherein $R^7$ is hydrogen or (1–6C)alkyl, and $Q^3$ is heteroaryl, heteroaryl-(1–6C) alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is hydroxy-(1–6C)alkyl, (1–6C)alkoxy-(1–6C)alkyl, cyano(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—$X^5$-$Q^4$ wherein $X^5$ is a direct bond or is selected from O, N($R^{10}$) and CO, wherein $R^{10}$ is hydrogen or (1–6C)alkyl, and $Q^4$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;
(b) m is 1 or 2, and each $R^1$ group, which may be the same or different, is selected from fluoro, chloro, trifluoromethyl, hydroxy, amino, carbamoyl, methyl, ethyl, propyl, butyl, vinyl, ethynyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^1$-$X^1$— wherein $X^1$ is a direct bond or is selected from O, NH, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl 2-(1,1-dioxotetrahydro-4H-1,4-thiazin-4-yl)ethyl, 3-(1,1-dioxotetrahydro-4H-1,4-thiazinyl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any CH$_2$=CH— or HC≡C— group within a $R^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^2$-$X^2$— wherein $X^2$ is a direct bond or is CO, NHCO or N(Me)CO and $Q^2$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

—$X^3$-$Q^3$ wherein $X^3$ is a direct bond or is selected from O, NH, CONH, NHCO and CH$_2$O and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-yl-methyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, methoxy, N-methylcarbamoyl and N,N-diethylcarbamoyl, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(c) m is 1 or 2 and each $R^1$ group, which may be the same or different, is located at the 6- and/or 7-positions and is selected from hydroxy, amino, methyl, ethyl, propyl, butyl, vinyl, ethynyl, methoxy, ethoxy, propoxy, isopropoxy, butoxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyridylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazinyl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^2$-$X^2$— wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N,N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(d) m is 1 and the $R^1$ group is located at the 6- or 7-position and is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, benzyloxy, 2-imidazol-1-ylethoxy, 2-(1,2,3-triazol-1-yl)ethoxy, 2-(1,2,4-triazol-1-yl)ethoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diisopropylamino, N-ethyl-N-methylamino, N-isopropyl-N-methylamino and acetoxy, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(e) $R^2$ is hydrogen;

(f) n is 1 or 2 and the $R^3$ groups, which may be the same or different, are located at the 5- and/or 6-positions of the 2,3-methylenedioxyphenyl group and are selected from halogeno, trifluoromethyl, cyano, hydroxy, (1–6C)alkyl, (2–8C)alkenyl, (2–8C)alkynyl and (1–6C)alkoxy;

(g) n is 1 or 2 and the $R^3$ groups, which may be the same or different, are located at the 5- and/or 6-positions of the 2,3-methylenedioxyphenyl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy, (h) n is 1 and the $R^3$ group is located at the 5- or 6-position of the 2,3-methylenedioxyphenyl group, especially the 6-position, and is selected from chloro, bromo, trifluoromethyl, cyano, methyl, ethyl, methoxy and ethoxy;

(i) n is 1 and the $R^3$ group is located at the 6-position of the 2,3-methylenedioxyphenyl group and is selected from chloro, bromo and trifluoromethyl;

(j) n is 0; and (k) m is 2 and each $R^1$ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on $R^1$ optionally bears 1, 2 or 3 substituents, which may be the same or different, selected from fluoro, chloro, trifluoromethyl cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a $R^1$ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents.

A preferred compound disclosed in the invention is a quinazoline derivative of the Formula I wherein:

m is 1 or 2 and each $R^1$ group, which may be the same or different, is located at the 6- and/or 7-positions and is selected from hydroxy, amino, methyl, ethyl, propyl, butyl, ethoxy, ethoxy, propoxy, isopropoxy, butoxy, methylamino, ethylamino, dimethylamino, diethylamino, acetamido, propionamido, 2-imidazol-1-ylethoxy, 2-(1,2,4-triazol-1-yl)ethoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^2$ is hydrogen;

n is 0 or 1 and the $R^3$ group, if present, is located at the 5- or 6-position of the 2,3-methylenedioxyphenyl group and is selected from fluoro, chloro, trifluoromethyl, cyano, hydroxy, methyl, ethyl, vinyl, allyl, ethynyl, methoxy and ethoxy;

or a pharmaceutically-acceptable acid-addition salt thereof.

A further preferred compound disclosed in the invention is a quinazoline derivative of the Formula I wherein:

m is 2 and each $R^1$ group, which may be the same or different, is located at the 6- and/or 7-positions and is selected from hydroxy, amino, methyl, ethyl, methoxy, ethoxy, propoxy, isopropoxy, butoxy, methylamino, ethylamino, dimethylamino, diethylamino, acetamido, propionamido, benzyloxy, 2-pyrrol-1-ylethoxy, 3-pyrrol-1-ylpropoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, 2-pyridylmethoxy, 3-pyridylmethoxy, 4-pyridylmethoxy, 2-tetrahydropyran-4-ylethoxy, 3-tetrahydropyran-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH═CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino, dimethylamino, diethylamino, diisopropylamino, N-ethyl-N-methylamino, N-isopropyl-N-methylamino, N-isobutyl-N-methylamino, N-allyl-N-methylamino, acetoxy, acetamido, N-methylacetamido, 2-pyridyloxy, 3-pyridyloxy and 4-pyridyloxy, and wherein any phenyl, pyrrolyl, imidazolyl, triazolyl, pyridyl or heterocyclyl group within a substituent on $R^1$ optionally bears 1, 2 or 3 substituents, which may be the same or different, selected from fluoro, chloro, trifluoromethyl, cyano, hydroxy, amino, carbamoyl, methyl, ethyl, N-methylcarbamoyl, N,N-dimethylcarbamoyl, methoxy, methoxymethyl and morpholinomethyl, and a pyrrolidin-2-yl, piperidin-3-yl, piperidin-4-yl, piperazin-1-yl or homopiperazin-1-yl group within a $R^1$ substituent is optionally N-substituted with methyl, ethyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

$R^1$ is hydrogen;

n is 0 or 1 and the $R^3$ group, if present, is located at the 6-position of the 2,3-methylenedioxyphenyl group and is selected from chloro, bromo and trifluoromethyl;

or a pharmaceutically-acceptable acid-addition salt thereof.

A further preferred compound disclosed in the invention is a quinazoline derivative of the Formula I wherein:

m is 2 and the first $R^1$ group is located at the 6-position and is selected from hydroxy, methoxy, ethoxy and propoxy, and the second $R^1$ group is located at the 7-position and is selected from 24-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(N-isopropyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin 4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidinyl)propoxy, 2-(4-methylpiperazin-1-yl)ethoxy, 3-(4-methylpiperazin-1-yl)propoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-[2-(4-methylpiperazin-1-yl)ethoxy]ethoxy, 2-methylsulphonylethoxy and 3-methylsulphonylpropoxy, and wherein any $CH_2$ group within the second $R^1$ group that is attached to two carbon atoms optionally bears a hydroxy group or acetoxy group on said $CH_2$ group, and wherein any heterocyclyl group within the second $R^1$ group optionally bears 1 or 2 oxo substituents;

$R^2$ is hydrogen; and n is 0 or n is 1 and the $R^3$ group is located at the 5- or 6-position of the 2,3-methylenedioxyphenyl group and is selected from fluoro, chloro, trifluoromethyl, cyano, methyl, ethyl, ethynyl, methoxy and ethoxy, or a pharmaceutically-acceptable acid-addition salt thereof.

A further preferred compound disclosed in the invention is a quinazoline derivative of the Formula I wherein:

m is 2 and the first $R^1$ group is a 6-methoxy group and the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-isopropyl-N-methylamino)butoxy, 2-(N-isobutyl-N-methylamino)ethoxy, 3-(N-isobutyl-N-methylamino)propoxy, 4-(N-isobutyl-N-methylamino)butoxy, 2-(N-allyl-N-methylamino)ethoxy, 3-(N-allyl-N-methylamino)propoxy, 4-(N-allyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidinyloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any $CH_2$ group within the second $R^1$ group that is attached to two carbon atoms optionally bears a hydroxy group on said $CH_2$ group, and wherein any heteroaryl group within the second $R^1$ group optionally bears 1 or 2 substituents selected from chloro, cyano, hydroxy and methyl, and any heterocyclyl group within the second $R^1$ group optionally bears 1 or 2 substituents selected from hydroxy, methyl and oxo;

$R^2$ is hydrogen; and n is 0 or n is 1 and the $R^3$ group is located at the 6-position of the 2,3-methylenedioxyphenyl group and is selected from chloro and bromo;

or a pharmaceutically-acceptable acid-addition salt thereof.

A further preferred compound disclosed in the invention is a quinazoline derivative of the Formula I wherein:

m is 2 and the first $R^1$ group is a 6-methoxy group and the second $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, piperidin-4-ylmethoxy, N-methylpiperidin-3-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-N-methylpiperidin-4-yl)propoxy, 2-(4-methylpiperazin-1-yl)ethoxy, 3-(4-methylpiperazin-1-yl)propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-methylsulphonylethoxy, 3-methylsulphonylpropoxy, 2-(4-pyridyloxy)ethoxy, 3-pyridylmethoxy and 2-cyanopyrid-4-ylmethoxy;

$R^2$ is hydrogen; and n is 0 or n is 1 and the $R^3$ group is located at the 6-position of the 2,3-methylenedioxyphenyl group and is selected from chloro and bromo;

or a pharmaceutically-acceptable acid-addition salt thereof.

A further preferred compound disclosed in the invention is a quinazoline derivative of the Formula I wherein:

m is 2 and the first $R^1$ group is a 6-methoxy group and the second $R^1$ group is located at the 7-position and is selected from 3-(N-isopropyl-N-methylamino)propoxy, 3-pyrrolidin-1-ylpropoxy, 3-morpholinopropoxy, 3-(1,1-dioxotetrahydro-4H-1,4-thiazin-4-yl)propoxy, 3-piperidinopropoxy, N-methylpiperidin-4-ylmethoxy, 2-(4-methylpiperazin-1-yl)ethoxy, 3-(4-methylpiperazin-1-yl)propoxy, 3-(4-cyanomethylpiperazin-1-yl)propoxy and 2-[2-(4-methylpiperazin-1-yl)ethoxy]ethoxy, and wherein any $CH_2$ group within the second $R^1$ group that is attached to two carbon atoms optionally bears a hydroxy group on said $CH_2$ group;

$R^2$ is hydrogen; and n is 0;

or a pharmaceutically-acceptable acid-addition salt thereof.

A particular preferred compound disclosed in the invention is, for example, a quinazoline derivative of the Formula I selected from:

6-methoxy-4-(2,3-methylenedioxyanilino)-7-(3-morpholinopropoxy)quinazoline, 6-methoxy-4-(2,3-methylenedioxyanilino)-7-[3-(1,1-dioxotetrahydro-4H-1,4-thiazin-4-yl)propoxy]quinazoline, 6-methoxy-4-(2,3-methylenedioxyanilino)-7-(3-pyrrolidin-1-ylpropoxy)quinazoline, 6-methoxy-4-(2,3-methylenedioxyanilino)-7-[2-(4-methylpiperazin-1-yl)ethoxy]quinazoline, 6-methoxy-4-(2,3-methylenedioxyanilino)-7-[3-(4-methylpiperazin-1-yl)propoxy]quinazoline, 6-methoxy-4-(2,3-methylenedioxyanilino)-7-(3-piperidinopropoxy)quinazoline, 6-methoxy-4-(2,3-methylenedioxyanilino)-7-(N-methylpiperidin-4-ylmethoxy)quinazoline, 7-(2-hydroxy-3-pyrrolidin-1-ylpropoxy)-6-methoxy-4-(2,3-methylenedioxyanilino)quinazoline, 7-[2-hydroxy-3-(N-isopropyl-N-methylamino)propoxy]-6-methoxy-4-(2,3-methylenedioxyanilino)quinazoline, 7-[3-(4-cyanomethylpiperazin-1-yl)-2-hydroxypropoxy]-6-methoxy-4-(2,3-methylenedioxyanilino)quinazoline, 6-methoxy-4-(2,3-methylenedioxyanilino)-7-{2-[2-(4-methylpiperazin-1-yl)ethoxy]ethoxy}quinazoline, 4-(6-chloro-2,3-methylenedioxyanilino)-7-[3-(4-cyanomethylpiperazin-1-yl)propoxy]-6-methoxyquinazoline, 4-(6-chloro-2,3-methylenedioxyanilino)-6-methoxy-7-(3-pyrrolidin-1-ylpropoxy)quinazoline, 4-(6-chloro-2,3-methylenedioxyanilino)-6-methoxy-7-(3-piperidinopropoxy)quinazoline, 4-(6-bromo-2,3-methylenedioxyanilino)-6-methoxy-7-(3-piperidinopropoxy)quinazoline, 6-methoxy-4-(2,3-methylenedioxyanilino)-7-[2-(N-methylpiperidinyl)ethoxy]quinazoline, 6-methoxy-4-(2,3-methylenedioxyanilino)-7-[2-(4-pyridyloxy)ethoxy]quinazoline, 6-methoxy-4-(2,3-methylenedioxyanilino)-7-(3-pyridylmethoxy)quinazoline, 4-(6-chloro-2,3-methylenedioxyanilino)-7-(2-cyanopyrid-4-ylmethoxy)-6-methoxyquinazoline and 4-(6-chloro-2,3-methylenedioxyanilino)-6-methoxy-7-(N-methylpiperidin-4-ylmethoxy)quinazoline;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are illustrated by the following representative process variants in which, unless otherwise stated, m, $R^1$, $R^2$, n and $R^3$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction of a quinazoline of the Formula II

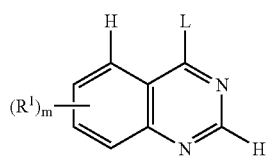

wherein L is a displaceable group and m and $R^1$ have any of the meanings defined hereinbefore except that any functional group is protected if necessary, with an aniline of the Formula III

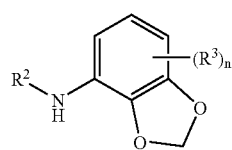

wherein $R^2$, n and $R^3$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 40 to 120° C.

Typically, the quinazoline of the Formula II may be reacted with an aniline of the Formula III in the presence of a protic solvent such as isopropanol, conveniently in the presence of an acid, for example hydrogen chloride gas in diethyl ether, and at a temperature in the range, for example, 25 to 150° C., preferably at or near the reflux temperature of the reaction solvent.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

Quinazoline starting materials of the Formula II may be obtained by conventional procedures. For example, a 3,4-dihydroquinazolin-4-one of Formula IV

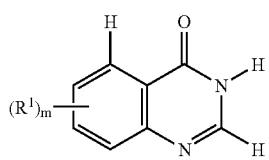

wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

2,3-Methylenedioxyaniline starting materials of the Formula III may be obtained by conventional procedures as illustrated in the Examples.

(b) For the production of those compounds of the Formula I wherein at least one $R^1$ group is a group of the formula

Q$^1$-X$^1$— wherein Q$^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)allyl group or an optionally substituted alkyl group and X$^1$ is an oxygen atom, the coupling, conveniently in the presence of a suitable dehydrating agent, of a quinazoline of the Formula V

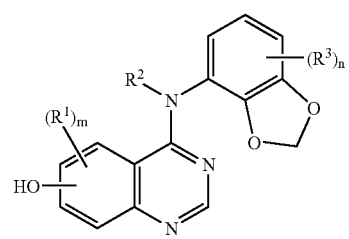

wherein m, $R^1$, $R^2$, n and $R^3$ have any of the meanings defined hereinbefore except that any functional group is protected if necessary, with an appropriate alcohol wherein any functional group is protected if necessary whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein $R^1$ is an amino-substituted (1–6C)alkoxy group (such as 2-homopiperidin-1-ylethoxy or 3-dimethylaminopropoxy), the reaction of a compound of the Formula I wherein $R^1$ is a halogeno-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(d) For the production of those compounds of the Formula I wherein $R^1$ is a hydroxy group, the cleavage of a quinazoline derivative of the Formula I wherein $R^1$ is a (1–6C)alkoxy or arylmethoxy group.

The cleavage reaction may conveniently be carried out by any of the many procedures known for such a transformation. The cleavage reaction of a compound of the Formula I wherein $R^1$ is a (1–6C)alkoxy group may be carried out, for example, by treatment of the quinazoline derivative with an alkali metal (1–6C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. The cleavage reaction of a compound of the Formula I wherein $R^1$ is a arylmethoxy group maybe carried out, for example, by hydrogenation of the quinazoline derivative in the presence of a suitable metallic catalyst such as palladium or by reaction with an organic or inorganic acid, for example trifluoroacetic acid. Such reactions are preferably carried out in the presence of a suitable inert solvent or diluent as defined hereinbefore and at a temperature in the range, for example, 10 to 150° C., preferably at or near ambient temperature.

(e) For the production of those compounds of the Formula I wherein an $R^1$ group contains a primary or secondary amino group, the cleavage of the corresponding compound of the Formula I wherein the $R^1$ group contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

(f) For the production of those compounds of the Formula I wherein an $R^1$ group contains a (1–6C)alkoxy or substituted (1–6C)alkoxy group or a (1–6C)alkylamino or substituted (1–6C)alkylamino group, the allylation, conveniently in the presence of a suitable base as defined hereinbefore, of a quinazoline derivative of the formula I wherein the $R^1$ group contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ contains a (1–6C)alkylamino or substituted (1–6C)alkylamino group, a reductive amination reaction may be employed. For example, for the production of those compounds of the Formula I wherein $R^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminum hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminum hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) For the production of those compounds of the Formula I wherein $R^1$ is an amino-hydroxy-disubstituted (1–6C)alkoxy group (such as 2-hydroxy-3-pyrrolidin-1-ylpropoxy or 3-[N-allyl-N-methylamino]-2-hydroxypropoxy), the reaction of a compound of the Formula I wherein the $R^1$ group contains an epoxy-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(h) For the production of those compounds of the Formula I wherein an $R^1$ group contains a hydroxy group, the cleavage of the corresponding compound of the Formula I wherein the $R^1$ group contains a protected hydroxy group.

Suitable protecting groups for a hydroxy group are, for example, any of the protecting groups disclosed hereinbefore. Suitable methods for the cleavage of such hydroxy protecting groups are also disclosed hereinbefore. In particular, a suitable protecting group is a lower alkanoyl group such as an acetyl group which may be cleaved under conventional reaction conditions such as under base-catalysed conditions, for example in the presence of ammonia.

When a pharmaceutically-acceptable salt of a quinazoline derivative of the Formula I is required, for example, an acid-addition salt, it may be obtained by, for example, reaction of said quinazoline derivative with a suitable acid using a conventional procedure.

Biological Assays

The following assays can be used to measure the effects of the compounds of the Formula I as $p56^{lck}$ inhibitors, as inhibitors of T cell activation, as inhibitors of cytokine production in mice and as inhibitors of transplant rejection.

(a) In Vitro Enzyme Assay

The ability of test compounds to inhibit phosphorylation by the enzyme $p56^{lck}$ of a tyrosine-containing polypeptide substrate was assessed using a conventional Elisa assay.

The following conventional procedure was used to obtain $p56^{lck}$ enzyme. An EcoR1/Not1 fragment containing the entire coding sequence of $p56^{lck}$ was generated by the technique of polymerase chain reaction (PCR) from Incyte clone No. 2829606. A 6-His tag was added to the sequence at the N-terminus during the PCR stage. Conventional sequence analysis identified a number of changes compared to the published sequence and these were found also to have been present in the original Incyte template. To achieve expression of the enzyme, the PCR fragment was inserted downstream of the polyhedrin promotor of pFASTBAC1 ([Life Technologies Limited, Paisley, UK, Catalogue No. 10360-014). A recombinant Baculovirus was constructed using the Bac-to-Bac system (Life Technologies Limited). High Five insect cells (Invitrogen BV, PO Box 2312, 9704 CH Groningen, The Netherlands, Catalogue No. B855-02) were infected with the recombinant Baculovirus at a multiplicity of infection of 1 and incubated for 48 hours. The cells were harvested. Groups of $1.6 \times 10^9$ cells were lysed by incubation in 20 mM Hepes pH7.5 buffer containing 10% glycerol, 1% Triton-X-100, magnesium chloride (1.5 mM), ethylene glycol bis(2-aminoethyl ether N,N,N',N'-tetraacetic acid) (EGTA, 1 mM), sodium vanadate (1 mM), sodium fluoride (10 mM), imidazole (5 mM), sodium chloride (150 mM), phenylmethanesulphonyl fluoride (0.1 mM), pepstatin (1 mg/ml) and leupeptin (1 mg/ml). A soluble fraction was obtained by centrifugation and 6-His-p56$^{lck}$ was purified by column chromatography on a 1 ml Ni-NTA agarose column (Qiagen Limited, Crawley, West Sussex, UK). The protein was eluted using the above-mentioned buffer except that imidazole (100 mM) was also present. The p56$^{lck}$ enzyme so obtained was stored at −80° C.

Substrate solution [100 μl of a 2 μg/ml solution of the polyamino acid Poly(Glu, Ala, Tyr) 6:3:1 (Sigma Catalogue No. P3899) in phosphate buffered saline PBS)] was added to each well of a Nunc 96-well immunoplate (Catalogue No. 439454) and the plate was sealed and stored at 4° C. for 16 hours. The excess of substrate solution was discarded, the substrate-coated wells were washed with Hepes pH7.4 buffer (50 mM, 300 μl) and blotted dry. Each test compound was dissolved in DMSO and diluted to give a series of dilutions (from 100 μM to 0.001 μM of the compound in a 10:1 mixture of water and DMSO. Portions (25 μl) of each dilution of test compound were transferred to the 96-well assay plate. Aliquots (25 μl) of a 10:1 mixture of water and DMSO were added followed by aliquots (25 μl) of a mixture of adenosine triphosphate (ATP; 24 μl of a 1 mM aqueous solution) and manganese chloride (3 ml of a 40 mM aqueous solution).

p56$^{lck}$ enzyme (0.31 μl of a 0.5 mg/ml stock solution) was diluted in a mixture of Hepes pH 7.4 buffer (200 mM, 3 ml), sodium orthovanadate (2 mM, 0.6 ml), 1% Triton X-100 (0.6 ml), dithiothreitol (25 mM, 48 μl) and distilled water (1.8 ml). Aliquots (50 μl) of the resultant solution were transferred to each well in the assay plate and the plate was incubated at ambient temperature for 8 minutes. The wells were washed sequentially with two aliquots (300 μl) of phosphate-buffered saline (PBS) containing 0.1% Tween 20 (hereinafter PBS/T).

Aliquots (100 μl) were added to each well of a mixture of antiphosphotyrosine-4G10 monoclonal IgG2bk antibody (UBI Catalogue No. 05-321; 30 μl of a 50 μg/ml solution of the antibody in PBS/T), PBS/T (11 ml) and bovine serum albumin (BSA; Sigma Catalogue No. A6793; 55 mg) and the plate was incubated at ambient temperature for 1 hour. The wells were washed sequentially with two aliquots (300 μl) of PBS/T and blotted dry. Aliquots (100 μl) were added to each well of a mixture of sheep anti-mouse IgG-peroxidase antibody (Amersham Catalogue No. NXA931; 20 μl), PBS/T (11 ml) and BSA (55 mg) and the plate was incubated at ambient temperature for 1 hour. The wells were washed sequentially with two aliquots (300 μl) of PBS/T and blotted dry.

Aliquots (100 μl) were added to each well of an ABTS solution [prepared by adding an 2,2'-azinobis(3-ethylbenzothiazolinesulphonic acid) (ABTS) tablet (50 mg; Boehringer Catalogue No. 1204521) to a mixture (50 mM) of phosphate-citrate pH5.0 buffer and 0.03% sodium perborate (obtained by adding a PCSB capsule (Sigma Catalogue No. P-4922) to distilled water (100 ml))]. The plate was incubated at ambient temperature for 1.5 hours and the absorbance at 405 nm was determined.

The extent of inhibition of the phosphorylation reaction at a range of concentrations of each test compound was determined and an IC$_{50}$ value was calculated.

(b) In Vitro T Cell Proliferation Assays

The ability of test compounds to inhibit T cell proliferation was assessed by using human peripheral blood mononuclear cells and stimulation of the T cells by way of the T cell receptor or other than by way of the T cell receptor.

Peripheral blood mononuclear cells (PBMC) were isolated from heparinised (10 units/ml heparin) human blood by density centrifugation (Lymphoprep™; Nycomed) spinning initially at 2000 rpm at ambient temperature for 20 minutes. Cells at the interphase were transferred to clean tubes, diluted 1:1 with RPMI 1640 medium (Gibco) and spun at 2000 rpm at ambient temperature for 10 minutes. The cell pellet was resuspended in RPMI 1640 medium and spun at 1400 rpm at ambient temperature for 10 minutes. The cell pellet was resuspended in RPMI 1640 medium and spun at 900 rpm at ambient temperature for 10 minutes to remove platelets. The prepared mononuclear cells were resuspended in an assay medium comprising RPMI 1640 culture medium supplemented with 50 units/ml penicillin, 50 μg/ml streptomycin, 1 mM glutamine and 10% heat-inactivated human AB serum.

Test compounds were solubilised in DMSO at a concentration of 10 mM and diluted 1:83.3 in assay medium. Aliquots (75 μl) were added to each well of a 96 well flat-bottomed tissue culture plate and subsequently serial 1 to 3 dilutions were made into assay medium giving final test concentrations in the range 0.1 to 30 μM. Control wells contained assay medium (50 μl) containing 1.2% DMSO. PBMCs (100 μl of a suspension of 2×10$^6$ cells/ml in assay medium) were added to each well and incubated for 1 hour at 37° C. in a humidified (5% CO$_2$/95% air) incubator.

The extent of inhibition of T cell proliferation at a range of concentrations of each test compound was determined and an IC$_{50}$ value was calculated.

(b)(i) T Cell Receptor Stimulation

Aliquots (50 μl) of the T cell receptor stimulatory anti-CD3 antibody (Pharmingen Catalogue No. 30100D; 40 ng/ml in assay medium) were added to each well and the cells were incubated for 24 hours at 37° C. in a humidified (5% CO$_2$/95% air) incubator. Tritiated thymidine (1 μCi per well) was added and the cells were incubated for up to a further 24 hours at 37° C. The cells were harvested onto a filter mat and radioactivity was counted using a Wallac 1450 Microbeta Plus liquid scintillation counter.

(b)(ii) Non T Cell Receptor Stimulation

Aliquots (50 μl) of a mixture of the cell stimulants PMA (phorbol-12-myristate-13-acetate, Sigma Catalogue No. P8139; 40 ng/ml) and Ionomycin (Sigma Catalogue No. I0684; 1.2 μM) were added to each well and the cells were incubated and analysed as described in paragraph (b)(i).

(c) In Vivo Skin Graft Rejection Test

The ability of test compounds to inhibit rodent skin allograft rejection was assessed using analogous procedures to those disclosed by J. Magae et al., *Cellular Immunology*, 1996, 173, 276–281 and R. Tsuji et al., *J. Antibiot.*, 1992, 45, 1295 to assess the effect of cyclosporin A on T cell properties in vivo.

(d) Test as Anti-arthritic Agent

Activity of a test compound as an anti-arthritic agent was assessed as follows. Acid soluble native type II collagen has been shown to be arthritogenic in rats causing polyarthritis when administered in Freunds incomplete adjuvant by (D. E. Trentham et al. *J. Exp. Med.*, 1977, 146, 857). This is now known as collagen-induced arthritis (CIA) and similar conditions can be induced in mice and primates. CIA in DBA/1 mice as described by R. O. Williams et al., *Proc Natl. Acad.*

*Sci.*, 1992, 89, 9784 and *Immunology* 1995, 84, 433 is a tertiary model which can be used to demonstrate the antiarthritic activity of a test compound.

Although the pharmacological properties of the compounds of the Formula I vary with structural change as expected, in general activity possessed by compounds of the Formula I may be demonstrated at the following concentrations or doses in one or more of the above tests (a), (b), (c) and (d):

Test (a):—$IC_{50}$ in the range, for example, 0.001–5 µM;
Test (b)(i):—$IC_{50}$ in the range, for example, 0.01–10 µM;
Test (b)(ii):—$IC_{50}$ in the range, for example, 0.5–>30 µM;
Test (c):—activity in the range, for example, 1–100 mg/kg;
Test (d):—activity in the range, for example, 1–100 mg/kg;

No physiologically-unacceptable toxicity was observed at the effective dose for those compounds of Formula I that were tested. Accordingly no untoward toxicological effects are expected when a compound of Formula L or a pharmaceutically-acceptable salt thereof, as defined hereinbefore is administered at the dosage ranges defined hereinafter.

A pharmaceutical composition for the compounds of the Formula I comprises a quinazoline derivative of the Formula I, or a pharmaceutically-acceptable salt thereof, as defined hereinbefore in association with a pharmaceutically-acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose is received in the range, for example, 0.1 mg/kg to 75 mg/kg body weight, conveniently 0.1 mg/kg to 30 mg/kg body weight, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I as defined hereinbefore for use in the prevention or treatment of T cell mediated diseases or medical conditions in a warm-blooded animal such as man. According to a further aspect of the invention there is provided a quinazoline derivative of the Formula I as defined hereinbefore for use in the prevention or treatment of those pathological conditions which are sensitive to inhibition of one or more of the multiple tyrosine-specific protein kinases which are involved in the early signal transduction steps which lead to T cell activation.

The compounds disclosed in this invention may be used in combination with other drugs and therapies used in the treatment of T cell mediated disease. For example, the compounds of the Formula I could be used in combination with drugs and therapies used in the treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the Formula I could be used in combination with drugs and therapies such as cyclosporin A used in the prevention or treatment of the acute rejection of transplanted organs.

For example, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of the Formula I may also be used with anti-inflammatory agents such as an inhibitor of the enzyme 5-lipoxygenase. The compounds of the Formula I may also be used with anti-inflammatory agents such as an inhibitor of the enzyme COX-2 such as celecoxib or rofecoxib.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds disclosed in the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceuticallyactive agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of T cell activation. Thus, they are useful as pharmacological standards for use in the development of new biological tests and in the search for new pharmacological agents.

The compounds defined in the invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol methanol, acetone, ether or hexane, alone or in admixture; and (viii) the following abbreviations have been used:

| | |
|---|---|
| DMF | N,N-dimethylformamide |
| DMSO | dimethylsulphoxide |
| THF | tetrahydrofuran |
| NMP | N-methylpyrrolidin-2-one |

EXAMPLE 1

6-methoxy-4-(2,3-methylenedioxyanilino)-7-(3-morpholinopropoxy)quinazoline

A mixture of 4-chloro-6-methoxy-7-(3-morpholinopropoxy)quinazoline (0.1 g), 2,3-methylenedioxyaniline (0.048 g), pentan-2-ol (5 ml) and a solution of hydrogen chloride in isopropanol (6M, 4 drops) was stirred and heated to 100° C. for 5 hours. The resultant mixture was cooled to ambient temperature and the precipitate was isolated by filtration, washed with pentan-2-ol and dried under vacuum. There was thus obtained the title compound (0.138 g) as a dihydrochloride salt; NMR Spectrum: (DMSOd$_6$ and CF$_3$COOD) 2.35 (m, 2H), 2.5 (m, 2H), 3.15 (m, 2H), 3.3 (m, 2H), 3.55 (d, 2H), 3.8 (t, 2H), 4.05 (s, 3H), 4.35 (t, 2H), 6.1 (s, 2H), 7.0 (m, 3H), 7.4 (s, 1H), 8.2 (s, 1H), 8.85 (s, 1H); Mass Spectrum: M+H$^+$ 439; Elemental Analysis: Found C, 52.8; H, 5.56; N, 10.68; C$_{23}$H$_{26}$N$_4$O$_5$2HCl0.5H$_2$O requires C, 53.08; H, 5.62; N, 10.77%.

The 4-chloro-6-methoxy-7-(3-morpholinopropoxy) quinazoline used as a starting material was prepared as follows:

A mixture of 2-amino-4-benzyloxy-5-methoxybenzamide (J. Med. Chem., 1977, 20, 146–149; 10 g), (3-dimethylamino-2-azaprop-2-en-1-ylidene)dimethylammonium chloride (Gold's reagent, 7.4 g) and dioxane (100 ml) was stirred and heated to reflux for 24 hours. Sodium acetate (3.02 g) and acetic acid (1.65 ml) were added and the reaction mixture was heated for a further 3 hours. The mixture was evaporated and water was added to the residue. The resultant solid was collected by filtration, washed with water and dried. The material was recrystallised from acetic acid to give 7-benzyloxy-6-methoxy-3,4-dihydroquinazolin-4-one (8.7 g).

After repetition of the reaction so described, a mixture of 7-benzyloxy-6-methoxy-3,4-dihydroquinazolin-4-one (35 g), thionyl chloride (440 ml) and DMF (1.75 ml) was heated to reflux for 4 hours. The thionyl chloride was evaporated under vacuum and the residue was azeotroped with toluene three times. The residue was dissolved in N-methylpyrrolidin-2-one (250 ml) to give a solution of 7-benzyloxy-4-chloro-6-methoxyquinazoline.

Phenol (29.05 g) was dissolved in N-methylpyrrolidin-2-one (210 ml) and sodium hydride (60% dispersion in mineral oil; 11.025 g) was added in portions with cooling. The resultant mixture was stirred at ambient temperature for 3 hours. The resultant viscous suspension was diluted with N-methylpyrrolidin-2-one (180 ml) and stirred overnight. The above-mentioned solution of 7-benzyloxy-4-chloro-6-methoxyquinazoline was added and the resultant suspension was stirred and heated to 100° C. for 2.5 hours. The mixture was allowed to cool to ambient temperature and poured into water (1.5 L) with vigorous stirring. The precipitate was collected by filtration, washed with water and dried under vacuum. The material so obtained was dissolved in methylene chloride and the solution was washed with brine and filtered through phase separating paper. The solution was evaporated under vacuum and the resultant residue was triturated under diethyl ether. There was thus obtained 7-benzyloxy-6-methoxy-4-phenoxyquinazoline (87.8 g); NMR Spectrum: (CDCl$_3$) 4.09 (s, 3H), 5.34 (s, 2H), 7.42 (m, 12H), 7.63 (s, 1H).

A mixture of a portion (36.95 g) of the material so obtained and trifluoroacetic acid (420 ml) was heated to reflux for 3 hours. The reaction mixture was allowed to cool and evaporated under vacuum. The residue was stirred mechanically under water, basified by the addition of a saturated aqueous sodium bicarbonate solution and stirred overnight. The water was decanted and the residual solid was suspended in acetone. After stirring, the white solid was collected by filtration, washed with acetone and dried to give 7-hydroxy-6-methoxy-4-phenoxyquinazoline (26.61 g);

NMR Spectrum: (DMSOd$_6$) 3.97 (s, 3H), 7.22 (s, 1H), 7.3 (m, 3H), 7.47 (t, 2H), 7.56 (s, 1H), 8.47 (s, 1H), 10.7 (s, 1H).

A mixture of 7-hydroxy-6-methoxy-4-phenoxyquinazoline (25.27 g), 3-morpholinopropyl chloride (18.48 g), potassium carbonate (39.1 g) and DMF (750 ml) was stirred and heated to 90° C. for 3 hours. The mixture was allowed to cool to ambient temperature and filtered. The filtrate was evaporated and the residue was triturated under ethyl acetate. There was thus obtained 6-methoxy-7-(3-morpholinopropoxy)-4-phenoxyquinazoline (31.4 g); NMR Spectrum: (DMSOd$_6$) 1.97 (m, 2H), 2.39 (t, 4H), 2.47 (t, 2H), 3.58 (t, 4H), 3.95 (s, 3H), 4.23 (t, 2H), 7.31 (m, 3H), 7.36 (s, 1H), 7.49 (t, 2H), 7.55 (s, 1H), 8.52 (s, 1H).

A mixture of the material so obtained and 6N aqueous hydrochloric acid solution (800 ml) was stirred and heated to reflux for 1.5 hours. The reaction mixture was decanted and concentrated to a volume of 250 ml. The mixture was basified to pH9 by the addition of a saturated aqueous sodium bicarbonate solution and extracted with methylene chloride (4×400 ml). The combined extracts were filtered through phase separating paper and the filtrate was evaporated. The resultant solid was triturated under ethyl acetate to give 6-methoxy-7-(3-morpholinopropoxy)-3,4-dihydroquinazolin-4-one (23.9 g); NMR Spectrum: (DMSOd$_6$) 1.91 (m, 2H), 2.34 (t, 4H), 2.42 (t, 2H), 3.56 (t, 4H), 3.85 (s, 3H), 4.12 (t, 2H), 7.11 (s, 1H), 7.42 (s, 1H), 7.96 (s, 1H), 12.01 (s, 1H).

A mixture of the material so obtained, thionyl chloride (210 ml) and DMF (1.8 ml) was heated to reflux for 1.5 hours. The thionyl chloride was removed by evaporation under vacuum and the residue was azeotroped with toluene three times. The residue was taken up in water and basified to pH8 by the addition of a saturated aqueous sodium bicarbonate solution. The resultant aqueous layer was extracted with methylene chloride (4×400 ml). The combined extracts were washed with water and with brine and dried over magnesium sulphate. The solution was filtered and evaporated. The resultant solid was triturated under ethyl acetate to give 4-chloro-6-methoxy-7-(3-morpholinopropoxy)quinazoline (17.39 g); NMR Spectrum: (CDCl$_3$) 2.1–2.16 (m, 2H), 2.48 (br s, 4H), 2.57 (t, 2H), 3.73 (t, 4H), 4.05 (s, 3H), 4.29 (t, 2H), 7.36 (s, 1H), 7.39 (s, 1H), 8.86 (s, 1H).

The 3-morpholinopropyl chloride used as a reagent was obtained as follows:

A mixture of morpholine (52.2 ml), 1-bromo-3-chloropropane (30 ml) and toluene (180 ml) was heated to 70° C. for 3 hours. The solid was removed by filtration and the filtrate was evaporated under vacuum. The resultant oil was decanted from the additional solid which was deposited and the oil was purified by vacuum distillation to yield 3-morpholinopropyl chloride (37.91 g); NMR Spectrum: (DMSOd$_6$) 1.85 (m, 2H), 2.3 (t, 4H), 2.38 (t, 2H), 3.53 (t, 4H), 3.65 (t, 2H).

The 2,3-methylenedioxyaniline used as a starting material was prepared as follows:

A mixture of 2,3-dihydroxybenzoic acid (5 g), methanol (50 ml) and concentrated sulphuric acid (10 drops) was stirred and heated to 60° C. for 24 hours. The mixture was evaporated and the residue was taken up in ethyl acetate. The organic solution was washed with a saturated solution of sodium bicarbonate, dried over magnesium sulphate and evaporated to give methyl 2,3-dihydroxybenzoate (2.19 g); NMR Spectrum: (CDCl$_3$) 3.95 (s, 3H), 5.7 (s, 1H), 6.8 (t, 1H), 7.15 (d, H), 7.35 (d, H).

After repetition of the previous reaction, a mixture of methyl 2,3-dihydroxybenzoate (2.8 g), potassium fluoride (4.8 g) and DMF (45 ml) was stirred at ambient temperature for 30 minutes. Dibromomethane (1.28 ml) was added and the mixture was heated to 120° C. for 3 hours. The mixture was cooled to ambient temperature, poured into water and extracted with diethyl ether. The organic phase was washed with water and with brine, dried over magnesium sulphate and evaporated. The residue was purified by column chromatography using a 9:1 mixture of petroleum ether (b.p. 40–60° C.) and ethyl acetate as eluent. There was thus obtained methyl 2,3-methylenedioxybenzoate (2.3 g) as a solid; NMR Spectrum: (CDCl$_3$) 3.95 (s, 3H), 6.1 (s, 2H), 6.85 (t, 1H), 7.0 (d, 1H), 7.45 (d, 1H).

A mixture of the material so obtained, a 2N aqueous potassium hydroxide solution (15.5 ml) and methanol (40 ml) was stirred at ambient temperature for 2 hours. The solution was concentrated to about one quarter of the original volume and cooled in an ice bath. The mixture was acidified to pH 3.5 by the addition of a 2N aqueous hydrochloric acid solution. The resultant precipitate was collected by filtration and washed in turn with water and diethyl ether. There was thus obtained 2,3-methylenedioxybenzoic acid (1.87 g); NMR Spectrum: (DMSOd$_6$) 6.1 (s, 1H), 6.9 (t, 1H), 7.15 (d, 1H), 7.3 (d, 1H), 13.0 (br s, 1H).

The material so obtained was suspended in anhydrous dioxane (30 ml) and anhydrous diphenylphosphoryl azide (2.45 ml), triethylamine (1.6 ml) and tert-butanol (9 ml) were added. The mixture was heated to reflux for 5 hours. The mixture was cooled to ambient temperature, concentrated by evaporation and diluted with ethyl acetate. The organic phase was washed in turn with a 5% aqueous citric acid solution, water, an aqueous sodium bicarbonate solution and brine and dried over magnesium sulphate. The solvent was evaporated and the residue was purified by column chromatography on silica using a 19:1 mixture of petroleum ether (b.p. 40–60° C.) and ethyl acetate as eluent. There was thus obtained tert-butyl 2,3-methylenedioxyphenylcarbamate (1.98 g) as a solid; NMR Spectrum: (CDCl$_3$) 1.55 (s, 9H), 5.95 (s, 2H), 6.4 (br s, 1H), 6.55 (d, 1H), 6.8 (t, 1H), 7.45 (d, 1H).

A 5N aqueous hydrochloric acid solution (30 ml) was added to a solution of tert-butyl 2,3-methylenedioxyphenylcarbamate (1.9 g) in ethanol (38 ml) and the reaction mixture was stirred at ambient temperature for 20 hours. The ethanol was evaporated and the residual aqueous phase was washed with diethyl ether and neutralised to pH7 by the addition of solid potassium hydroxide. The resultant mixture was filtered and the aqueous phase was extracted with diethyl ether. The organic phase was washed with brine, dried over magnesium sulphate and evaporated. There was thus obtained 2,3-methylenedioxyaniline (1.0 g) as an oil; NMR Spectrum: (CDCl$_3$) 3.0 (br s, 2H), 5.9 (s, 2H), 6.3 (m, 2H), 7.25 (t, 1H).

EXAMPLE 2

Using an analogous procedure to that described in Example 1, the appropriate 4-chloroquinazoline was reacted with the appropriate 2,3-methylenedioxyaniline to give the compounds described in Table I. Unless otherwise stated, each compound described in Table I was obtained as a dihydrochloride salt.

TABLE I

[Structure: Quinazoline core with MeO at 6-position, R¹ at 7-position, and 4-position substituted with NH-benzodioxole bearing R² group]

| Compound No. & Note | R¹ | R² |
|---|---|---|
| [1] | 3-(1,1-dioxotetrahydro-4H-1,4-thiazin-4-yl)propoxy | hydrogen |
| [2] | 3-pyrrolidin-1-ylpropoxy | hydrogen |
| [3] | 3-(4-methylpiperazin-1-yl)propoxy | hydrogen |
| [4] | 3-piperidinopropoxy | hydrogen |
| [5] | N-methylpiperidin-4-ylmethoxy | hydrogen |
| [6] | 2-[2-(4-methylpiperazin-1-yl)ethoxy]ethoxy | hydrogen |
| [7] | methoxy | hydrogen |
| [8] | benzyloxy | hydrogen |
| [9] | 3-pyrrolidin-1-ylpropoxy | 6-chloro |
| [10] | 3-morpholinopropoxy | 6-chloro |
| [11] | 3-(4-methylpiperazin-1-yl)propoxy | 6-chloro |
| [12] | N-methylpiperidin-4-ylmethoxy | 6-chloro |
| [13] | benzyloxy | 6-chloro |
| [14] | 3-morpholinopropoxy | 6-bromo |
| [15] | 3-methylsulphonylpropoxy | 6-bromo |
| [16] | 3-morpholinopropoxy | 5-methoxy |
| [17] | 2-acetoxy-3-morpholinopropoxy | hydrogen |
| [18] | 2-acetoxy-3-pyrrolidin-1-ylpropoxy | hydrogen |
| [19] | 2-acetoxy-3-piperidinopropoxy | hydrogen |
| [20] | 2-acetoxy-3-(4-cyanomethylpiperazin-1-yl)propoxy | hydrogen |
| [21] | 2-acetoxy-3-(N-isopropyl-N-methylamino)propoxy | hydrogen |
| [22] | 3-(4-methylpiperazin-1-yl)propoxy | 5-methoxy |
| [23] | 2-(N-methylpiperidin-4-yl)ethoxy | hydrogen |
| [24] | piperidin-4-ylmethoxy | hydrogen |
| [25] | 2-piperidin-4-ylethoxy | hydrogen |
| [26] | N-(2-morpholinoethyl)piperidin-4-ylmethoxy | hydrogen |

Notes

[1] The product gave the following characterising data; NMR Spectrum: (DMSOd$_6$ and CF$_3$COOD) 2.35(m, 2H), 3.45(t, 2H), 3.75(br s, 4H), 3.85 (br s, 4H), 4.05(s, 3H), 4.35(t, 2H), 6.1(s, 2H), 7.0(m, 3H), 7.4(s, 1H), 8.2(s, 1H), 8.9(s, 1H); Mass Spectrum: M + H$^+$ 487.
The 4-chloro-7-[3-(1,1-dioxotetrahydro-4H-1,4-thiazin-4-yl)propoxy]-6-methoxyquinazoline used as a starting material was prepared as follows:-
A mixture of 7-benzyloxy-6-methoxy-3,4-dihydroquinazolin-4-one (20.3 g), thionyl chloride (440 ml) and DMF (1.75 ml) was heated to reflux for 4 hours. The thionyl chloride was evaporated under vacuum and the residue was azeotroped with toluene three times to give 7-benzyloxy-4-chloro-6-methoxyquinazoline.
A mixture of the 7-benzyloxy-4-chloro-6-methoxyquinazoline so obtained, potassium carbonate (50 g) and 4-chloro-2-fluorophenol (8.8 ml) and DMF (500 ml) was stirred and heated to 100° C. for 5 hours. The mixture was allowed to cool to ambient temperature, poured into water (2 L) and stirred at ambient temperature for a few minutes. The resultant solid was isolated and washed with water. The solid was dissolved in methylene chloride and the solution was filtered and treated with decolourising charcoal. The resultant solution was filtered and evaporated to give a solid which was triturated under diethyl ether. There was thus obtained 7-benzyloxy-4-(4-chloro-2-fluorophenoxy)-6-methoxyquinazoline (23.2 g); NMR Spectrum: (DMSOd$_6$) 3.98(s, 3H), 5.34(s, 2H), 7.42(m, 9H), 7.69(m, 1H), 8.55(s, 1H).

A mixture of the material so obtained and trifluoroacetic acid (15 ml) was heated to reflux for 3 hours. The reaction mixture was allowed to cool, toluene was added and the mixture was evaporated. The residue was triturated under diethyl ether and then under acetone. The resultant precipitate was isolated and dried to give 4-(4-chloro-2-fluorophenoxy)-7-hydroxy-6-methoxyquinazoline trifluoroacetate salt (21.8 g) which was used without further purification.

3-(1,1-Dioxotetrahydro-4H-1,4-thiazin-4-yl)propan-1-ol (4.2 g) and 1,1'-(azodicarbonyl)dipiperidine (11.7 g) were added in turn to a mixture of 4-(4-chloro-2-fluorophenoxy)-7-hydroxy-6-methoxyquinazoline (5.0 g), tributylphosphine (11.1 ml) and methylene chloride (150 ml). The resultant mixture was stirred at ambient temperature overnight. The mixture was diluted with diethyl ether (300 ml) and the precipitate was removed by filtration. The filtrate was evaporated and the residue was purified by column chromatography on silica using a 19:1 mixture of methylene chloride and methanol as eluent. The material so obtained was triturated under ethyl acetate and dried to give 4-(4-chloro-2-fluorophenoxy)-7-[3-(1,1-dioxotetrahydro-4H-1,4-thiazin-4-yl)propoxy]-6-methoxyquinazoline (5.4 g); NMR Spectrum: (DMSOd$_6$) 1.86(m, 2H), 2.65(t, 2H), 2.92(m, 4H), 3.08(m, 4H), 3.97(s, 3H), 4.26(t, 2H), 7.4(m, 1H), 7.42(s, 1H), 7.56(m, 2H), 7.68(m, 1H), 8.54(s, 1H).

A mixture of a portion (3.5 g) of the material so obtained and a 2N aqueous hydrochloric acid solution (56 ml) was stirred and heated to 95° C. for 2 hours. The reaction mixture was cooled to ambient temperature and treated with solid sodium bicarbonate to give a thick paste which was diluted with water and filtered. The solid was transferred to a flask and azeotroped with toluene twice to give a dry solid. The solid was purified by column chromatography on silica using a 19:1 mixture of methylene chloride and methanol as eluent. There was thus obtained 7-[3-(1,1-dioxotetrahydro-4H-1,4-thiazin-4-yl)propoxy]-6-methoxy-3,4-dihydroquinazolin-4-one (2.26 g) as a white solid; Mass Spectrum: M + H$^+$ 368.

After repetition of the previous reaction, a mixture of 7-[3-(1,1-dioxotetrahydro-4H-1,4-thiazin-4-yl)propoxy]-6-methoxy-3,4-dihydroquinazolin-4-one (4.2 g), thionyl chloride (45 ml) and DMF (0.1 ml) was heated to reflux for 2.5 hours. The residue was diluted with toluene and was evaporated under vacuum. The residue was taken up in water and basified to pH 8 with a saturated aqueous sodium bicarbonate solution. The mixture was extracted with methylene chloride and the organic layer was washed in turn with water and brine. The organic solution was filtered through phase separating paper and evaporated to give an orange solid which was purified by column chromatography on silica using a 19:1 mixture of methylene chloride and methanol as eluent. The resultant solid was triturated under diethyl ether and dried to give 4-chloro-7-[3-(1,1-dioxotetrahydro-4H-1,4-thiazin-4-yl)propoxy]-6-methoxyquinazoline (2.27 g); Mass Spectrum: M + H$^+$ 386.

The 3-(1,1-dioxotetrahydro-4H-1,4-thiazin-4-yl)propan-1-ol used as an intermediate was obtained as follows:-
A mixture of 3-aminopropan-1-ol (0.65 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4-yl)propan-1-ol (0.8 g); NMR Spectrum: (CDCl$_3$) 1.7–1.8(m, 2H), 2.73(t, 2H), 3.06(br s, 8H), 3.25(s, 1H), 3.78(t, 2H); Mass Spectrum: M + H$^+$ 194.

[2] The product gave the following characterising data; NMR Spectrum: (DMSOd$_6$ and CF$_3$COOD) 1.8(m, 2H), 2.05(m, 2H), 2.3(m, 2H), 3.05(m, 2H), 3.35(t, 2H), 3.6(m, 2H), 4.0(s, 3H), 4.3(t, 2H), 6.1(s, 2H), 6.95(m, 3H), 7.4(s, 1H), 8.2(s, 1H), 8.85(s, 1H); Mass Spectrum: M + H$^+$ 423.
The 4-chloro-7-(3-pyrrolidin-1-ylpropoxy)-6-methoxyquinazoline used as a starting material was prepared as follows:-
A mixture of 4-hydroxy-3-methoxybenzoic acid (8.4 g), 3-(pyrrolidin-1-yl) propyl chloride (J. Amer. Chem. Soc., 1955, 77, 2272; 14.75 g), potassium carbonate (13.8 g), potassium iodide (1.66 g) and DMF (150 ml) was stirred and heated to 100° C. for 3 hours. The mixture was allowed to cool to ambient temperature, filtered and the filtrate was evaporated. The residue was dissolved in ethanol (75 ml), 2N aqueous sodium hydroxide solution (75 ml) was added and the mixture was heated to 90° C. for 2 hours. The mixture was concentrated by evaporation and acidified by the addition of concentrated aqueous hydrochloric acid. The resultant mixture was washed with diethyl ether and then purified by column chromatography using a Diaion (trade mark of Mitsubishi) HP20SS resin column, eluting with water and then with a gradient of methanol (0 to 25%) in dilute hydrochloric acid (pH 2.2). The methanol was removed by evaporation and the aqueous residue was freeze dried to give 3-methoxy-4-(3-pyrrolidin-1-ylpropoxy)benzoic acid hydrochloride (12.2 g); NMR Spectrum: (DMSOd$_6$ and CF$_3$CO$_2$D) 2.2(m, 2H), 3.15(t, 2H), 3.3(t, 2H), 3.5(d, 2H), 3.7(t, 2H), 3.82(s, 3H), 4.05(d, 2H), 4.15(t, 2H), 7.07(d, 1H), 7.48(s, 1H), 7.59(d, 1H).

TABLE I-continued

The material so obtained was dissolved in trifluoroacetic acid (40 ml) and the solution was cooled to 0° C. Fuming nitric acid (2.4 ml) was added slowly. The cooling bath was removed and the reaction mixture was stirred at ambient temperature for 1 hour. The mixture was evaporated and a mixture of ice and water was added to the residue. The mixture was evaporated. The solid residue was dissolved in dilute hydrochloric acid (pH 2.2) and purified by column chromatography using a Diaion HP20SS resin column using a gradient of methanol (0 to 50%) in water. Concentration of the fractions by evaporation gave a precipitate which was collected and dried under vacuum over phosphorus pentoxide. There was thus obtained 5-methoxy-2-nitro-4-(3-pyrrolidin-1-ylpropoxy)benzoic acid hydrochloride (12.1 g, 90%); NMR Spectrum: (DMSOd$_6$ and CF$_3$CO$_2$D) 1.8–1.9(m, 2H), 2.0–2.1(m, 2H), 2.1–2.2(m, 2H), 3.0–3.1(m, 2H), 3.3(t, 2H), 3.6–3.7(m, 2H), 3.95(s, 3H), 4.25(t, 2H), 7.35(s, 1H), 7.62(s, 1H).

A mixture of a portion (9.63 g) of the material so obtained, thionyl chloride (20 ml) and DMF (0.05 ml) was heated to 45° C. for 1.5 hours. The excess thionyl chloride was evaporated using the evaporation of added toluene (x2) to remove the last traces. The resultant solid was suspended in a mixture of THF (250 ml) and methylene chloride (100 ml) and ammonia was bubbled though the mixture for 30 minutes. The resultant mixture was stirred for a further 1.5 hours at ambient temperature. The volatiles were removed by evaporation and the residue was dissolved in water and purified by column chromatography using a Diaion HP20SS resin column eluting with a gradient of methanol (0 to 5%) in water. The solvent was removed by evaporation from the fractions containing product. The residue was dissolved in a minimum of methanol and the solution was diluted with diethyl ether. The resultant precipitate was collected by filtration, washed with diethyl ether and dried under vacuum to give 5-methoxy-2-nitro-4-(3-pyrrolidin-1-ylpropoxy)benzamide (7.23 g); NMR Spectrum: (DMSOd$_6$ and CF$_3$CO$_2$D) 1.85–1.95(m, 2H), 2–2.1(m, 2H), 2.15–2.25(m, 2H), 3.0–3.1(m, 2H), 3.31(t, 2H), 3.62(t, 2H), 3.93(s, 3H), 4.2(t, 2H), 7.16(s, 1H), 7.6(s, 1H).

A mixture of a portion (1.5 g) of the material so obtained, concentrated aqueous hydrochloric acid (5 ml) and methanol (20 ml) was warmed to 50° C. to give a solution. Iron powder (1.3 g) was added in portions and the reaction mixture was heated to reflux for 1 hour. The mixture was allowed to cool to ambient temperature. Insoluble material was removed by filtration through diatomaceous earth and the filtrate was evaporated. The residue was purified by column chromatography using a Diaion HP20SS resin column, eluting with water and then with dilute aqueous hydrochloric acid (pH 2). The fractions containing product were concentrated by evaporation and the resultant precipitate was collected by filtration and dried under vacuum over phosphorus pentoxide. There was thus obtained 2-amino-5-methoxy-4-(3-pyrrolidin-1-ylpropoxy)benzamide hydrochloride (1.44 g); NMR Spectrum: (DMSOd$_6$ and CF$_3$CO$_2$D) 1.9(br s, 2H), 2.05(br s, 2H), 2.2(br s, 2H), 3.05(br s, 2H), 3.3(t, 2H), 3.61(br s, 2H), 3.8(s, 3H), 4.11(t, 2H), 7.05(s, 1H), 7.53(s, 1H).

After repetition of the previous reaction, a mixture of 2-amino-5-methoxy-4-(3-pyrrolidin-1-ylpropoxy)benzamide hydrochloride (5.92 g), Gold's reagent (3.5 g) and dioxane (50 ml) was heated to reflux for 5 hours. Acetic acid (0.7 ml) and sodium acetate (1.33 g) were added and the reaction mixture was heated to reflux for a further 5 hours. The mixture was allowed to cool to ambient temperature and evaporated. The residue was dissolved in water, adjusted to pH 8 with 2N aqueous sodium hydroxide solution and purified on a Diaion HP20SS resin column eluting with methanol (gradient 0–50%) in water. The fractions containing product were concentrated by evaporation and then freeze dried to give 6-methoxy-7-(3-pyrrolidin-1-ylpropoxy)-3,4-dihydroquinazolin-4-one (4.55 g); NMR Spectrum: (DMSOd$_6$ and CF$_3$CO$_2$D) 1.9(m, 2H), 2.0–2.1(m, 2H), 2.2–2.3(m, 2H), 3.05(m, 2H), 3.34(t, 2H), 3.6–3.7(br s, 2H), 3.94(s, 3H), 4.27(t, 2H), 7.31(s, 1H), 7.55(s, 1H), 9.02(s, 1H).

A mixture of a portion (1.7 g) of the material so obtained, thionyl chloride (25 ml) and DMF (0.2 ml) was heated at reflux for 3 hours. Excess thionyl chloride was removed by evaporation and by azeotroping with toluene (x2). The residue was suspended in diethyl ether and washed with a 10% aqueous solution of sodium bicarbonate. The organic layer was dried over magnesium sulphate and evaporated to give 4-chloro-6-methoxy-7-(3-pyrrolidin-1-ylpropoxy)quinazoline (1.94 g); NMR Spectrum: (CDCl$_3$) 1.8(br s, 4H), 2.17(m, 2H), 2.6(br s, 4H), 2.7(t, 2H), 4.05(s, 3H), 4.3(t, 2H), 7.35 (s, 1H), 7.38(s, 1H), 8.86(s, 1H).

[3] The product gave the following characterising data; NMR Spectrum: (DMSOd$_6$ and CF$_3$COOD) 2.35(m, 2H), 2.9(s, 3H), 3.3–4.0(br s, 10H), 4.05(s, 3H), 4.35(m, 2H), 6.1(s, 2H), 7.0(m, 3H), 7.4(s, 1H), 8.35(s, 1H), 8.85(s, 1H); Mass Spectrum: M + H$^+$ 452.

The 4-chloro-7-[3-(4-methylpiperazin-1-yl)propoxy]-6-methoxyquinazoline used as a starting material was prepared as follows:-

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60–70° C. under about 0.2 mm Hg to give 1-(3-hydroxypropyl)-4-methylpiperazine (17 g); NMR Spectrum: (CDCl$_3$) 1.72(m, 2H), 2.3(s, 3H), 2.2–2.8(m, 8H), 2.6(t, 2H), 3.8(t, 2H), 5.3(br s, 1H).

4-Toluenesulphonyl chloride (3.2 g) was added to a stirred mixture of 1-(3-hydroxypropyl)-4-methylpiperazine (2.4 g), triethylamine (4.6 ml) and methylene chloride (60 ml) and the resultant mixture was stirred at ambient temperature for 2 hours. The solution was washed in turn with a saturated aqueous sodium bicarbonate solution and with water and filtered through phase separating paper. The organic filtrate was evaporated to give 3-(4-methylpiperazin-1-yl)propyl 4-toluenesulphonate as an oil which crystallised on standing (3.7 g); Mass Spectrum: M + H$^+$ 313.

A mixture of the trifluoroacetic acid salt of 4-(4-chloro-2-fluorophenoxy)-7-hydroxy-6-methoxyquinazoline (3.2 g), 3-(4-methylpiperazin-1-yl)propyl 4-toluenesulphonate (3.0 g), potassium carbonate (6.1 g) and DMF (60 ml) was stirred at 90° C. for 5 hours. The resultant mixture was cooled to ambient temperature, poured into water (700 ml) and extracted with ethyl acetate (5 times). The combined extracts were washed in turn with water, a saturated aqueous sodium bicarbonate solution, water and brine. The ethyl acetate solution was dried over magnesium sulphate and evaporated. The residue was purified by column chromatography on silica using a 100: 8:1 mixture of methylene chloride, methanol and a concentrated aqueous ammonium hydroxide solution (0.88 g/ml) as eluent. The material so obtained was triturated under diethyl ether. There was thus obtained 4-(4-chloro-2-fluorophenoxy)-6-methoxy-7-[3-(4-methylpiperazin-1-yl)propoxy] quinazoline (1.64 g); NMR Spectrum: (DMSOd$_6$) 1.95(m, 2H), 2.14(s, 3H), 2.35(m, 8H), 2.44(t, 2H), 3.96(s, 3H), 4.22(t, 2H), 7.38(s, 1H), 7.4 (m, 1H), 7.54(m, 2H), 7.68(m, 1H), 8.55(s, 1H).

After repetition of the previous reaction, a mixture of 4-(4-chloro-2-fluorophenoxy)-6-methoxy-7-[3-(4-methylpiperazin-1-yl)propoxy]quinazoline (2.6 g) and 2N aqueous hydrochloric acid solution (45 ml) was stirred and heated at 95° C. for 2 hours. The mixture was cooled to ambient temperature and basified by the addition of solid sodium bicarbonate The mixture was evaporated and the residue was purified by column chromatography on silica using a 50: 8:1 mixture of methylene chloride, methanol and a concentrated aqueous ammonium hydroxide solution (0.88 g/ml) as eluent. There was thus obtained 6-methoxy-7-[3-(4-methylpiperazin-1-yl)propoxy]-3,4-dihydroquinazolin-4-one (1.8 g,); Mass Spectrum: M + H$^+$ 333.

After repetition of the previous reaction, a mixture of 6-methoxy-7-[3-(4-methylpiperazin-1-yl)propoxy]-3,4-dihydroquinazolin-4-one (2.15 g), thionyl chloride (25 ml) and DMF (0.18 ml) was stirred and heated to reflux for 2 hours. The thionyl chloride was evaporated under vacuum and the residue azeotroped twice with toluene. The residue was taken up in water, basified by the addition of a saturated aqueous sodium bicarbonate solution and extracted with methylene chloride (4 times). The combined extracts were washed in turn with water and brine and filtered through phase separating paper. The filtrate was evaporated under vacuum and the residue was purified by column chromatography on silica using a 100: 8:1 mixture of methylene chloride, methanol and a concentrated aqueous ammonium hydroxide solution (0.88 g/ml) as eluent. The solid so obtained was triturated under acetone, filtered and dried to give 4-chloro-6-methoxy-7-[3-(4-methylpiperazin-1-yl)propoxy]quinazoline (1.2 g); Mass Spectrum: M + H$^+$ 351.

[4] The product gave the following characterising data; NMR Spectrum: (DMSOd$_6$ and CF$_3$COOD) 1.4(m, 1H), 1.7–1.9(m, 5H), 2.35(m, 2H), 2.95 (m, 2H), 3.25(m, 2H), 3.55(m, 2H), 4.05(s, 3H), 4.3(t, 2H), 6.1(s, 2H), 7.0(m, 3H), 7.45(s, 1H), 8.25(s, 1H), 8.85(s, 1H); Mass Spectrum: M + H$^+$ 437.

The 4-chloro-7-(3-piperidinopropoxy)-6-methoxyquinazoline used as a starting material was prepared as follows:-

TABLE I-continued

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60–80° C.) and the resultant solid was collected and dried under vacuum. There was thus obtained 7-benzyloxy-6-methoxy-3-pivaloyloxymethyl-3,4-dihydroquinazolin-4-one (10 g); NMR Spectrum: (DMSOd$_6$) 1.11(s, 9H), 3.89(s, 3H), 5.3(s, 2H), 5.9(s, 2H), 7.27(s, 1H), 7.35(m, 1H), 7.47(t, 2H), 7.49(d, 2H), 7.51(s, 1H), 8.34(s, 1H).

A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by filtration and the solvent was evaporated. The residue was triturated under diethyl ether and the resultant solid was collected and dried under vacuum. There was thus obtained 7-hydroxy-6-methoxy-3-pivaloyloxymethyl-3,4-dihydroquinazolin-4-one (4.36 g); NMR Spectrum: (DMSOd$_6$) 1.1(s, 9H), 3.89(s, 3H), 5.89(s, 2H), 7.0(s, 1H), 7.48(s, 1H), 8.5(s, 1H).

Diethyl azodicarboxylate (3.9 ml) was added dropwise to a stirred mixture of 7-hydroxy-6-methoxy-3-pivaloyloxymethyl-3,4-dihydroquinazolin-4-one (5 g), 3-bromopropanol (2.21 ml), triphenylphosphine (6.42 g) and methylene chloride (50 ml) and the mixture was stirred at ambient temperature for 2 hours. The mixture was evaporated and the residue was purified by column chromatography on silica using a 19:1 mixture of methylene chloride and methanol as eluent. There was thus obtained 7-(3-bromopropoxy)-6-methoxy-3-pivaloyloxymethyl-3,4-dihydroquinazolin-4-one (6 g); NMR Spectrum: (DMSOd$_6$) 1.12(s, 9H), 2.32(t, 2H), 3.7(t, 2H), 3.9(s, 3H), 4.25 (t, 2H), 5.9(s, 2H), 7.2(s, 1H), 7.61(s, 1H), 8.36(s, 1H).

A mixture of a portion (2.89 g) of the material so obtained and piperidine (10 ml) was stirred and heated to 100° C. for 1 hour. The mixture was evaporated and the residue was partitioned between methylene chloride and a saturated aqueous ammonium chloride solution. The organic phase was washed with brine, dried over magnesium sulphate and evaporated. There was thus obtained 6-methoxy-7-(3-piperidinopropoxy)-3-pivaloyloxymethyl-3,4-dihydroquinazolin-4-one (2.4 g); NMR Spectrum: (DMSOd$_6$) 1.15(s, 9H), 1.35–1.5(m, 1H), 1.6–1.8(m, 3H), 1.8–1.9(d, 2H), 2.2–2.3(m, 2H), 2.95(t, 2H), 3.25(t, 2H), 3.55(d, 2H), 3.95(s, 3H), 4.25(t, 2H), 5.94(s, 2H), 7.24(s, 1H), 7.56(s, 1H), 8.36(s, 1H).

A mixture of the material so obtained and a 7N solution of ammonia in methanol (50 ml) was stirred at ambient temperature for 16 hours. The mixture was evaporated and the residue was triturated under diethyl ether. The resultant solid was isolated, washed in turn with diethyl ether and a 1:1 mixture of diethyl ether and methylene chloride and dried under vacuum. There was thus obtained 6-methoxy-7-(3-piperidinopropoxy)-3,4-dihydroquinazolin-4-one (1.65 g); NMR Spectrum: (DMSOd$_6$) 1.3–1.4(m, 2H), 1.4–1.55(m, 4H), 1.85–1.95(m, 2H), 2.35(br s, 4H), 2.4(t, 2H), 3.9(s, 3H), 4.15(t, 2H), 7.11(s, 1H), 7.44(s, 1H), 7.9(s, 1H).

A mixture of the material so obtained, thionyl chloride (15 ml) and DMF (1.5 ml) was heated to reflux for 3 hours. The mixture was evaporated. Toluene was added and the mixture was again evaporated. The residue was partitioned between methylene chloride and a saturated aqueous sodium bicarbonate solution (the basicity of which was adjusted to pH 10 by adding 6N aqueous sodium hydroxide). The organic layer was separated, washed with brine, dried over magnesium sulphate and evaporated. There was thus obtained 4-chloro-6-methoxy-7-(3-piperidinopropoxy) quinazoline (1.2 g); NMR Spectrum: (DMSOd$_6$) 1.35–1.45(m, 2H), 1.5–1.6(m, 4H), 1.9–2.05(m, 2H), 2.4(br s, 4H), 2.45(t, 2H), 4.0(s, 3H), 4.29(t, 2H), 7.41(s, 1H), 7.46(s, 1H), 8.9(s, 1H).

[5] The product gave the following characterising data; NMR Spectrum: (DMSOd$_6$ and CF$_3$COOD) 1.6(m, 2H), 2.05(m, 2H), 2.15(m, 1H), 2.75(s, 3H), 3.05(m, 2H), 3.5(m, 2H), 4.0(s, 3H), 4.15(d, 2H), 6.1(s, 2H), 7.0(m, 3H), 7.4(s, 1H), 8.2(s, 1H), 8.85(s, 1H); Mass Spectrum: M + H$^+$ 423.

The 4-chloro-7-(N-methylpiperidin-4-ylmethoxy)-6-methoxyquinazoline used as a starting material was prepared as follows:-

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxycarbonylpiperidine-4-carboxylate (48 g); NMR Spectrum: (CDCl$_3$) 1.25(t, 3H), 1.45(s, 9H), 1.55–1.7(m, 2H), 1.8–2.0(d, 2H), 2.35–2.5(m, 1H), 2.7–2.95(t, 2H), 3.9–4.1(br s, 2H), 4.15(q, 2H).

A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05–1.2(m, 2H), 1.35–1.55(m, 10H), 1.6–1.8(m, 2H), 2.6–2.8(t, 2H), 3.4–3.6(t, 2H), 4.0–4.2(br s, 2H).

1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C. The resultant mixture was allowed to warm to ambient temperature and was stirred for 1 hour. Petroleum ether (b.p. 60–80° C., 1L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl)piperidine (76.7 g); NMR Spectrum: (CDCl$_3$) 1.0–1.2(m, 2H), 1.45(s, 9H), 1.65(d, 2H), 1.75–1.9(m, 2H), 2.45(s, 3H), 2.55–2.75(m, 2H), 3.85(d, 1H), 4.0–4.2(br s, 2H), 7.35(d, 2H), 7.8(d, 2H).

A portion (40 g) of the material so obtained was added to a suspension of ethyl 4-hydroxy-3-methoxybenzoate (19.6 g) and potassium carbonate (28 g) in DMF (200 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60–80° C.) and the suspension was stored overnight at 5° C. The resultant solid was collected by filtration, washed with petroleum ether and dried under vacuum. There was thus obtained ethyl 4-(N-tert-butoxycarbonylpiperidin-4-ylmethoxy)-3-methoxybenzoate (35 g), m.p. 81–83° C.; NMR Spectrum: (CDCl$_3$) 1.2–1.35(m, 2H), 1.4(t, 3H), 1.48(s, 9H), 1.8–1.9 (d, 2H), 2.0–2.15(m, 2H), 2.75(t, 2H), 3.9(d, 2H), 3.95(s, 3H), 4.05–4.25(br s, 2H), 4.35(q, 2H), 6.85(d, 1H), 7.55(s, 1H), 7.65(d, 1H).

The material so obtained was dissolved in formic acid (35 ml), formaldehyde (12M, 37% in water, 35 ml) was added and the mixture was stirred and heated to 95° C. for 3 hours. The resultant mixture was evaporated. The residue was dissolved in methylene chloride and hydrogen chloride (3M solution in diethyl ether; 40 ml) was added. The mixture was diluted with diethyl ether and the mixture was triturated until a solid was formed. The solid was collected, washed with diethyl ether and dried under vacuum overnight at 50° C. There was thus obtained ethyl 3-methoxy-4-(N-methylpiperidin-4-ylmethoxy)benzoate (30.6 g); NMR Spectrum: (DMSOd$_6$) 1.29(t, 3H), 1.5–1.7(m, 2H), 1.95(d, 2H), 2.0–2.15(br s, 1H), 2.72 (s, 3H), 2.9–3.1(m, 2H), 3.35–3.5(br s, 2H), 3.85(s, 3H), 3.9–4.05(br s, 2H), 4.3(q, 2H), 7.1(d, 1H), 7.48(s, 1H), 7.6(d, 1H).

TABLE I-continued

The material so obtained was dissolved in methylene chloride (75 ml) and the solution was cooled in an ice-bath to 0–5° C. Trifluoroacetic acid (37.5 ml) was added followed by the dropwise addition over 15 minutes of a solution of fuming nitric acid (24M; 7.42 ml) in methylene chloride (15 ml). The resultant solution was allowed to warm to ambient temperature and was stirred for 2 hours. Volatile materials were evaporated. The residue was dissolved in methylene chloride (50 ml) and the solution was cooled in an ice-bath to 0–5° C. Diethyl ether was added and the resultant precipitate was collected and dried under vacuum at 50° C. The solid was dissolved in methylene chloride (500 ml) and hydrogen chloride (3M solution in diethyl ether; 30 ml) was added followed by diethyl ether (500 ml). The resultant solid was collected and dried under vacuum at 50° C. There was thus obtained ethyl 5-methoxy-4-(N-methylpiperidin-4-ylmethoxy)-2-nitrobenzoate (28.4 g); NMR Spectrum: ($DMSOd_6$) 1.3(t, 3H), 1.45–1.65 (m, 2H), 1.75–2.1(m, 3H), 2.75(s, 3H), 2.9–3.05(m, 2H), 3.4–3.5(d, 2H), 3.95(s, 3H), 4.05(d, 2H), 4.3(q, 2H), 7.32(s, 1H), 7.66(s, 1H).

A mixture of a portion (3.89 g) of the material so obtained, 10% platinum-on-activated carbon (50% wet, 0.389 g) and methanol (80 ml) was stirred under 1.8 atmospheres pressure of hydrogen until uptake of hydrogen ceased. The mixture was filtered and the filtrate was evaporated. The residue was dissolved in water (30 ml) and basified to pH 10 by the addition of a saturated aqueous sodium bicarbonate solution. The mixture was diluted with a 1:1 mixture of ethyl acetate and diethyl ether and the organic layer was separated. The aqueous layer was further extracted with a 1:1 mixture of ethyl acetate and diethyl ether and the organic extracts were combined, washed in turn with water and brine, dried over magnesium sulphate and evaporated. The residue was triturated under a mixture of petroleum ether (b.p. 60–80° C.) and diethyl ether. The solid so obtained was isolated, washed with petroleum ether and dried under vacuum at 60° C. There was thus obtained ethyl 2-amino-5-methoxy-4-(N-methylpiperidin-4-ylmethoxy)benzoate (2.58 g), m.p. 111–112° C.; NMR Spectrum: ($CDCl_3$) 1.35(t, 3H), 1.4–1.5(m, 2H), 1.85(m, 3H), 1.95(t, 2H), 2.29(s, 3H), 2.9(d, 2H), 3.8(s, 3H), 3.85(d, 2H), 4.3(q, 2H), 5.55(br s, 2H), 6.13(s, 1H), 7.33(s, 1H).

A mixture of ethyl 2-amino-5-methoxy-4-(N-methylpiperidin-4-ylmethoxy)benzoate (16.1 g), formamidine acetic acid salt (5.2 g) and 2-methoxyethanol (160 ml) was stirred and heated at 115° C. for 2 hours. Further formamidine acetic acid salt (10.4 g) was added in portions every 30 minutes during 4 hours and heating was continued for 30 minutes after the last addition. The resultant mixture was evaporated. The solid residue was stirred under a mixture of methylene chloride (50 ml) and ethanol (100 ml). The precipitate was removed by filtration and the filtrate was concentrated to a final volume of 100 ml. The resultant suspension was cooled to 5° C. The solid so obtained was collected, washed with cold ethanol and with diethyl ether and dried under vacuum at 60° C. There was thus obtained 6-methoxy-7-(N-methylpipeidin-4-ylmethoxy)-3,4-dihydroquinazolin-4-one (12.7 g); NMR Spectrum: ($DMSOd_6$) 1.25–1.4(m, 2H), 1.75(m, 2H), 1.9(t, 1H), 1.9(s, 3H), 2.16(s, 2H), 2.8(d, 2H), 3.9(s, 3H), 4.0(d, 2H), 7.11(s, 1H), 7.44(s, 1H), 7.97(s, 1H).

A mixture of a portion (2.8 g) of the material so obtained, thionyl chloride (28 ml) and DMF (0.28 ml) was heated to reflux for 1 hour. The mixture was evaporated and the precipitate was triturated under diethyl ether. The resultant solid was isolated and washed with diethyl ether. The solid was then dissolved in methylene chloride and the solution was washed with a saturated aqueous sodium bicarbonate solution. The organic layer was washed in turn with water and brine, dried over magnesium sulphate and evaporated. There was thus obtained 4-chloro-6-methoxy-7-(N-methylpiperidin-4-ylmethoxy)quinazoline (2.9 g); NMR Spectrum: ($DMSOd_6$) 1.3–1.5(m, 2H), 1.75–1.9(m, 4H), 2.0(t, 1H), 2.25(s, 3H), 2.85(d, 2H), 4.02(s, 3H), 4.12(d, 2H), 7.41(s, 1H), 7.46(s, 1H), 8.9(s, 1H).

[6] The product gave the following characterising data; NMR Spectrum: ($DMSOd_6$ and $CF_3COOD$) 2.9(s, 3H), 3.5–3.95(br s, 14H), 4.05(s, 3H), 4.4(br s, 2H), 6.1(s, 2H), 7.0(m, 3H), 7.45(s, 1H), 8.25(s, 1H), 8.85(s, 1H); Mass Spectrum: M + H$^+$ 482.

The 4-chloro-6-methoxy-7-{2-[2-(4-methylpiperazin-1-yl)ethoxy]ethoxy}quinazoline used as a starting material was prepared as follows:-
Diisopropyl azodicarboxylate (5.78 ml) was added dropwise to a stirred mixture of 7-hydroxy-6-methoxy-3-pivaloyloxymethyl-3,4-dihydroquinazolin-4-one (6.0 g), 2-(2-chloroethoxy)ethanol (2.5 ml), triphenyl phosphine (7.7 g) and methylene chloride (150 ml) and the reaction mixture was stirred at ambient temperature for 2 hours. The solvent was evaporated and the residue was purified by column chromatography on silica using a 4:1 mixture of petroleum ether (b.p. 40–60° C.) and ethyl acetate as eluent. There was thus obtained 7-[2-(2-chloroethoxy)ethoxy]-6-methoxy-3-pivaloyloxymethyl)-3,4-dihydroquinazolin-4-one (6.32 g); NMR Spectrum: ($DMSOd_6$) 1.15(s, 9H), 3.8(m, 4H), 3.85(m, 2H), 3.9(s, 3H), 4.3(m, 2H), 5.9(s, 2H), 7.25(s, 1H), 7.5(s, 1H), 8.4(s, 1H), Mass Spectrum: M + H$^+$ 413.

A mixture of a portion (4.0 g) of the material so obtained and N-methylpiperazine (60 ml) was stirred and heated to 80° C. for 5 hours. The mixture was evaporated and the residue partitioned between methylene chloride and a saturated aqueous ammonium chloride solution. The organic phase was dried over magnesium sulphate and evaporated. There was thus obtained 6-methoxy-7-{2-[2-(4-methylpiperazin-1-yl)ethoxy]ethoxy}-3-pivaloyloxymethyl-3,4-dihydroquinazolin-4-one (3.91 g); Mass Spectrum: M + H$^+$ 477.

A mixture of the material so obtained, a 2N aqueous sodium hydroxide solution (7.95 ml) and methanol (20 ml) was stirred at ambient temperature for 2 hours. The basicity of the solution was adjusted to pH 10 by the addition of 2N aqueous hydrochloric acid solution. The mixture was evaporated and the residue was triturated under methylene chloride. The resultant mixture was filtered and the filtrate was evaporated. The resultant residue was triturated under a mixture of diethyl ether and methanol. There was thus obtained 6-methoxy-7-{2-[2-(4-methylpiperazin-1-yl)ethoxy]ethoxy}-3,4-dihydroquinazolin-4-one (2.24 g); Mass Spectrum: M + H$^+$ 363.

A mixture of the material so obtained, thionyl chloride (22 ml) and DMF (0.2 ml) was stirred and heated to 80° C. for 1.5 hours. The mixture was evaporated, toluene was added and the mixture was again evaporated. Methylene chloride and water were added to the residue and the resultant mixture was cooled to 0° C. and adjusted to pH 12 by the successive addition of solid sodium bicarbonate and 2N aqueous sodium hydroxide solution. The organic phase was washed with brine, dried over magnesium sulphate and evaporated. The resultant yellow solid was triturated under a mixture of pentane and diethyl ether. There was thus obtained 4-chloro-6-methoxy-7-{2-[2-(4-methylpiperazin-1-yl)ethoxy]ethoxy}quinazoline (1.19 g); NMR Spectrum: ($DMSOd_6$) 2.15(s, 3H), 2.2–2.45(br s, 8H), 2.5(t, 2H), 3.6(t, 2H), 3.85(t, 2H), 4.05(s, 3H), 4.4(t, 2H), 7.45(s, 1H), 7.5(s, 1H), 8.9(s, 1H), Mass Spectrum: M + H$^+$ 381.

[7] 4-Chloro-6,7-dimethoxyquinazoline, used as a starting material, is described in European Patent Application No. 0566226 (Example 1 thereof). The product was obtained as a monohydrochloride salt and gave the following characterising data; NMR Spectrum: ($DMSOd_6$) 4.0(s, 6H), 6.05(s, 2H), 6.95(m, 3H), 7.35(s, 1H), 8.2(s, 1H), 8.8(s, 1H); Mass Spectrum: M + H$^+$ 326.

[8] Isopropanol was used in place of pentan-2-ol as the reaction solvent and the reaction mixture was heated to 80° C. for 30 minutes. The product gave the following characterising data; NMR Spectrum: ($DMSOd_6$ and $CF_3CO_2D$) 4.0(s, 3H), 5.35(s, 2H), 6.1(s, 2H), 6.95(m, 3H), 7.45(m, 4H), 7.55(d, 2H), 8.15(s, 1H), 8.85(s, 1H); Mass Spectrum: M + H$^+$ 402.

[9] The product gave the following characterising data; NMR Spectrum: ($DMSOd_6$ and $CF_3CO_2D$) 2.35(m, 2H), 3.15(m, 2H), 3.35(m, 2H), 3.55(d, 2H), 3.8(m, 2H), 4.0(m, 2H), 4.05(s, 3H), 4.35(m, 2H), 6.15(s, 2H), 7.05 (d, 1H), 7.15(d, 1H), 7.45(s, 1H), 8.25(s, 1H), 8.9(s, 1H); Mass Spectrum: M − H$^−$ 455 and 457.

The 6-chloro-2,3-methylenedioxyaniline used as a starting material was prepared as follows:-

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition. the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: ($CDCl_3$) 6.0(s, 2H); 6.7(d, 1H); 6.75–6.9(m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH 2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: ($DMSOd_6$) 6.15(s, 2H), 7.0(m, 2H), 13.7(br s, 1H).

TABLE I-continued

A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40–60° C.) and ethyl acetate as eluent. There was thus obtained tert-butyl 5-chloro-l,3-benzodioxol-4-ylcarbamate (1.1 g); NMR Spectrum: (DMSOd$_6$) 1.45(s, 9H), 6.1(s, 2H), 6.85(d, 1H), 6.95(d, 1H), 8.75(s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15(s, 2H), 6.0(s, 2H), 6.25(d, 1H), 6.75(d, 1H).

[10] The product gave the following characterising data; NMR Spectrum: (DMSOd$_6$ and CF$_3$CO$_2$D) 2.35(m, 2H), 3.15(m, 2H), 3.35(m, 2H), 3.5(m, 2H), 3.8(m, 2H), 4.0(m, 2H), 4.05(s, 3H), 4.35(m, 2H), 6.15(s, 2H), 7.05 (d, 1H), 7.15(d, 1H), 7.45(s, 1H), 8.25(s, 1H), 8.9(s, 1H); Mass Spectrum: M + H$^+$ 473 and 475.

[11] The reaction product was purified by column chromatography on silica using a 4:1 mixture of methylene chloride and methanol as eluent. The material so obtained was dissolved in a mixture of methylene chloride and methanol and a 6M solution of hydrogen chloride in diethyl ether was added. The dihydrochloride salt so obtained was isolated and dried and gave the following characterising data; NMR Spectrum: (DMSOd$_6$ and CF$_3$CO$_2$D) 2.65(m, 2H), 2.9(s, 3H), 3.35–3.55(br m, 6H), 3.7–3.9(br m, 4H), 4.05(s, 3H), 4.35(m, 2H), 6.15(s, 2H), 7.05(d, 1H), 7.15(d, 1H), 7.45 (s, 1H), 8.25(s, 1H), 8.85(s, 1H); Mass Spectrum: M + H$^+$ 486 and 488.

[12] The reaction product was purified by column chromatography on silica using a 9:8:2 mixture of methylene chloride, methanol and a saturated methanolic ammonia solution as eluent. The material so obtained was dissolved in a mixture of methylene chloride and methanol and a 6M solution of hydrogen chloride in diethyl ether was added. The dihydrochloride salt so obtained was isolated and gave the following characterising data; NMR Spectrum: (DMSOd$_6$ and K$_2$CO$_3$) 1.55(m, 2H), 1.9(m, 2H), 2.0(m, 1H), 2.5(m, 5H), 3.15(m, 2H), 3.95(s, 3H), 4.05(m, 2H), 6.1 (s, 2H), 6.95(d, 1H), 7.05(d, 1H), 7.2(s, 1H), 7.9(s, 1H), 8.35(d, 1H), 9.55 (s, 1H); Mass Spectrum: M − H$^-$ 455 and 457.

[13] The following variation of the standard reaction procedure was used:-

A mixture of 7-benzyloxy-4-chloro-6-methoxyquinazoline (3 g), 5-chloro-2,3-methylenedioxyaniline (1.88 g), a 6M solution of hydrogen chloride in isopropanol (0.166 ml) and isopropanol (60 ml) was stirred and heated to 80° C. for 3 hours. The reaction mixture was allowed to cooled to ambient temperature and the solid was isolated, washed with isopropanol and with diethyl ether. There was thus obtained the required product as a dihydrochloride salt (4.18 g); NMR Spectrum: (DMSOd$_6$) 4.0(s, 3H), 5.35(s, 2H), 6.15(s, 2H), 7.05(d, 1H), 7.15(d, 1H), 7.45(m, 4H), 7.55(d, 2H), 8.25(s, 1H), 8.8(s, 1H).

[14] The reaction product was purified by column chromatography on silica using increasingly polar mixture of methylene chloride and a saturated methanolic ammonia solution as eluent. The product was obtained as the free base and gave the following characterising data; NMR Spectrum: (DMSOd$_6$ and CF$_3$CO$_2$D) 2.3(m, 2H), 3.15(m, 2H), 3.35(t, 2H), 3.55(s, 2H), 3.7(t, 2H), 4.0(s, 3H), 4.05(m, 2H), 4.35(t, 2H), 6.15(s, 2H), 7.05(d, 1H), 7.3 (d, 1H), 7.4(s, 1H), 8.15(s, 1H), 8.9(s, 1H); Mass Spectrum: M + H$^+$ 517 and 519.

The 6-bromo-2,3-methylenedioxyaniline used as a starting material was prepared from 5-bromo-1,3-benzodioxole (Aldrich Chemical Company) using analogous procedures to those described in Note [9] above for the preparation of 6-chloro-2,3-methylenedioxyaniline. There were thus obtained in turn:-

5-bromo-1,3-benzodioxole-4-carboxylic acid; NMR Spectrum: (DMSOd$_6$ and CF$_3$CO$_2$D) 6.15(s, 2H), 6.95(d, 1H), 7.1(d, 1H); Mass Spectrum: [M − H]$^-$ 243; tert-butyl 5-bromo-1,3-benzodioxol-4-ylcarbamate; NMR Spectrum: (DMSOd$_6$) 1.45(s, 9H), 6.1(s, 2H), 6.80(d, 1H), 7.1(d, 1H), 8.70(s, 1H); and 6-bromo-2,3-methylenedioxyaniline; NMR Spectrum: (DMSOd$_6$) 5.05(s, 2H), 6.0(s, 2H), 6.25(d, 1H), 6.9(d, 1H); Mass Spectrum: M + H$^+$ 216 and 218.

[15] The reaction product was purified by column chromatography on silica using increasingly polar mixture of methylene chloride and a saturated methanolic ammonia solution as eluent. The product was obtained as the free base and gave the following characterising data; NMR Spectrum: (DMSOd$_6$ and CF$_3$CO$_2$D) 2.3(m, 2H), 3.05(s, 3H), 3.35(t, 2H), 4.05(s, 3H), 4.35(t, 2H), 6.15(s, 2H), 7.05(d, 1H), 7.3(d, 1H), 7.35(s, 1H), 8.15(s, 1H), 8.9(s, 1H); Mass Spectrum: M + H$^+$ 510 and 512; Elemental Analysis: Found C, 47.44; H, 4.24; N, 7.92; C$_{20}$H$_{20}$BrN$_3$O$_6$S requires C, 47.07; H, 3.95; N, 8.23%.

The 4-chloro-6-methoxy-7-(3-methylsulphonylpropoxy)quinazoline used as a starting material is described in International Patent Application WO 00/47212 (example 50 thereof).

[16] The product gave the following characterising data; NMR Spectrum: (DMSOd$_6$ and CF$_3$CO$_2$D) 2.35(m, 2H), 3.15(m, 2H), 3.35(m, 2H), 3.55 (m, 2H), 3.75(s, 3H), 3.8(m, 2H), 4.0(br s, 5H), 4.35(m, 2H), 6.05(s, 2H), 6.55(s, 1H), 6.75(s, 1H), 7.4(s, 1H), 8.2(s, 1H), 8.9(s, 1H); Mass Spectrum: M + H$^+$ 469; Elemental Analysis: Found C, 51.59; H, 6.01; N, 9.46; C$_{24}$H$_{28}$N$_4$O$_6$ 2.1HCl 0.8H$_2$O requires C, 51.52; H, 5.71; N, 10.01%.

The 5-methoxy-2,3-methylenedioxyaniline used as a starting material was prepared from 4-bromo-6-methoxy-1,3-benzodioxole (J Org. Chem., 1985, 50, 5077) using analogous procedures to those described in Note [9] above for the preparation of 6-chloro-2,3-methylenedioxyaniline. There were thus obtained in turn:-

6-methoxy-1,3-benzodioxole-4-carboxylic acid; NMR Spectrum: (DMSOd$_6$) 3.75(s, 3H), 6.1(s, 2H), 6.7(s, 1H), 6.85(s, 1H), 13.0(br s, 1H); tert-butyl 6-methoxy-1,3-benzodioxol-4-ylcarbamate; NMR Spectrum: (DMSOd$_6$) 1.45(s, 9H), 3.7(s, 3H), 5.95(s, 2H), 6.4(s, 1H), 6.55(br s, 1H), 8.85 (br s, 1H); Mass Spectrum: M + Na$^+$ 290; and 5-methoxy-2,3-methylenedioxyaniline; NMR Spectrum: (DMSOd$_6$) 3.6(s, 3H), 4.95(br s, 2H), 5.85(s, 2H), 5.9(s, 1H); Mass Spectrum: M + H$^+$ 168.

[17] The product gave the following characterising data; Mass Spectrum: M + H$^+$ 497.

The 7-(2-acetoxy-3-morpholinopropoxy)-4-chloro-6-methoxyquinazoline used as a starting material was prepared as follows:-

A mixture of 7-hydroxy-6-methoxy-3-pivaloyloxymethyl-3,4-dihydroquinazolin-4-one (40 g), 2,3-epoxypropyl bromide (16.8 ml), potassium carbonate (36 g) and DMF (400 ml) was stirred and heated to 70° C. for 1.5 hours. The mixture was poured into an ice-water mixture (1.5 L) and the resultant precipitate was isolated, washed in turn with water and diethyl ether and dried under vacuum over phosphorus pentoxide. There was thus obtained 7-(2,3-epoxypropoxy)-6-methoxy-3-pivaloyloxymethyl-3,4-dihydroquinazolin-4-one (46.7 g).

A mixture of a portion (8 g) of the material so obtained, morpholine (5.8 ml) and chloroform (120 ml) was heated to reflux for 16 hours. The mixture was evaporated and the residue was purified by column chromatography on silica using a 19:1 mixture of methylene chloride and methanol as eluent. There was thus obtained 7-(2-hydroxy-3-morpholinopropoxy)-6-methoxy-3-pivaloyloxymethyl-3,4-dihydroquinazolin-4-one as a foam (8.2 g); NMR Spectrum: (CDCl$_3$) 1.2(s, 9H), 2.5(m, 2H), 2.6(m, 2H), 2.7(m, 2H), 3.5(br s, 1H), 3.75(m, 4H), 3.95(s, 3H), 4.15(m, 2H), 4.25(m, 1H), 5.95(s, 2H), 7.15(s, 1H), 7.65(s, 1H), 8.2(s, 1H).

A mixture of the material so obtained and a saturated methanolic ammonia solution was stirred at ambient temperature for 24 hours. The mixture was evaporated and the resultant solid was washed with diethyl ether and a 19:1 mixture of diethyl ether and methylene chloride. There was thus obtained 7-(2-hydroxy-3-morpholinopropoxy)-6-methoxy-3,4-dihydroquinazolin-4-one (6.34 g); NMR Spectrum: (DMSOd$_6$) 2.4(m, 6H), 3.55 (m, 4H), 3.85(s, 3H), 4.0(m, 2H), 4.15(m, 1H), 4.95(br s, 1H), 7.15(s, 1H), 7.45(s, 1H), 7.95(s, 1H).

A mixture of a portion (5.2 g) of the material so obtained, acetic anhydride (20 ml) and pyridine (1 ml) was stirred at ambient temperature for 30 minutes. The resultant mixture was poured into an ice-water mixture and stirred for 30 minutes. The mixture was then cooled in an ice-bath and a saturated solution of sodium bicarbonate was slowly added to adjust the pH to 9. The mixture was extracted with methylene chloride and the organic phase was washed with water and with brine, dried over magnesium sulphate and evaporated. The residue was purified by column chromatography on silica using a 93:7 mixture of methylene chloride and methanol as eluent. There was thus obtained 7-(2-acetoxy-3-morpholinopropoxy)-6-methoxy-3,4-dihydroquinazolin-4-one as a solid (5 g); NMR Spectrum: (DMSOd$_6$) 2.05(s, 3H), 2.4(m, 4H), 2.6(m, 2H), 3.55(m, 4H), 3.85(s, 3H), 4.35(m, 2H), 5.25(m, 1H), 7.2(s, 1H), 7.45(s, 1H), 8.0(s, 1H); Mass Spectrum: M + H$^+$ 378.

TABLE I-continued

A mixture of the material so obtained, thionyl chloride (60 ml) and DMF (0.5 ml) was heated to reflux for 1 hour. The mixture was evaporated, toluene was added and the mixture was evaporated. A mixture of ice and water was added to the residue and the mixture was basified to pH 8.5 by the addition of a saturated aqueous sodium bicarbonate solution. The mixture was extracted with methylene chloride. The organic phase was washed with water and with brine, dried over magnesium sulphate and evaporated. The residue was purified by column chromatography on silica using a 97:3 mixture of methylene chloride and methanol as eluent. There was thus obtained 7-(2-acetoxy-3-morpholinopropoxy)-4-chloro-6-methoxyquinazoline as a foam (4.56 g); NMR Spectrum: (CDCl$_3$) 2.1(s, 3H), 2.55(m, 4H), 2.7(d, 2H), 3.7(m, 4H), 4.05(s, 3H), 4.35(m, 1H), 4.45(m, 1H), 5.45(m, 1H), 7.4(d, 2H), 8.85(m, 1H); Mass Spectrum: M + H$^+$ 396 and 398.

[18] The product gave the following characterising data; Mass Spectrum: M + H$^+$ 481.

The 7-(2-acetoxy-3-pyrrolidin-1-ylpropoxy)-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with pyrrolidine using an analogous procedure to that described in the second paragraph of the portion of Note [17] immediately above that is concerned with the preparation of starting materials. There was thus obtained 7-(2-hydroxy-3-pyrrolidin-1-ylpropoxy)-6-methoxy-3-pivaloyloxymethyl-3,4-dlhydroquinazolin-4-one.

The material so obtained was taken through an analogous sequence of reactions to those described in the third to fifth paragraphs of the portion of Note [17] immediately above that is concerned with the preparation of starting materials. There was thus obtained 7-(2-acetoxy-3-pyrrolidin-1-ylpropoxy)-4-chloro-6-methoxyquinazoline; NMR Spectrum: (CDCl$_3$ and CD$_3$CO$_2$D) 2.05(s, 4H), 2.15(s, 3H), 3.45(br s, 4H), 3.65(m, 2H), 4.05(s, 3H), 4.4(d, 2H), 5.65(m, 1H), 7.4(s, 1H), 7.55(s, 1H), 8.9(s, 1H).

[19] The product gave the following characterising data; Mass Spectrum: M + H$^+$ 495.

The 7-(2-acetoxy-3-piperidinopropoxy)-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with piperidine using an analogous procedure to that described in the second paragraph of the portion of Note [17] immediately above that is concerned with the preparation of starting materials. There was thus obtained 7-(2-hydroxy-3-piperidinopropoxy)-6-methoxy-3-pivaloyloxymethyl-3,4-dihydroquinazolin-4-one.

The material so obtained was taken through an analogous sequence of reactions to those described in the third to fifth paragraphs of the portion of Note [17] immediately above that is concerned with the preparation of starting materials. There was thus obtained 7-(2-acetoxy-3-piperidinopropoxy)-4-chloro-6-methoxyquinazoline; NMR Spectrum: (CDCl$_3$ and CD$_3$CO$_2$D) 1.6(m, 2H), 1.9(m, 4H), 2.1(s, 3H), 3.2(br s, 4H), 3.5(m, 2H), 4.05(s, 3H), 4.35(m, 2H), 5.7(m, 1H), 7.4(s, 1H), 7.5(s, 1H), 8.9(s, 1H).

[20] The product gave the following characterising data; Mass Spectrum: M + H$^+$ 535.

The 7-[2-acetoxy-3-(4-cyanomethylpiperazin-1-yl)propoxy]-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with 1-cyanomethylpiperazine using an analogous procedure to that described in the second paragraph of the portion of Note [17] immediately above that is concerned with the preparation of starting materials. There was thus obtained 7-[3-(4-cyanomethylpiperazin-1-yl)-2-hydroxypropoxy]-6-methoxy-3-pivaloyloxymethyl-3,4-dihydroquinazo1in-4-one.

The material so obtained was taken through an analogous sequence of reactions to those described in the third to fifth paragraphs of the portion of Note [17] immediately above that is concerned with the preparation of starting materials. There was thus obtained 7-[2-acetoxy-3-(4-cyanomethylpiperazin-1-yl)propoxy]-4-chloro-6-methoxyquinazoline; NMR Spectrum: (CDCl$_3$) 2.1(s, 3H), 2.65(br s, 10H), 3.5(s, 2H), 4.05(s, 3H), 4.4(m, 2H), 5.45(m, 1H), 7.25(s, 1H), 7.4(s, 1H), 8.85(s, 1H); Mass Spectrum: M + H$^+$ 434 and 436.

The 1-cyanomethylpiperazine used as a starting material was prepared as follows:-

A mixture of 1-(tert-butoxycarbonyl)piperazine (5 g), 2-chloroacetonitrile (1.9 ml), potassium carbonate (4 g) and DMF (20 ml) was stirred at ambient temperature for 16 hours. A saturated aqueous ammonium chloride solution was added and the mixture was extracted with ethyl acetate. The organic phase was dried over magnesium sulphate and evaporated. The residue was purified by column chromatography on silica using diethyl ether as eluent. There was thus obtained 1-(tert-butoxycarbonyl)-4-cyanomethylpiperazine as a solid (5.7 g); NMR Spectrum: (CDCl$_3$) 1.45(s, 9H), 2.5(m, 4H), 3.45(m, 4H), 3.55(s, 2H).

A mixture of the material so obtained, trifluoroacetic acid (20 ml) and methylene chloride (25 ml) was stirred at ambient temperature for 4 hours. The mixture was evaporated, toluene was added and the mixture was evaporated again. The residue was purified by column chromatography on silica using a 9:1 mixture of methylene chloride and methanol as eluent. There was thus obtained 1-cyanomethylpiperazine trifluoroacetate salt which was treated with solid sodium bicarbonate in a mixture of methylene chloride, ethyl acetate and methanol to give the free base form (2.9 g); NMR Spectrum: (CDCl$_3$ and DMSOd$_6$) 2.7(m, 4H), 3.2(m, 4H), 3.6(s, 2H), 6.2(br s, 1H).

[21] The product gave the following characterising data; Mass Spectrum: M + H$^+$ 483.

The 7-[2-acetoxy-3-(N-isopropyl-N-methylamino)propoxy]-4-chloro-6-methoxyquinazoline used as a starting material was prepared as follows:-

7-(2,3-Epoxypropoxy)-6-methoxy-3-pivaloyloxymethyl-3,4-dihydroquinazolin-4-one was reacted with N-isopropyl-N-methylamine using an analogous procedure to that described in the second paragraph of the portion of Note [17] immediately above that is concerned with the preparation of starting materials. There was thus obtained 7-[2-hydroxy-3-(N-isopropyl-N-methylamino)propoxy]-6-methoxy-3-pivaloyloxymethyl-3,4-dihydroquinazolin-4-one.

The material so obtained was taken through an analogous sequence of reactions to those described in the third to fifth paragraphs of the portion of Note [17] immediately above that is concerned with the preparation of starting materials. There was thus obtained 7-[2-acetoxy-3-(N-isopropyl-N-methylamino)propoxy]-4-chloro-6-methoxyquinazoline; NMR Spectrum: (CDCl$_3$) 1.0(d, 6H), 2.1(s, 3H), 2.3(s, 3H), 2.6(m, 1H), 2.75(m, 1H), 2.85 (m, 1H), 4.05(s, 3H), 4.35(m, 1H), 4.45(m, 1H), 5.35(m, 1H), 7.25(s, 1H), 7.4(s, 1H), 8.85(s, 1H).

[22] The product gave the following characterising data; NMR Spectrum: (DMSOd$_6$ and CF$_3$CO$_2$D) 1.3(m, 2H), 1.7(m, 2H), 1.9–2.2(m, 4H), 2.8(s, 3H), 3.05(m, 2H), 3.5(m, 2H), 3.75(s, 3H), 4.05(s, 3H), 4.1(m, 2H), 6.05 (s, 2H), 6.55(s, 1H), 6.7(s, 1H), 7.45(s, 1H), 8.2(s, 1H), 8.85(s, 1H).

[23] Isopropanol was used in place of pentan-2-ol as the reaction solvent and the reaction mixture was heated to 80° C. for 1.5 hours. The reaction mixture was cooled to ambient temperature and evaporated. A mixture of the residue and methylene chloride (5 ml) was diluted with 1N aqueous sodium hydroxide solution (2 ml) and extracted with methylene chloride. The organic phase was evaporated and the residue was purified by column chromatography on silica using a 9:10:1 mixture of methylene chloride, ethyl acetate and a saturated methanolic ammonia solution as eluent. The material so obtained was dissolved in diethyl ether and a 6M solution of hydrogen chloride in isopropanol was added. The dihydrochloride salt so obtained was isolated and dried and gave the following characterising data; NMR Spectrum: (DMSOd$_6$ and CF$_3$CO$_2$D) 1.4–1.5(m, 2H), 1.7–1.9 (m, 3H), 2.0(d, 2H), 2.75(s, 3H), 2.95(m, 2H), 3.45(d, 2H), 4.0(s, 3H), 4.3(t, 2H), 6.1(s, 2H), 7.0(m, 3H), 7.38(s, 1H), 8.12(s, 1H), 8.9(s, 1H); Mass Spectrum: M + H$^+$ 437.

The 4-chloro-6-methoxy-7-[2-(N-methylpiperidin-4-yl)ethoxy]quinazoline used as a starting material is described International Patent Application WO 00/47212 (within Example 241 thereof).

[24] 7-(N-tert-Butoxycarbonylpiperidin-4-ylmethoxy)-4-chloro-6-methoxyquinazoline was used as the appropriate 4-chloroquinazoline, isopropanol was used in place of pentan-2-ol as the reaction solvent, a 6M solution of hydrogen chloride in isopropanol (0.02 ml) was added and the reaction mixture was heated to 80° C. for 1 hour. The product was obtained as the monohydrochloride salt and gave the following characterising data; NMR Spectrum: (DMSOd$_6$ and CF$_3$CO$_2$D) 1.5–1.65(m, 2H), 2.0(d, 2H), 2.15–2.3(m, 1H), 2.95(m, 2H), 3.3–3.4(m, 2H), 4.02(s, 3H), 4.1(d, 2H), 6.07(s, 2H), 7.0(s, 3H), 7.4(s, 1H), 8.25(s, 1H), 8.65(m, 1H), 8.8(s, 1H), 8.95(m, 1H); Mass Spectrum: M + H$^+$ 409.

The 7-(N-tert-butoxycarbonylpiperidin-4-ylmethoxy)-4-chloro-6-methoxyquinazoline used as a starting material was prepared as follows:-

TABLE I-continued

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60–80° C.) and the resultant solid was collected and dried under vacuum. There was thus obtained 7-benzyloxy-6-methoxy-3-pivaloyloxymethyl-3,4-dihydroquinazolin-4-one (10 g); NMR Spectrum: (DMSOd$_6$) 1.11(s, 9H), 3.89(s, 3H), 5.3(s, 2H), 5.9(s, 2H), 7.27(s, 1H), 7.35(m, 1H), 7.47(t, 2H), 7.49(d, 2H), 7.51(s, 1H), 8.34(s, 1H).

A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by filtration and the solvent was evaporated. The residue was triturated under diethyl ether and the resultant solid was collected and dried under vacuum. There was thus obtained 7-hydroxy-6-methoxy-3-pivaloyloxymethyl-3,4-dihydroquinazolin-4-one (4.36 g); NMR Spectrum: (DMSOd$_6$) 1.1(s, 9H), 3.89(s, 3H), 5.89(s, 2H), 7.0(s, 1H), 7.48(s, 1H), 8.5(s, 1H).

A mixture of 7-hydroxy-6-methoxy-3-pivaloyloxymethyl-3,4-dihydroquinazolin-4-one (4 g), N-tert-butoxycarbonyl-4-(4-toluenesulphonyloxymethyl)piperidine (10 g), potassium carbonate (7 g) in DMF (50 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60–80° C.) and the suspension was stored overnight at 5° C. The resultant solid was collected by filtration, washed with petroleum ether and dried under vacuum. There was thus obtained 7-(N-tert-butoxycarbonylpiperidin-4-ylmethoxy)-6-methoxy-3-pivaloyloxymethyl-3,4-dihydroquinazolin-4-one which was used without further purification.

A mixture of 7-(N-tert-butoxycarbonylpiperidin-4-ylmethoxy)-6-methoxy-3-pivaloyloxymethyl-3,4-dihydroquinazolin-4-one (6 g) and a saturated methanolic ammonia solution (100 ml) was stirred at ambient temperature for 16 hours. The resultant mixture was evaporated and the residue was triturated under diethyl ether. The solid so obtained was isolated, washed with a 49:1 mixture of diethyl ether and methylene chloride and dried under vacuum. There was thus obtained 7-(N-tert-butoxycarbonylpiperidin-4-ylmethoxy)-6-methoxy-3,4-dihydroquinazolin-4-one (3.3 g); NMR Spectrum: (DMSOd$_6$) 1.12–1.3(m, 2H), 1.42(s, 9H), 1.8(d, 2H), 2.02(m, 1H), 2.7–2.9(m, 2H), 3.9(s, 3H), 4.02(m, 4H), 7.15(s, 1H), 7.45(s, 1H), 8.0(s, 1H).

A mixture of a portion (0.2 g) of the material so obtained, carbon tetrachloride (0.15 ml), triphenylphosphine (0.25 g) and 1,2-dichloroethane (10 ml) was stirred and heated to 70° C. for 2 hours. The mixture was evaporated and the residue was purified by column chromatography on silica using a 5:4:1 mixture of methylene chloride, ethyl acetate and methanol as eluent. There was thus obtained 7-(N-tert-butoxycarbonylpiperidin-4-ylmethoxy)-4-chloro-6-methoxyquinazoline (0.07 g); NMR Spectrum: (DMSOd$_6$) 1.15–1.3(m, 2H), 1.45(s, 9H), 1.8(d, 2H), 2.08(m, 1H), 2.7–2.9(m, 2H), 4.02(m, 5H), 4.12(d, 2H), 7.42(s, 1H), 7.5(s, 1H), 8.9(s, 1H); Mass Spectrum: M + H$^+$ 408.

The N-tert-butoxycarbonyl-4-(4-toluenesulphonyloxymethyl)piperidine used as a starting material was prepared as follows:-

A solution of di-tert-butyl dicarbonate (41.7 g) in ethyl acetate (75 ml) was added dropwise to a stored solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxycarbonylpiperidine-4-carboxylate (48 g); NMR Spectrum: (CDCl$_3$) 1.25(t, 3H), 1.45(s, 9H), 1.55–1.7(m, 2H), 1.8–2.0(d, 2H), 2.35–2.5(m, 1H), 2.7–2.95(t, 2H), 3.9–4.1(br s, 2H), 4.15(q, 2H).

A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05–1.2(m, 2H), 1.35–1.55(m, 10H), 1.6–1.8(m, 2H), 2.6–2.8(t, 2H), 3.4–3.6(t, 2H), 4.0–4.2(br s, 2H).

1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C. The resultant mixture was allowed to warm to ambient temperature and was stirred for 1 hour. Petroleum ether (b.p. 60–80° C., 1 L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl)piperidine (76.7 g); NMR Spectrum: (CDCl$_3$) 1.0–1.2(m, 2H), 1.45(s, 9H), 1.65(d, 2H), 1.75–1.9(m, 2H), 2.45(s, 3H), 2.55–2.75(m, 2H), 3.85(d, 1H), 4.0–4.2(br s, 2H), 7.35(d, 2H), 7.8(d, 2H).

[25] 7-[2-(N-tert-Butoxycarbonylpiperidin-4-yl)ethoxy]-4-chloro-6-methoxyquinazoline was used as the appropriate 4-chloroquinazoline, isopropanol was used in place of pentan-2-ol as the reaction solvent, a 6M solution of hydrogen chloride in isopropanol (0.02 ml) was added and the reaction mixture was heated to 80° C. for 1 hour. The product was obtained as the monohydrochloride salt and gave the following characterising data; NMR Spectrum: (DMSOd$_6$ and CF$_3$CO$_2$D) 1.4–1.55(m, 2H), 1.9(br s, 2H), 1.95(d, 2H), 2.95(m, 2H), 3.4(m, 2H), 4.1(s, 3H), 4.35(m, 2H), 6.15(s, 2H), 7.0(s, 3H), 7.4(s, 1H), 8.15(s, 1H), 8.9(s, 1H); Mass Spectrum: M + H$^+$ 423.

The 7-[2-(N-tert-butoxycarbonylpiperidin-4-yl)ethoxy]-4-chloro-6-methoxyquinazoline used as a starting material was obtained as follows:-

A mixture of 7-hydroxy-6-methoxy-3-pivaloyloxymethyl-3,4-dihydroquinazolin-4-one (2 g), N-tert-butoxycarbonyl-4-[2-(4-toluenesulphonyloxy)ethyl]piperidine (2.84 g), potassium carbonate (1.8 g) and DMF (20 ml) was stirred and heated to 95° C. for 2.5 hours. The resultant mixture was cooled to ambient temperature and poured onto a mixture of ice and water. The mixture was extracted with methylene chloride. The organic layer was washed with brine, dried over magnesium sulphate and evaporated. There was thus obtained 7-[2-(N-tert-butoxycarbonylpiperidin-4-yl)ethoxy]-6-methoxy-3-pivaloyloxymethyl-3,4-dihydroquinazolin-4-one (2 g); NMR Spectrum: (DMSOd$_6$) 1.0–1.15(m, 2H), 1.15(s, 9H), 1.4(s, 9H), 1.6–1.8(m, 3H), 2.6–2.8(m, 2H), 3.92(s, 3H), 3.9–4.0(m, 2H), 4.2(m, 2H), 5.92(s, 2H), 7.2(s, 1H), 7.5(s, 1H), 8.3(s, 1H).

A mixture of 7-[2-(N-tert-butoxycarbonylpiperidin-4-yl)ethoxy]-6-methoxy-3-pivaloyloxymethyl-3,4-dihydroquinazolin-4-one (2 g) and a saturated methanolic ammonia solution (30 ml) was stirred at ambient temperature for 16 hours. The resultant mixture was evaporated and the residue was triturated under diethyl ether. The solid so obtained was isolated, washed with a 49:1 mixture of diethyl ether and methylene chloride and dried under vacuum. There was thus obtained 7-[2-(N-tert-butoxycarbonylpiperidin-4-yl)ethoxy]-6-methoxy-3,4-dihydroquinazolin-4-one (1.3 g); NMR Spectrum: (DMSOd$_6$) 1.0–1.15(m, 2H), 1.4(s, 9H), 1.6–1.8(m, 3H), 2.6–2.8(m, 2H), 3.3–3.5(m, 2H), 3.9(s, 3H), 3.9–4.0(m, 2H), 4.18(m, 2H), 7.15(s, 1H), 7.45(s, 1H), 8.0(s, 1H); Mass Spectrum: M + H$^+$ 404.

Using an analogous procedure to that described in the last paragraph of the portion of Note [24] immediately above that is concerned with the preparation of 7-(N-tert-butoxycarbonylpiperidin-4-ylmethoxy)-4-chloro-6-methoxyquinazoline, 7-[2-(N-tert-butoxycarbonylpiperidin-4-yl)ethoxy]-6-methoxy-3,4-dihydroquinazolin-4-one (0.2 g) was reacted with carbon tetrachloride and triphenylphosphine to give 7-[2-(N-tert-butoxycarbonylpiperidin-4-yl)ethoxy]-4-chloro-6-methoxyquinazoline (0.03 g); NMR Spectrum: (DMSOd$_6$) 1.0–1.2(m, 2H), 1.4(s, 9H), 1.6–1.8(m, 5H), 2.6–2.8(m, 2H), 3.92(d, 2H), 4.0(s, 3H), 4.3(m, 2H), 7.4(s, 1H), 7.5(s, 1H), 8.9(s, 1H).

TABLE I-continued

The N-tert-butoxycarbonyl-4-[2-(4-toluenesulphonyloxy)ethyl]piperidine used as a starting material was prepared by the reaction of 4-toluenesulphonyl chloride with N-tert-butoxycarbonyl-4-(2-hydroxyethyl)piperidine (International Patent Application WO 00/47212, in example 126 thereof) using an analogous procedure to that described in the last paragraph of the portion of Note [24] immediately above that is concerned with the preparation of N-tert-butoxycarbonyl-4-(4-toluenesulphonyloxymethyl)piperidine.

[26] Isopropanol was used in place of pentan-2-ol as the reaction solvent, a 6M solution of hydrogen chloride in isopropanol was added and the reaction mixture was heated to 80° C. for 3 hours. The reaction mixture was evaporated and the residue was purified by column chromatography on silica using increasingly polar mixture of methylene chloride and a saturated methanolic ammonia solution as eluent. The material so obtained was dissolved in diethyl ether and a 3M solution of hydrogen chloride in diethyl ether was added. The precipitate was isolated and dried. The resultant product was obtained as the monohydrochloride salt and gave the following characterising data; NMR Spectrum: (DMSOd$_6$ and CF$_3$CO$_2$D) 1.7–1.9(m, 2H), 2.15(d, 2H), 2.37(m, 1H), 3.1–3.35(m, 6H), 3.6–3.7(m, 6H), 3.8(m, 4H), 4.05(s, 3H), 4.2(br s, 2H), 6.1(s, 2H), 7.02(s, 3H), 7.4(s, 1H), 8.15(s, 1H), 8.9(s, 1H); Mass Spectrum: M + H$^+$ 522.

The 4-chloro-6-methoxy-7-[N-(2-morpholinoethyl)piperidin-4-ylmethoxy]quinazoline used as a starting material was prepared as follows:

A mixture of 7-(N-tert-butoxycarbonylpiperidin-4-ylmethoxy)-6-methoxy-3-pivaloyloxymethyl-3,4-dihydroquinazolin-4-one (12 g), trifluoroacetic acid (25 ml) and methylene chloride (100 ml) was stirred at ambient temperature for 1.5 hours. The mixture was evaporated and the residue was partitioned between methylene chloride and a dilute aqueous sodium bicarbonate solution. The organic layer was washed with water and with brine, dried over magnesium sulphate and evaporated. The residue was triturated under a mixture of diethyl ether and pentane. The resultant solid was isolated and dried under vacuum. There was thus obtained 6-methoxy-7-piperidin-4-ylmethoxy-3-pivaloyloxymethyl-3,4-dihydroquinazolin-4-one (9.1 g); NMR Spectrum: (DMSOd$_6$) 1.15 (s, 9H), 1.2–1.35 (m, 2H), 1.78 (d, 2H), 1.95 (m, 1H), 2.6 (m, 2H), 3.05 (d, 2H), 3.9 (s, 3H), 4.0 (d, 2H), 5.92 (s, 2H), 7.14 (s, 1H), 7.5 (s, 1H), 8.34 (s, 1H); Mass Spectrum: M+H$^+$ 404.

A mixture of a portion (1 g) of the material so obtained, 2-morpholinoethyl chloride hydrochloride salt (0.55 g), potassium iodide (0.21 g), sodium bicarbonate (0.625 g) and methanol (23 ml) was stirred and heated to reflux for 2.5 hours. The mixture was evaporated and the residue was partitioned between methylene chloride and water. The organic layer was washed with water and with brine, dried over magnesium sulphate and evaporated. The residue was purified by column chromatography on silica using a 9:1 mixture of methylene chloride and a saturated methanolic ammonia solution as eluent. The residue was triturated under a mixture of diethyl ether and pentane. The resultant solid was isolated and dried under vacuum. There was thus obtained 6-methoxy-7-[N-(2-morpholinoethyl)piperidin-4-ylmethoxy]-3-pivaloyloxymethyl-3,4-dihydroquinazolin-4-one (0.42 g); NMR Spectrum: (DMSOd$_6$) 1.15 (s, 9H), 1.25–1.4 (m, 2H), 1.7–1.9 (m, 3H), 1.9–2.1 (m, 2H), 2.4 (m, 8H), 2.95 (br s, 2H), 3.58 (m, 4H), 3.9 (s, 3H), 4.01 (d, 2H), 5.9 (s, 2H), 7.18 (s, 1H), 7.5 (s, 1H), 8.38 (s, 1H); Mass Spectrum: M+H$^+$ 517.

A mixture of the material so obtained and a saturated methanolic ammonia solution (10 ml) was stirred at ambient temperature for 16 hours. The mixture was evaporated and the residue was triturated under a 4:1 mixture of diethyl ether and methylene chloride. The resultant solid was isolated, washed with diethyl ether and dried under vacuum. There was thus obtained 6-methoxy-7-[N-(2-morpholinoethyl)piperidin-4-ylmethoxy]-3,4-dihydroquinazolin-4-one (0.29 g); NMR Spectrum: (DMSOd$_6$) 1.25–1.4 (m, 2H), 1.7–1.85 (m, 3H), 1.9–2.1 (in 2H), 2.4 (d, 8H), 2.92 (br s, 2H), 3.55 (m, 4H), 3.88 (s, 3H), 3.98 (d, 2H), 7.1 (s, 1H), 7.45 (s, 1H), 7.98 (s, 1H); Mass Spectrum: M+H$^+$ 403.

A mixture of the material so obtained, thionyl chloride (5 ml) and DMF (0.05 ml) was heated to reflux for 1.5 hours. The mixture was evaporated, toluene was added and the mixture was evaporated. The residue was partitioned between methylene chloride and a cooled 2N aqueous sodium hydroxide solution. The organic layer was separated, washed with water and with brine, dried over magnesium sulphate and evaporated. There was thus obtained 4-chloro-6-methoxy-7-[N-(2-morpholinoethyl)piperidin-4-ylmethoxy]quinazoline (0.115 g); NMR Spectrum: (DMSOd$_6$) 1.25–1.4 (m, 2H), 1.7–1.9 (in, 311), 1.98 (m, 2H), 2.4 (d, 8H), 2.92 (d, 2H), 3.55 (m, 41, 4.02 (s, 3H), 4.1 (d, 2H), 7.4 (s, 1H), 7.45 (s, 1H), 8.88 (s, 1H); Mass Spectrum: M+H$^+$ 421 and 423.

EXAMPLE 3

7-hydroxy-6-methoxy-4-(2,3-methylenedioxyanilino)quinazoline

A mixture of 7-benzyloxy-6-methoxy-4-(2,3-methylenedioxyanilino)quinazoline hydrochloride (21 g), ammonium formate (30.2 g), 10% palladium-on-charcoal catalyst (4.8 g), water (26 ml) and DMF (350 ml) was stirred at ambient temperature for 2 hours. The mixture was filtered and the filtrate was evaporated. The residual oil was triturated under diethyl ether. The solid so obtained was triturated under water, collected by filtration, washed with water and with diethyl ether and dried under vacuum over phosphorus pentoxide. The material so obtained was purified by column chromatography on silica using a 9:1 mixture of methylene chloride and methanol as eluent. There was thus obtained the title compound (15 g); NMR Spectrum: (DMSOd$_6$) 3.95 (s, 3H), 6.0 (s, 2H), 6.85 (m, 2H), 6.95 (d, 1H), 7.05 (s, 1H), 7.8 (s, 1H), 8.3 (s, 1H), 9.4 (s, 1H), 10.3 (s, 1H); Mass Spectrum: M+H$^+$ 312.

EXAMPLE 4

4-(6-chloro-2,3-methylenedioxyanilino)-7-hydroxy-6-methoxyquinazoline

A mixture of 7-benzyloxy 4-(6-chloro-2,3-methylenedioxyanilino)-6-methoxyquinazoline dihydrochloride (3.3 g) and trifluoroacetic acid (60 ml) was heated to reflux for 4 hours. The mixture was evaporated. The residue was diluted with water and methanol and the mixture was basified to pH 7.5 by the addition of a saturated aqueous sodium carbonate solution. The methanol was evaporated and the resultant solid was isolated and washed with water. There was thus obtained the title compound as a solid (2.5 g); NMR Spectrum: (DMSOd$_6$ and CF$_3$CO$_2$D) 3.95 (s, 3H), 6.1 (s, 2H), 6.95 (d, 1H), 7.1 (m, 2H), 8.1 (s, 1H), 8.4 (s, 1H), 9.85 (br s, 1H), 10.7 (br s, 1H); Mass Spectrum: M+H$^+$ 346 and 348.

EXAMPLE 5

6-methoxy-4-(2,3-methylenedioxyanilino)-7-(3-methylsulphonylpropoxy)quinazoline monohydrochloride salt Diethyl azodicarboxylate (0.101 ml) was added dropwise to a stirred mixture of 7-hydroxy-6-methoxy-4-(2,3-methylenedioxyanilino)quinazoline (0.1 g), 3-methylsulphonylpropan-1-ol (0.057 g), triphenylphosphine (0.168 g) and methylene chloride (5 ml) and the reaction mixture was stirred at ambient temperature. After a few minutes further portions of triphenylphosphine (0.084 g) and 3-methylsulphonylpropan-1-ol (0.022 g) were added followed by the dropwise addition of diethyl azodicarboxylate (0.050 ml). After another few minutes third portions of the same amounts of these reagents were added. The reaction mixture was evaporated and the residue was purified by column chromatography on silica using a 10:6:1 mixture of methylene chloride, ethyl acetate and methanol as eluent. The material so obtained was triturated under a 6M solution of hydrogen chloride in diethyl ether. There was thus obtained the title compound (0.108 g) as a white solid; NMR Spectrum: (DMSOd$_6$ and CF$_3$CO$_2$D) 2.3 (m, 2H), 3.05 (s, 3H), 3.35 (m, 2H), 4.0 (s, 3H), 4.35 (t, 2H), 6.1 (s, 2H), 7.0 (m, 3H), 7.3 (s, 1H), 8.1 (s, 1H), 8.15 (s, 1H); Mass Spectrum: M+H$^+$ 432.

The 3-methylsulphonylpropan-1-ol used as a starting material was obtained as follows:

3-Chloroperoxybenzoic acid (67%, 25 g) was added portionwise to a stirred mixture of 3-methylthiopropan-1-ol (5 ml) and methylene chloride and the resultant mixture was stirred at ambient temperature for 1 hour. The resultant mixture was filtered and the filtrate was evaporated. The residue was purified by column chromatography on alumina using a 19:1 mixture of methylene chloride and methanol as eluent to give the required starting material as an oil (4.18 g); NMR Spectrum: (CDCl$_3$) 2.1 (m, 2H), 2.96 (s, 3H), 3.2 (t, 2H), 3.8 (t, 2H); Mass Spectrum: M+H$^+$ 139.

EXAMPLE 6

6,7-di-(2-methoxyethoxy)-4-(2,3-methylenedioxyanilino)quinazoline monohydrochloride salt Using an analogous procedure to that described in Example 1, 4-chloro-6,7-di-(2-methoxyethoxy)quinazoline (U.S. Pat. No. 5,747,498; 0.1 g) was reacted with 2,3-methylenedioxyaniline (0.048 g) to give the title compound (0.121 g); NMR Spectrum: (DMSOd$_6$ and CF$_3$CO$_2$D) 3.5 (s, 6H), 3.8 (m, 4H), 4.35 (m, 4H), 6.05 (s, 2H), 6.95 (m, 3H), 7.4 (s, 1H), 8.2 (s, 1H), 8.85 (s, 1H); Mass Spectrum: M+H$^+$ 414.

EXAMPLE 7

4-(6-chloro-2,3-methylenedioxyanilino)-6-methoxy-7-(2-pyrrolidin-1-ylethoxy)quinazoline Diethyl azodicarboxylate (0.182 ml) was added dropwise to a stirred mixture of 4-(6-chloro-2,3-methylenedioxyanilino)-7-hydroxy-6-methoxyquinazoline (0.2 g), N-(2-hydroxyethyl)pyrrolidine (0.086 g), triphenylphosphine (0.303 g) and methylene chloride (3 ml) and the reaction mixture was stirred at ambient temperature for 15 minutes. The reaction mixture was evaporated and the residue was purified by column chromatography on silica using a 45:4:1 mixture of methylene chloride, methanol and a saturated methanolic ammonia solution as eluent. There was thus obtained the title compound (0.033 g) as a white solid; NMR Spectrum: (DMSOd$_6$ and CF$_3$CO$_2$D) 1.9 (m, 2H), 2.1 (m, 2H), 3.2 (m, 2H), 3.7 (m, 2H), 3.8 (m, 2H), 4.05 (s, 3H), 4.6 (m, 2H), 6.2 (s, 2H), 7.1 (d, 1H), 7.2 (d, 1H), 7.5 (s, 1H), 8.2 (s, 1H), 8.95 (s, 1H); Mass Spectrum: M−H$^−$ 441 and 443.

EXAMPLE 8

Using an analogous procedure to that described in Example 7, the appropriate 7-hydroxyquinazoline was reacted with the appropriate alcohol to give the compounds described in Table II. Unless otherwise stated, each compound described in Table II was obtained as the free base.

TABLE II

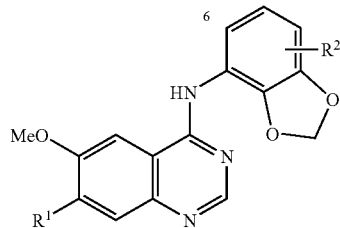

| Compound No. & Note | R$^1$ | R$^2$ |
|---|---|---|
| [1] | 3-diisopropylaminopropoxy | hydrogen |
| [2] | 3-(1,1-dioxotetrahydro-4H-1,4-thiazin-4-yl)propoxy | 6-chloro |
| [3] | 3-piperidinopropoxy | 6-chloro |
| [4] | 3-methylsulphonylpropoxy | 6-chloro |
| [5] | 3-diisopropylaminopropoxy | 6-chloro |
| [6] | 2-(4-methylpiperazin-1-yl)ethoxy | hydrogen |
| [7] | 2-piperidinoethoxy | 6-chloro |
| [8] | 2-(4-methylpiperazin-1-yl)ethoxy | 6-chloro |
| [9] | 2-pyrrol-1-ylethoxy | 6-chloro |
| [10] | 2-(2-oxopyrrolidin-1-yl)ethoxy | 6-chloro |
| [11] | 2-(4-pyridyloxy)ethoxy | 6-chloro |
| [12] | 3-(4-pyridyloxy)propoxy | 6-chloro |
| [13] | 3-(4-pyridyloxy)propoxy | hydrogen |
| [14] | 3-(6-methylpyrid-2-yloxy)propoxy | hydrogen |
| [15] | 3-(6-methylpyrid-2-yloxy)propoxy | 6-chloro |
| [16] | 3-(2-pyridyloxy)propoxy | hydrogen |
| [17] | 3-(2-pyridyloxy)propoxy | 6-chloro |
| [18] | 2-(6-chloropyrid-2-yloxy)ethoxy | hydrogen |
| [19] | 2-(6-chloropyrid-2-yloxy)ethoxy | 6-chloro |
| [20] | 2-cyanopyrid-4-ylmethoxy | 6-chloro |
| [21] | 2-cyanopyrid-4-ylmethoxy | hydrogen |
| [22] | 2-(N-tert-butoxycarbonyl-4-hydroxypiperidin-4-yl)ethoxy | hydrogen |
| [23] | 2-(4-hydroxytetrahydropyran-4-yl)ethoxy | hydrogen |
| [24] | 2-(4-hydroxytetrahydropyran-4-yl)ethoxy | 6-chloro |
| [25] | ethoxy | hydrogen |
| [26] | 3-(4-tert-butoxycarbonylpiperazin-1-yl)propoxy | 6-chloro |
| [27] | 3-(4-tert-butoxycarbonylpiperazin-1-yl)propoxy | hydrogen |
| [28] | 2-(4-pyridyloxy)ethoxy | hydrogen |
| [29] | N-tert-butoxycarbonylpiperidin-4-ylmethoxy | 6-chloro |
| [30] | 3-(cis-4-cyanomethyl-3,5-dimethylpiperazin-1-yl)propoxy | hydrogen |

TABLE II-continued

| | | |
|---|---|---|
| [31] | 3-(cis-3,5-dimethylpiperazin-1-yl)propoxy | hydrogen |
| [32] | 3-(4-mesylpiperazin-1-yl)propoxy | 6-chloro |
| [33] | 3-[4-(2-cyanoethyl)piperazin-1-yl]propoxy | 6-chloro |
| [34] | 3-(4-isobutyrylpiperazin-1-yl)propoxy | 6-chloro |

Notes

[1] The product gave the following characterising data; NMR Spectrum: (DMSOd$_6$ and CF$_3$CO$_2$D) 1.3(m, 12H), 2.25(m, 2H), 3.4(m, 2H), 3.8(m, 2H), 4.0(s, 3H), 4.3(t, 2H), 6.1(s, 2H), 7.0(m, 3H), 7.35(s, 1H), 8.1(s, 1H), 8.9(s, 1H); Mass Spectrum: M + H$^+$ 453.
The 3-diisopropylaminopropan-1-ol used as a starting material was prepared as described in Tet. Lett., 1994, 35, 761.

[2] The product gave the following characterising data; NMR Spectrum: (DMSOd$_6$ and CF$_3$CO$_2$D) 2.35(m, 2H), 3.5(m, 2H), 3.65(m, 4H), 3.85(m, 4H), 4.05(s, 3H), 4.35(m, 2H), 6.15(s, 2H), 7.05(d, 1H), 7.15(d, 1H), 7.4 (s, 1H), 8.15(s, 1H), 8.9(s, 1H); Mass Spectrum: M + H$^+$ 521 and 523.

[3] The product gave the following characterising data; NMR Spectrum: (DMSOd$_6$ and CF$_3$CO$_2$D) 1.4(m, 1H), 1.7(m, 3H), 1.85(m, 2H), 2.3(m, 2H), 2.95(m, 2H), 3.3(m, 2H), 3.55(m, 2H), 4.05(s, 3H), 4.3(m, 2H), 6.15 (s, 2H), 7.05(d, 1H), 7.15(d, 1H), 7.4(s, 1H), 8.15(s, 1H), 8.95(s, 1H); Mass Spectrum: M + H$^+$ 471 and 473.

[4] The product gave the following characterising data; NMR Spectrum: (DMSOd$_6$ and CF$_3$CO$_2$D) 2.3(m, 2H), 3.05(s, 3H), 3.35(m, 2H), 4.05(s, 3H), 4.35(m, 2H), 6.15(s, 2H), 7.05(d, 1H), 7.15(d, 1H), 7.35(s, 1H), 8.15 (s, 1H), 8.9(s, 1H); Mass Spectrum: M + H$^+$ 466 and 468.

[5] The product gave the following characterising data; NMR Spectrum: (DMSOd$_6$) 0.95(d, 12H), 1.85(m, 2H), 2.6(m, 2H), 3.0(m, 2H), 3.95(s, 3H), 4.15(m, 2H), 6.1(s, 2H), 6.95(d, 1H), 7.05(d, 1H), 7.15(s, 1H), 7.8(s, 1H), 8.3(s, 1H), 9.45(s, 1H); Mass Spectrum: M − H$^−$ 485 and 487.

[6] The product gave the following characterising data; NMR Spectrum: (DMSOd$_6$ and CF$_3$CO$_2$D) 2.9(s, 3H), 3.3–3.9(br s, 8H), 3.8(m, 2H), 4.0(s, 3H), 4.6(m, 2H), 6.1(s, 2H), 7.0(m, 3H), 7.45(s, 1H), 8.15(s, 1H), 8.9(s, 1H); Mass Spectrum: M + H$^+$ 438; Elemental Analysis: Found C, 61.75; H, 6.24; N, 15.6; C$_{23}$H$_{27}$N$_5$O$_4$ 0.5H$_2$O requires C, 61.87; H, 6.32; N, 15.68%.
The 1-(2-hydroxyethyl)-4-methylpiperazine used as a starting material was prepared as follows:-
A mixture of 2-bromoethanol (2.36 g), N-methylpiperazine (1.26 g), potassium carbonate (5.0 g) and ethanol (150 ml) was stirred and heated to reflux for 18 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18(s, 3H), 2.3–2.7(br m, 8H), 2.56(t, 2H), 3.61(t, 2H).

[7] The product gave the following characterising data; NMR Spectrum: (DMSOd$_6$ and CF$_3$CO$_2$D) 1.4(m, 1H), 1.7(m, 3H), 1.85(m, 2H), 3.1(m, 2H), 3.6(m, 2H), 3.7(m, 2H), 4.05(s, 3H), 4.6(m, 2H), 6.15(s, 2H), 7.05(d, 1H), 7.15(d, 1H), 7.45(s, 1H), 8.15(s, 1H), 8.95(s, 1H); Mass Spectrum: M + H$^+$ 455 and 457.

[8] The product gave the following characterising data; NMR Spectrum: (DMSOd$_6$ and CF$_3$CO$_2$D) 2.9(s, 3H), 3.3–3.9(br s, 8H), 3.75(m, 2H), 4.05 (s, 3H), 4.6(m, 2H), 6.15(s, 2H), 7.05(d, 1H), 7.15(d, 1H), 7.5(s, 1H), 8.2 (s, 1H), 8.9(s, 1H); Mass Spectrum: M + H$^+$ 472 and 474.

[9] The product gave the following characterising data; NMR Spectrum: (DMSOd$_6$ and CF$_3$CO$_2$D) 4.05(s, 3H), 4.4(m, 2H), 4.5(m, 2H), 6.05(d, 2H), 6.15(s, 2H), 6.9(d, 2H), 7.05(d, 1H), 7.15(d, 1H), 7.3(s, 1H), 8.15(s, 1H), 8.9(s, 1H); Mass Spectrum: M + H$^+$ 439 and 441.
The 2-pyrrol-1-ylethanol used as a starting material was prepared using an analogous procedure to that described in J.C.S. Chem. Comm., 1974, 931.

[10] The product gave the following characterising data; NMR Spectrum: (DMSOd$_6$ and CF$_3$CO$_2$D) 1.95(m, 2H), 2.25(t, 2H), 3.5(t, 2H), 3.65(t, 2H), 3.95(s, 3H), 4.25(t, 2H), 6.1(s, 2H), 6.95(d, 1H), 7.05(d, 1H), 7.2(s, 1H), 7.85(s, 1H), 8.3(s, 1H), 9.45(s, 1H); Mass Spectrum: M + H$^+$ 457 and 459.

[11] The product gave the following characterising data; NMR Spectrum: (DMSOd$_6$) 3.95(s, 3H), 4.5(m, 4H), 6.05(s, 2H), 6.95(d, 1H), 7.05(m, 3H), 7.25(s, 1H), 7.85(s, 1H), 8.35(s, 1H), 8.4(d, 2H), 9.5(s, 1H); Mass Spectrum: M + H$^+$ 467 and 469.
The 4-(2-hydroxyethoxy)pyridine used as a starting material was prepared according to the procedure disclosed in J. Chem. Soc. Perkin II, 1987, 1867.

[12] The product gave the following characterising data; NMR Spectrum: (DMSOd$_6$) 2.3(m, 2H), 3.9(s, 3H), 4.3(m, 4H), 6.05(s, 2H), 6.95(d, 1H), 7.0(d, 2H), 7.05(d, 1H), 7.25(s, 1H), 7.85(s, 1H), 8.3(s, 1H), 8.4(d, 2H), 9.45(s, 1H); Mass Spectrum: M + H$^+$ 481 and 483.
The 4-(3-hydroxypropoxy)pyridine used as a starting material was prepared as follows:-

Sodium hydroxide (6.66 g) was added to a mixture of 4-chloropyridine hydrochloride (10 g), 1,3-propanediol (24 ml) and DMSO (100 ml) and the mixture was stirred and heated to 100° C. for 20 hours. The mixture was concentrated by evaporation under vacuum of DMSO (about 80 ml) and the residual mixture was diluted with ice-water and extracted with ethyl acetate (4x). The organic phases were combined, dried over magnesium sulphate and evaporated. The residue was purified by column chromatography on silica using a 12:7:1 mixture of methylene chloride, ethyl acetate and methanol as eluent. There was thus obtained 4-(3-hydroxypropoxy)pyridine (3.13 g) as an oil; NMR Spectrum: (CDCl$_3$) 2.05(m, 2H), 3.0(br s, 1H), 3.85(m, 2H), 4.15(t, 2H), 6.75(d, 2H), 8.35(d, 2H); Mass Spectrum: M + H$^+$ 154.

[13] DMF was used in place of methylene chloride as the reaction solvent. The product gave the following characterising data; NMR Spectrum: (DMSOd$_6$) 2.3(m, 2H), 3.95(s, 3H), 4.3(m, 4H), 6.05(s, 2H), 6.85(m, 2H), 6.95 (d, 1H), 7.05(d, 2H), 7.2(s, 1H), 7.8(s, 1H), 8.35(s, 1H), 8.4(d, 2H), 9.5(s, 1H); Mass Spectrum: M − H$^−$ 445.

[14] The product gave the following characterising data; NMR Spectrum: (DMSOd$_6$) 2.25(m, 2H), 2.4(s, 3H), 3.95(s, 3H), 4.3(t, 2H), 4.45(t, 2H), 6.1(s, 2H), 6.65(d, 1H), 6.85(m, 3H), 6.95(d, 1H), 7.2(s, 1H), 7.6(t, 1H), 7.85(s, 1H), 8.35(s, 1H), 9.5(s, 1H); Mass Spectrum: M + H$^+$ 461.
The 2-(3-hydroxypropoxy)-6-methylpyridine used as a starting material was prepared as follows:-
Sodium hydroxide (3 g) was added to a mixture of 6-chloro-2-methylpyridine (3.3 ml), 1,3-propanediol (11 ml) and DMSO (35 ml) and the mixture was stirred and heated to 100° C. for 20 hours. The mixture was cooled to ambient temperature, diluted with ice-water and extracted with ethyl acetate (3x). The organic phases were combined, dried over magnesium sulphate and evaporated. The residue was purified by column chromatography on silica using a 4:1 mixture of methylene chloride and ethyl acetate as eluent. There was thus obtained 2-(3-hydroxypropoxy)-6-methylpyridine (3.5 g) as an oil; NMR Spectrum: (CDCl$_3$) 1.95(m, 2H), 2.45(s, 3H), 3.7(m, 2H), 4.1(br s, 1H), 4.5(t, 2H), 6.55(d, 1H), 6.75(d, 1H), 7.45 (t, 1H).

[15] The product gave the following characterising data; NMR Spectrum: (DMSOd$_6$) 2.25(m, 2H), 2.4(s, 3H), 3.95(s, 3H), 4.3(t, 2H), 4.45(t, 2H), 6.1(s, 2H), 6.65(d, 1H), 6.85(m, 1H), 6.95(d, 1H), 7.1(d, 1H), 7.25(s, 1H), 7.6(t, 1H), 7.85(s, 1H), 8.35(s, 1H), 9.5(s, 1H); Mass Spectrum: M + H$^+$ 495 and 497.

[16] DMF was used in place of methylene chloride as the reaction solvent. The product gave the following characterising data; NMR Spectrum: (DMSOd$_6$) 2.2(m, 2H), 3.95(s, 3H), 4.1(t, 2H), 4.2(t, 2H), 6.05(s, 2H), 6.2(t, 1H), 6.4(d, 1H), 6.9(m, 2H), 6.95(d, 1H), 7.15(s, 1H), 7.4(m, 1H), 7.7(d, 1H), 7.85(s, 1H), 8.4(s, 1H), 9.6(s, 1H); Mass Spectrum: M + H$^+$ 447.
The 2-(3-hydroxypropoxy)pyridine used as a starting material was prepared by the reaction of 2-chloropyridine and 1,3-propanediol using an analogous procedure to that described in Note [14] immediately above.

[17] DMF was used in place of methylene chloride as the reaction solvent. The product gave the following characterising data; NMR Spectrum: (DMSOd$_6$) 2.2(m, 2H), 3.95(s, 3H), 4.1(t, 2H), 4.2(t, 2H), 6.1(s, 2H), 6.2(t, 1H), 6.4(d, 1H), 6.95(d, 1H), 7.1(d, 1H), 7.2(s, 1H), 7.4(m, 1H), 7.65(d, 1H), 7.85(s, 1H), 8.35(s, 1H), 9.5(s, 1H); Mass Spectrum: M + H$^+$ 481 and 483.

[18] DMF was used in place of methylene chloride as the reaction solvent. The reaction product was purified by column chromatography on silica (Isolute SCX column) using an 18:1 mixture of methylene chloride and a saturated methanolic ammonia solution as eluent. The product so obtained gave the following characterising data; NMR Spectrum: (DMSOd$_6$) 3.95(s, 3H), 4.5(m, 2H), 4.65(m, 2H), 6.05(s, 2H), 6.9(m, 4H), 7.15(d, 1H), 7.25 (s, 1H), 7.8(m, 2H), 8.4(s, 1H), 9.5(s, 1H); Mass Spectrum: M + H$^+$ 467 and 469.
The 6-chloro-2-(2-hydroxyethoxy)pyridine used as a starting material was prepared as follows:-
Sodium hydride (50% dispersion in mineral oil; 0.48 g) was added portionwise to a stirred mixture of 2-tetrahydropyran-2-yloxyethanol (1.36 ml) and DMF (5 ml) and the mixture was stirred at ambient temperature for 30 minutes and then heated to 80° C. for 15 minutes. The mixture was cooled to ambient temperature. 2,6-Dichloropyridine (1.48 g) was added and the resultant mixture was heated to 80° C. for 16 hours. The mixture was cooled to ambient temperature and partitioned between ethyl acetate and water. The organic phase was washed with brine, dried over magnesium sulphate and evaporated. The residue was purified by column chromatography on silica using methylene chloride as eluent. There was thus obtained 2-chloro-6-(2-tetrahydropyran-2-yloxyethoxy)pyridine (2 g) as an oil; NMR Spectrum: (CDCl$_3$) 1.4–1.9(m, 6H), 3.5(m, 1H), 3.75(m, 1H), 3.85(m, 1H), 4.05(m, 1H), 4.5(m, 2H), 4.7(m, 1H), 6.7(d, 1H), 6.9(d, 1H), 7.5(t, 1H).

TABLE II-continued

A mixture of the material so obtained, acetic acid (20 ml), water (4 ml) and THF (8 ml) was stirred and heated to 80° C. for 5 hours. The solvent was evaporated and the residue was purified by column chromatography on silica using a 3:2 mixture of petroleum ether (b.p. 40–60° C.) and diethyl ether as eluent. There was thus obtained 6-chloro-2-(2-hydroxyethoxy)pyridine (0.98 g) as an oil; NMR Spectrum: (DMSOd$_6$ and CF$_3$CO$_2$D) 2.5(br s, 1H), 3.9(m, 2H), 4.45 (m, 2H), 6.7(d, 1H), 6.9(d, 1H), 7.5(t, 1H); Mass Spectrum: M + H$^+$ 174 and 176.

[19] The reaction product was purified by column chromatography on silica (Isolute SCX column) using an 18:1 mixture of methylene chloride and a saturated methanolic ammonia solution as eluent. The product so obtained gave the following characterising data; NMR Spectrum: (DMSOd$_6$) 4.05(s, 3H), 4.5(m, 2H), 4.65(m, 2H), 6.1(s, 2H), 6.9(t, 2H), 7.05(d, 1H), 7.15(d, 1H), 7.3(s, 1H), 7.8(t, 1H), 7.85(s, 1H), 8.35(s, 1H), 9.5(br s, 1H); Mass Spectrum: M + H$^+$ 501 and 503.

[20] The product gave the following characterising data; NMR Spectrum: (DMSOd$_6$ and CF$_3$CO$_2$D) 4.05(s, 3H), 5.55(s, 2H), 6.15(s, 2H), 7.05(d, 1H), 7.15(d, 1H), 7.35(s, 1H), 7.85(d, 1H), 8.14(s, 1H), 8.18(s, 1H), 8.85 (d, 1H), 8.9(s, 1H); Mass Spectrum: M + H$^+$ 462 and 464.

The 2-cyano-4-hydroxymethylpyridine used as a starting material was prepared as follows:-

Using an analogous procedure to that disclosed in J. Het. Chem., 1993, 30, 631, 4-hydroxymethylpyridine was converted into 4-(tert-butyldimethylsilyloxymethyl)pyridine-2-carbonitrile.

A mixture of the material so obtained (3.37 g) tert-butylammonium fluoride (1M solution in THF; 24 ml) and THF (20 ml) was stirred at ambient temperature for 1 hour. The mixture was evaporated and the residue was partitioned between ethyl acetate and a saturated aqueous ammonium chloride solution. The organic phase was washed with water and with brine, dried over magnesium sulphate and evaporated. The residue was purified by column chromatography on silica using increasingly polar mixtures of petroleum ether (b.p. 40–60° C.) and ethyl acetate as eluent. There was thus obtained 2-cyano-4-hydroxymethylpyridine as a solid (1.37 g); NMR Spectrum: (CDCl$_3$) 2.25(br s, 1H), 4.85(s, 2H), 7.55(d, 1H), 7.75(s, 1H), 8.7(d, 1H).

[21] DMF was used in place of methylene chloride as the reaction solvent. The product gave the following characterising data; NMR Spectrum: (DMSOd$_6$ and CF$_3$CO$_2$D) 4.0(s, 3H), 5.45(s, 2H), 6.0(s, 2H), 6.85–7.0(m, 3H), 7.3(s, 1H), 7.85(d, 1H), 7.9(s, 1H), 8.1(s, 1H), 8.4(s, 1H), 8.8(d, 1H); Mass Spectrum: M + H$^+$ 428.

[22] The product gave the following characterising data; NMR Spectrum: (CDCl$_3$) 1.45(s, 9H), 1.6(m, 4H), 2.1(m, 2H), 3.2(s, 1H), 3.25(m, 2H), 3.8(m, 2H), 4.0(s, 3H), 4.4(t, 2H), 6.05(s, 2H), 6.7(d, 1H), 6.9(t, 1H), 7.0 (s, 1H), 7.05(s, 1H), 7.25(s, 1H), 7.75(d, 1H), 8.7(s, 1H); Mass Spectrum: M + H$^+$ 539.

The N-tert-butoxycarbonyl-4-hydroxy-4-(2-hydroxyethyl)piperidine used as a starting material was prepared as follows:-

A mixture of tert-butyl 4-oxopiperidine-1-carboxylate (5 g), ethyl bromoacetate (4.17 ml), zinc powder (2.46 g) and THF (40 ml) was stirred and heated to reflux to initiate reaction. Once the reaction had started, the temperature of the reaction mixture was controlled by the occasional immersion of the mixture in an ice bath. After 2 hours the reaction mixture was evaporated and the residue was partitioned between ethyl acetate and water. The organic phase was washed with brine, dried over magnesium sulphate and evaporated. The residue was purified by column chromatography on silica using a 6:1 mixture of methylene chloride and ethyl acetate as eluent. There was thus obtained tert-butyl 4-ethoxycarbonylmethyl-4-hydroxypiperidine-1-carboxylate as an oil (6.5 g); NMR Spectrum: (CDCl$_3$) 1.3(t, 3H), 1.45(s, 9H), 1.5(m, 2H), 1.7(m, 2H), 2.5(s, 2H), 3.2 (m, 2H), 3.6(s, 1H), 3.85(br s, 2H), 4.2(m, 2H).

A solution of the material so obtained in THF (30 ml) was added to a stirred suspension of lithium aluminium hydride (0.86 g) in THF (45 ml) which was cooled in an ice-bath to 0° C. After completion of the addition, the reaction mixture was heated to reflux for 2 hours. The mixture was cooled to 0° C. and a concentrated (40%) aqueous sodium hydroxide solution was added. The mixture was filtered and the filtrate was concentrated by partial evaporation. The residue was extracted with methylene chloride and the extract was dried over magnesium sulphate and evaporated. There was thus obtained N-tert-butoxycarbonyl-4-hydroxy-4-(2-hydroxyethyl) piperidine as an oil; NMR Spectrum: (CDCl$_3$) 1.45(s, 9H), 1.5(m, 2H), 1.7(m, 2H), 1.75(m, 2H), 2.2(br s, 1H), 2.9(s, 1H), 3.2(m, 2H), 3.75(m, 2H), 3.95(m, 2H).

[23] The product gave the following characterising data; NMR Spectrum: (DMSOd$_6$ and CF$_3$CO$_2$D) 1.5(m, 2H), 1.65(m, 2H), 2.0(m, 2H), 3.65(m, 4H), 4.0(s, 3H), 4.35(t, 2H), 6.05(s, 2H), 7.0(m, 3H), 7.35(s, 1H), 8.05(s, 1H), 8.85(s, 1H); Mass Spectrum: M + H$^+$ 440.

The 4-hydroxy-4-(2-hydroxyethyl)tetrahydropyran used as a starting material was prepared as follows:-

Using analogous procedures to those described in Note [22] immediately above for the conversion of tert-butyl 4-oxopiperidine-1-carboxylate into N-tert-butoxycarbonyl-4-hydroxy-4-(2-hydroxyethyl)piperidine, tetrahydropyran-4-one was reacted with ethyl bromoacetate to give ethyl 2-(4-hydroxytetrahydropyran-4-yl)acetate; NMR Spectrum: (CDCl$_3$) 1.3(t, 3H), 1.65(m, 4H), 2.5(s, 2H), 4.6(s, 1H), 3.75(m, 2H), 3.85(m, 2H), 4.2(q, 2H); which, in turn, was reduced to give 4-hydroxy-4-(2-hydroxyethyl)tetrahydropyran; NMR Spectrum: (CDCl$_3$) 1.7(m, 4H), 1.8(m, 2H), 2.25(br s, 1H), 2.9(br s, 1H), 3.8(m, 4H), 3.95(m, 2H).

[24] The product gave the following characterising data; NMR Spectrum: (DMSOd$_6$ and CF$_3$CO$_2$D) 1.5(m, 2H), 1.65(m, 2H), 2.0(m, 2H), 3.6(m, 4H), 4.0(m, 5H), 6.15(s, 2H), 7.05(d, 1H), 7.15(d, 1H), 7.35(s, 1H), 8.1(s, 1H), 8.9(s, 1H); Mass Spectrum: M + H$^+$ 474 and 476.

[25] Chloroform was used in place of methylene chloride as the reaction solvent. The product gave the following characterising data; NMR Spectrum: (DMSOd$_6$) 1.45(t, 3H), 3.95(s, 3H), 4.2(q, 2H), 6.05(s, 2H), 6.9(m, 2H), 6.95(d, 1H), 7.15(s, 1H), 7.8(s, 1H), 8.35(s, 1H), 9.5(s, 1H); Mass Spectrum: M + H$^+$ 340.

[26] The product gave the following characterising data; NMR Spectrum: (DMSOd$_6$ and CF$_3$CO$_2$D) 1.4(s, 9H), 2.05(m, 2H), 2.45(m, 4H), 2.6(m, 2H), 3.35(m, 4H), 3.95(m, 3H), 4.2(m, 2H), 6.1(s, 2H), 6.95(d, 1H), 7.05 (d, 1H), 7.2(s, 1H), 7.85(s, 1H), 8.3(s, 1H); Mass Spectrum: M + H$^+$ 572 and 574.

The 1-(tert-butoxycarbonyl)-4-(3-hydroxypropyl)piperazine used as a starting material was prepared as follows using an analogous procedure to that described in European Patent Application No. 0388309:-

A mixture of 3-bromopropanol (25 ml), 1-(tert-butoxycarbonyl)piperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil.

[27] The product gave the following characterising data; NMR Spectrum: (DMSOd$_6$) 1.4(s, 9H), 1.95(m, 2H), 2.35(m, 4H), 2.45–2.6(m, 6H), 3.95(s, 3H), 4.2(t, 2H), 6.05(s, 2H), \6.8–7.0(m, 3H), 7.2(s, 1H), 7.8(s, 1H), 8.35 (s, 1H), 9.5(s, 1H); Mass Spectrum: M + H$^+$ 538.

[28] The free base form of the reaction product was treated with a 6 M solution of hydrogen chloride in diethyl ether to give the dihydrochloride salt which gave the following characterising data; NMR Spectrum: (DMSOd$_6$ and CF$_3$CO$_2$D) 4.0(s, 3H), 4.68(br s, 2H), 4.9(br s, 2H), 6.1(s, 2H), 7.0(2s, 2H), 7.5(s, 1H), 7.7(d, 2H), 8.2(s, 1H), 8.85(d, 2H), 8.9(s, 1H); Mass Spectrum: M + H$^+$ 433.

[29] DMF was used in place of methylene chloride as the reaction solvent. The product gave the following characterising data; Mass Spectrum: M + H$^+$ 543 and 545.

[30] DMF was used in place of methylene chloride as the reaction solvent and the reaction mixture was stirred at ambient temperature for 16 hours. The product gave the following characterising data; NMR Spectrum: (DMSOd$_6$ and CF$_3$CO$_2$D) 1.12(s, 3H), 1.13(s, 3H), 2.3(m, 2H), 2.8(m, 4H), 3.3(m, 2H), 3.65(d, 2H), 4.0(s, 3H), 4.05(s, 2H), 4.35(m, 2H), 6.1(s, 2H), 7.0(m, 3H), 7.35(s, 1H), 8.1(s, 1H), 8.9(s, 1H); Mass Spectrum: M + H$^+$ 505.

The cis-3,5-dimethyl-4-cyanomethyl-1-(3-hydroxypropyl)piperazine used as a starting material was prepared as follows:-

A mixture of cis-2,6-dimethylpiperazine (4.3 g), 3-bromopropanol (5.2 g), potassium carbonate (15.6 g) and acetonitrile (30 ml) was stirred and heated to 80° C. for 2.5 hours. The mixture was filtered and the filtrate was evaporated. The residue was purified by column chromatography on silica using a 21:1 mixture of methylene chloride and a saturated methanolic ammonia solution as eluent. There was thus obtained cis-3,5-dimethyl-1-(3-hydroxypropyl)piperazine (5.84 g).

A mixture of a portion (2.5 g) of the material so obtained, trityl chloride (4.25 g), 4-dimethylaminopyridine (0.018 g), triethylamine (2.2 ml) and DMF (40 ml) was stirred and heated to 40° C. for 5 hours. The mixture was evaporated and the residue was partitioned between ethyl acetate and water. The organic phase was washed with water and with brine, dried over magnesium sulphate and evaporated to give cis-3,5-dimethyl-1-(3-trityloxypropyl)piperazine as a foam (5 g); NMR Spectrum: (DMSOd$_6$ and CD$_3$CO$_2$D) 1.18(s, 3H), 1.2(s, 3H), 1.7(m, 2H), 1.95(m, 2H), 2.45(m, 2H), 2.9(m, 2H), 3.05(t, 2H), 3.15(m, 2H), 7.2–7.5(m, 15H).

A mixture of the material so obtained, 2-bromoacetonitrile (0.925 ml), potassium carbonate (5 g), tri-n-butylammonium iodide (0.44 g) and DMF (12 ml) was stirred and heated to 40° C. for 6 hours. The mixture was filtered and the filtrate was evaporated. The residue was partitioned between ethyl acetate and water. The organic phase was washed with water and with brine, dried over magnesium sulphate and evaporated. The material so obtained was purified by column chromatography on silica a 17:3 mixture of methylene chloride and methanol as eluent. There was thus obtained cis-3,5-dimethyl-4-cyanomethyl-1-(3-trityloxypropyl)piperazine (2.7 g) as a gum.

TABLE II-continued

A mixture of cis-3,5-dimethyl-4-cyanomethyl-1-(3-trityloxypropyl)piperazine (3 g), a 1N aqueous hydrochloride acid solution (20 ml) and methanol (100 ml) was stirred at ambient temperature for 17 hours. The solvent was evaporated and the residual aqueous solution was basified to pH 11 by the addition of a saturated aqueous sodium carbonate solution. The mixture was extracted with ethyl acetate and the organic phase was washed with water and with brine, dried and evaporated. The material so obtained was purified by column chromatography on silica using a 9:1 mixture of methylene chloride and methanol as eluent. There was thus obtained cis-3,5-dimethyl-4-cyanomethyl-1-(3-hydroxypropyl)piperazine as a gum (0.4 g); NMR Spectrum: (CDCl$_3$) 1.07(s, 3H), 1.09(s, 3H), 1.75(m, 2H), 1.9(t, 2H), 2.55(t, 2H), 2.7(m, 2H), 2.95(d, 2H), 3.75(s, 2H), 3.8(t, 2H).

[31] The reaction mixture was stirred at ambient temperature for 5 hours. The product gave the following characterising data; NMR Spectrum: (DMSOd$_6$ and CF$_3$CO$_2$D) 1.28(s, 3H), 1.3(s, 3H), 2.35(m, 2H), 3.05(t, 2H), 3.4(m, 2H), 3.65(m, 2H), 3.9(d, 2H), 4.0(s, 3H), 4.3(t, 2H), 6.1(s, 2H), 7.0(m, 3H), 7.4(s, 1H), 8.1(s, 1H), 8.9(s, 1H); Mass Spectrum: M + H$^+$ 466.

[32] The reaction mixture was stirred at ambient temperature for 1 hour. The product gave the following characterising data; NMR Spectrum: (DMSOd$_6$ and CF$_3$CO$_2$D) 2.3(m, 2H), 3.05(s, 3H), 3.1–3.3(m, 4H), 3.4(t, 2H), 3.6–3.9(m, 4H), 4.05(s, 3H), 4.35(t, 2H), 6.15(s, 2H), 7.1(d, 1H), 7.2(d, 1H), 7.4(s, 1H), 8.15(s, 1H), 8.9(s, 1H); Mass Spectrum: M + H$^+$ 550.
The 1-(3-hydroxypropyl)-4-mesylpiperazine used as a starting material was prepared as follows:-
Mesyl chloride (0.966 ml) was added dropwise to a stirred mixture of 1-benzylpiperazine (2 g), triethylamine (1.74 ml) and methylene chloride (30 ml) which was cooled to 0° C. The reaction mixture was allowed to warm to ambient temperature and stirred for 1 hour. The mixture was partitioned between methylene chloride and water. The organic phase was washed with water and with brine, dried over magnesium sulphate and evaporated. The residue was purified by column chromatography on silica using a 7:3 mixture of methylene chloride and ethyl acetate as eluent. There was thus obtained 1-benzyl-4-mesylpiperazine (2.5 g) as a solid; NMR Spectrum: (CDCl$_3$) 2.6(m, 4H), 2.8(s, 3H), 3.3(m, 4H), 3.55(s, 2H), 7.3(m, 5H); Mass Spectrum: M + H$^+$ 255.
A mixture of the material so obtained, cyclohexene (30 ml), palladium oxide on charcoal catalyst (20%; 0.5 g) and ethanol (70 ml) was stirred and heated to 80° C. for 4 hours. The catalyst was removed by filtration and the solvent was evaporated to give 1-mesylpiperazine (1.58 g) as a solid; NMR Spectrum: (CDCl$_3$) 2.8(s, 3H), 3.0(m, 4H), 3.2(m, 4H); Mass Spectrum: M + H$^+$ 165.
A mixture of the material so obtained, 3-bromopropanol (1.13 ml), potassium carbonate (1.73 g) and acetonitrile (10 ml) was stirred and heated to 40° C. for 4 hours and then to 70° C. for 2 hours. The excess of potassium carbonate was removed by filtration and the filtrate was evaporated. The residue was purified by column chromatography on silica using increasingly polar solvent mixtures of methylene chloride and methanol as eluent. There was thus obtained 1-(3-hydroxypropyl)-4-mesylpiperazine (1.95 g) as a solid; NMR Spectrum: (CDCl$_3$) 1.8(m, 2H), 2.6–2.7(m, 6H), 2.8(s, 3H), 3.3(m, 4H), 3.8(t, 2H), 4.5(br s, 1H); Mass Spectrum: M + H$^+$ 223.

[33] The reaction mixture was stirred at ambient temperature for 5 hours. The product gave the following characterising data; NMR Spectrum: (DMSOd$_6$ and CF$_3$CO$_2$D) 2.3(m, 2H), 2.95(t, 2H), 3.2(t, 2H), 3.4(t, 2H), 2.9–3.7(br m, 8H), 4.05(s, 3H), 4.35(t, 2H), 6.2(s, 2H), 7.05(d, 1H), 7.15(d, 1H), 7.4(s, 1H), 8.15(s, 1H), 8.9(s, 1H); Mass Spectrum: M + H$^+$ 525.
The 3-[4-(3-hydroxypropyl)piperazin-1-yl]propionitrile used as a starting material was prepared as follows:-
Acrylonitrile (0.827 ml) was added to a mixture of 1-benzylpiperazine (2 g), methylene chloride (20 ml) and methanol (20 ml) and the resultant mixture was stirred at ambient temperature for 24 hours. The mixture was evaporated and the residue was purified by column chromatography on silica using a 97:3 mixture of methylene chloride and mthanol as eluent. There was thus obtained 3-(4-benzylpiperazin-1-yl)propionitrile (2.63 g) as a liquid; NMR Spectrum: (CDCl$_3$) 2.5(m, 10H), 2.7(t, 2H), 3.55(s, 2H), 7.3(m, 5H); Mass Spectrum: M + H$^+$ 230.
The material so obtained was treated according to the procedures described in the last two paragraphs of the portion of Note [32] immediately above that is concerned with the preparation of starting materials. There was thus obtained 3-[4-(3-hydroxypropyl)piperazin-1-yl]propionitrile as a liquid (1.36 g); NMR Spectrum: (CDCl$_3$) 1.7(m, 2H), 2.3–2.7(m, 14H), 3.8(t, 2H); Mass Spectrum: M + H$^+$ 198.

[34] The reaction mixture was stirred at ambient temperature for 5 hours. The product gave the following characterising data; NMR Spectrum: (DMSOd$_6$ and CF$_3$CO$_2$D) 0.95(d, 6H), 2.05(t, 2H), 2.45(m, 4H), 2.6(m, 2H), 2.85(m, 1H), 3.5(m, 4H), 3.95(s, 3H), 4.2(t, 2H), 6.05(s, 2H), 6.9(d, 1H), 7.05(d, 1H), 7.2(s, 1H), 7.85(s, 1H), 8.3(s, 1H); Mass Spectrum: M + H$^+$ 542 and 544.

The 1-(3-hydroxypropyl)-4-isobutyrylpiperazine used as a starting material was prepared as follows:

Isobutyryl chloride (1.3 ml) was added dropwise to a stirred mixture of 1-benzylpiperazine (2 g), triethylamine (1.74 ml) and methylene chloride (30 ml) which was cooled to 0° C. The reaction mixture was allowed to warm to ambient temperature and stirred for 1 hour. The mixture was partitioned between methylene chloride and water. The organic phase was washed with water and with brine, dried over magnesium sulphate and evaporated. The residue was purified by column chromatography on silica using a 3:2 mixture of methylene chloride and ethyl acetate as eluent. There was thus obtained 1-benzyl-4-isobutyrylpiperazine (2.6 g) as an oil; NMR Spectrum: (DMSOd$_6$ and CF$_3$CO$_2$D) 1.15 (d, 6H), 2.45 (m, 4H), 2.8 (m, 1H), 3.5 (m, 4H), 3.65 (m, 2H), 7.3 (m, 5H); Mass Spectrum: M+H$^+$ 247.

The material so obtained was treated according to the procedures described in the last two paragraphs of the portion of Note [32] immediately above that is concerned with the preparation of starting materials. There was thus obtained 1-(3-hydroxypropyl)-4-isobutyrylpiperazine as a liquid (1.7 g); NMR Spectrum: (CDCl$_3$) 1.1 (d, 6H), 1.7 (m, 2H), 2.45 (m, 4H), 2.6 (t, 2H), 2.75 (m, 1H), 3.5 (m, 2H), 3.6 (m, 2H), 3.8 (t, 2H), 4.7 (br s, 1H); Mass Spectrum: M+H$^+$ 215.

EXAMPLE 9

7-(2-homopiperidin-1-ylethoxy)-4-(2,3-methylenedioxyanilino)-6-methoxyquinazoline A mixture of 7-(2-bromoethoxy)-4-(2,3-methylenedioxyanilino)-6-methoxyquinazoline (0.48 g) homopiperidine (0.322 ml), sodium iodide (0.002 g), DMF (5 ml) and acetonitrile (6 ml) was stirred and heated to 45° C. for 5 hours. The mixture was evaporated and the residue was partitioned between methylene chloride and water. The organic phase was washed with brine, dried over magnesium sulphate and evaporated. The residue was purified by column chromatography on silica using a 19:1 mixture of methylene chloride and a saturated methanolic ammonia solution as eluent. The material so obtained was triturated under diethyl ether to give the title compound as a solid (0.4 g); NMR Spectrum: (DMSOd$_6$ and CF$_3$CO$_2$D) 1.65 (m, 4H), 1.9 (m, 4H), 3.35 (m, 2H), 3.55 (m, 2H), 3.7 (m, 2H), 4.0 (s, 3H), 4.6 (m, 2H), 6.1 (s, 2H), 7.0 (m, 3H), 7.45 (s, 1H), 8.15 (s, 1H), 8.9 (s, 1H); Mass Spectrum: M+H$^+$ 437.

The 7-(2-bromoethoxy)-4-(2,3-methylenedioxyanilino)-6-methoxyquinazoline used as a starting material was prepared as follows:

1,1'-(Azodicarbonyl)dipiperidine (6 g) was added to a stirred mixture of 7-hydroxy-4-(2,3-methylenedioxyanilino)-6-methoxyquinazoline (3 g), 2-bromoethanol (1 ml), tributylphosphine (5.9 ml) and chloroform (300 ml) which was heated to 40° C. The mixture was heated to 40° C. for 10 minutes and then stirred at ambient temperature for 2 hours. The mixture was evaporated and the residue was purified by column chromatography on silica using a 11:9 mixture of methylene chloride and acetonitrile as eluent. There was thus obtained 7-(2-bromoethoxy)-4-(2,3-methylenedioxyanilino)-6-methoxyquinazoline (1.8 g); NMR Spectrum: (DMSOd$_6$) 3.9 (t, 2H), 3.95 (s, 3H), 4.55 (t, 2H), 6.05 (s, 2H), 6.9 (m, 3H), 7.2 (s, 1H), 7.9 (s, 1H), 8.4 (s, 1H), 9.65 (br s, 1H).

EXAMPLE 10

Using an analogous procedure to that described in Example 9, the appropriate 7-haloalkoxyquinazoline was reacted with the appropriate amine to give the compounds described in Table III. Unless otherwise stated, each compound described in Table III was obtained as the free base.

TABLE III

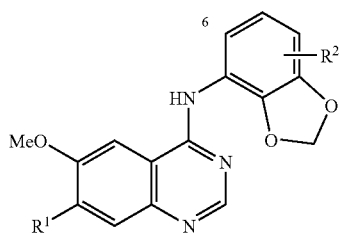

| Compound No. & Note | R¹ | R² |
|---|---|---|
| [1] | 2-pyrrolidin-1-ylethoxy | hydrogen |
| [2] | 2-piperidinoethoxy | hydrogen |
| [3] | 3-homopiperidin-1-ylpropoxy | hydrogen |
| [4] | 3-(cis-3,5-dimethylpiperazin-1-yl)propoxy | 6-chloro |
| [5] | 3-(4-hydroxypiperidin-1-yl)propoxy | 6-chloro |
| [6] | 3-[N,N-di-(2-hydroxyethyl)amino]propoxy | 6-chloro |

Notes

[1] 7-(2-Bromoethoxy)-4-(2,3-methylenedioxyanilino)-6-methoxyquinazoline was used as a starting material, DMF was used as the sole reaction solvent and the reaction mixture was warmed to 27° C. for 4 hours. The product gave the following characterising data; NMR Spectrum: (DMSOd$_6$ and CF$_3$CO$_2$D) 1.9(m, 2H), 2.1(m, 2H), 3.2(m, 2H), 3.7(m, 2H), 3.75(m, 2H), 4.0(s, 3H), 4.55(m, 2H), 6.1(s, 2H), 7.0(m, 3H), 7.45(s, 1H), 8.15(s, 1H), 8.9(d, 1H); Mass Spectrum: M − H⁻ 407.

[2] 7-(2-Bromoethoxy)-4-(2,3-methylenedioxyanilino)-6-methoxyquinazoline was used as a starting material, DMF was used as the sole reaction solvent and the reaction mixture was warmed to 30° C. for 3.5 hours. The product gave the following characterising data; NMR Spectrum: (DMSOd$_6$ and CF$_3$CO$_2$D) 1.4(m, 1H), 1.7(m, 3H), 1.9(m, 2H), 3.1(t, 2H), 3.6(m, 2H), 3.65(m, 2H), 4.05(s, 3H), 4.6(t, 2H), 6.1(s, 2H), 7.0(m, 3H), 7.4(s, 1H), 8.15(s, 1H), 8.9(s, 1H); Mass Spectrum: M + H⁺ 423.

[3] The product gave the following characterising data; NMR Spectrum: (DMSOd$_6$ and CF$_3$CO$_2$D) 1.6(m, 4H), 1.8(m, 4H), 2.3(m, 2H), 3.2(m, 2H), 3.3(m, 2H), 3.45(m, 2H), 4.0(s, 3H), 4.3(t, 2H), 6.1(s, 2H), 7.0(m, 3H), 7.4(s, 1H), 8.1(s, 1H), 8.9(s, 1H); Mass Spectrum: M + H⁺ 451.
The 7-(3-chloropropoxy)-4-(2,3-methylenedioxyanilino)-6-methoxyquinazoline used as a starting material was prepared as follows:-
A mixture of 7-hydroxy-4-(2,3-methylenedioxyanilino)-6-methoxyquinazoline (2 g) and DMF (40 ml) was warmed until the starting material was completely dissolved. The solution was cooled to ambient temperature and 3-chloropropyl bromide (0.826 ml), tetrabutylammonium iodide (0.237 g) and caesium carbonate (4.2 g) were added in turn. The resultant mixture was stirred at ambient temperature for 20 hours. Water was added and the mixture was extracted with ethyl acetate (2x). The combined organic phases were washed with water and with brine, dried over magnesium sulphate and evaporated. The residue was purified by column chromatography on silica using a 24:1 mixture of methylene chloride and methanol as eluent. There was thus obtained 7-(3-chloropropoxy)-4-(2,3-methylenedioxyanilino)-6-methoxyquinazoline (1.8 g); NMR Spectrum: (DMSOd$_6$ and CF$_3$CO$_2$D) 2.3(m, 2H), 3.85(t, 2H), 4.0(s, 3H), 4.35(t, 2H), 6.1(s, 2H), 7.0(m, 3H), 7.35(s, 1H), 8.1(s, 1H), 8.85(s, 1H); Mass Spectrum: M + H⁺ 388 and 390.

[4] Acetonitrile was used as the sole reaction solvent and the reaction mixture was warmed to 60° C. for 5 hours. The product gave the following characterising data; NMR Spectrum: (DMSOd$_6$ and CF$_3$CO$_2$D) 1.29(s, 3H), 1.31(s, 3H), 2.35(m, 2H), 3.0(m, 2H), 3.4(m, 2H), 3.65(m, 2H), 3.85 (m, 2H), 4.0(s, 3H), 4.35(m, 2H), 6.15(s, 2H), 7.05(d, 1H), 7.15(d, 1H), 7.4(s, 1H), 8.15(s, 1H), 8.9(s, 1H); Mass Spectrum: M − H⁻ 498 and 500.
The 7-(3-bromopropoxy)-4-(6-chloro-2,3-methylenedioxyanilino)-6-methoxyquinazoline used as a starting material was prepared as follows:-
1,1'-(Azodicarbonyl)dipiperidine (0.725 g) was added to a stirred mixture of 4-(6-chloro-2,3-methylenedioxyanilino)-7-hydroxy-6-methoxyquinazoline (0.5 g), 3-bromopropanol (0.234 ml), tributylphosphine (0.715 ml), methylene chloride (50 ml) and THF (20 ml) and the reaction mixture was stirred at ambient temperature for 1 hour. Second portions of tributylphosphine (0.357 ml) and 1,1'-(azodicarbonyl)dipiperidine (0.362 g) were added and the reaction mixture was stirred for another 2 hours. The resultant mixture was evaporated and the residue was purified by column chromatography on silica using a 7:3 mixture of methylene chloride and acetonitrile as eluent. There was thus obtained 7-(3-bromopropoxy)-4-(6-chloro-2,3-methylenedioxyanilino)-6-methoxyquinazoline as a solid (0.3 g); NMR Spectrum: (DMSOd$_6$) 2.35(m, 2H), 3.7(t, 2H), 3.95(s, 3H), 4.25(t, 2H), 6.1(s, 2H), 6.95(d, 1H), 7.05(d, 1H), 7.2(s, 1H), 7.85(s, 1H), 8.3(s, 1H), 9.5(s, 1H); Mass Spectrum: M + H⁺ 466.

[5] The reaction mixture was heated to reflux for 16 hours. The product gave the following characterising data; NMR Spectrum: (DMSOd$_6$) 1.4(m, 2H), 1.75(m, 2H), 1.95(m, 2H), 2.0(m, 2H), 2.4(t, 2H), 2.75(m, 2H), 3.5 (m, 1H), 3.95(s, 3H), 4.2(t, 2H), 4.55(s, 1H), 6.1(s, 2H), 6.95(d, 1H), 7.1 (d, 1H), 7.2(s, 1H), 7.85(s, 1H), 8.35(s, 1H), 9.5(s, 1H); Mass Spectrum: M + H⁺ 487.
The 4-(6-chloro-2,3-methylenedioxyanilino)-7-(3-chloropropoxy)-6-methoxyquinazoline used as a starting material was prepared as follows:-
A mixture of 4-(6-chloro-2,3-methylenedioxyanilino)-7-hydroxy-6-methoxyquinazoline (1.5 g), 3 chloropropyl bromide (0.54 ml), potassium carbonate (1.5 g) and DMF (20 ml) was stirred at ambient temperature for 16 hours. The mixture was partitioned between ethyl acetate and water. The organic phase was washed with water and with brine, dried over magnesium sulphate and evaporated. The residue was triturated under diethyl ether and the resultant solid was isolated, washed with diethyl ether and dried under vacuum. There was thus obtained 4-(6-chloro-2,3-methylenedioxyanilino)-7-(3-chloropropoxy)-6-methoxyquinazoline (1.34 g); NMR Spectrum: (DMSOd$_6$) 2.25(m, 2H), 3.85(t, 2H), 3.95(t, 3H), 4.3(t, 2H), 6.1(s, 2H), 6.95(d, 1H), 7.05(d, 1H), 7.15(s, 1H), 7.85(s, 1H), 8.35(s, 1H), 9.5(br s, 1H).

[6] 4-(6-Chloro-2,3-methylenedioxyanilino)-7-(3-chloropropoxy)-6-methoxyquinazoline was used as a starting material and the reaction mixture was heated to reflux for 16 hours. The product gave the following characterising data; NMR Spectrum: (DMSOd$_6$) 1.9(m, 2H), 2.7(m, 2H), 3.35–3.5(m, 8H), 3.95(s, 3H), 4.2(t, 2H), 4.35(t, 2H), 6.1(s, 2H), 6.95(d, 1H), 7.1(d, 1H), 7.2(s, 1H), 7.85(s, 1H), 8.3(s, 1H), 9.5(s, 1H); Mass Spectrum: M + H⁺ 491.

EXAMPLE 11

4-(6-chloro-2,3-methylenedioxyanilino)-6-methoxy-7-(3-piperazin-1-ylpropoxy)quinazoline dihydrochloride salt A mixture of 7-[3-(4-tert-butoxycarbonylpiperazin-1-yl) propoxy]-4-(6-chloro-2,3-methylenedioxyanilino)-6-methoxyquinazoline (0.286 g), trifluoroacetic acid (0.5 ml) and methylene chloride (6 ml) was stirred at ambient temperature for 3 hours. The solvent was evaporated and the residue was partitioned between methylene chloride and a saturated aqueous sodium bicarbonate solution. The organic phase was washed with water and with brine, dried over magnesium sulphate and evaporated. The material so obtained was triturated under a 6M solution of hydrogen chloride in diethyl ether. There was thus obtained the title compound (0.205 g); NMR Spectrum: (DMSOd$_6$ and CF$_3$CO$_2$D) 2.35 (m, 2H), 3.2–3.9 (m, 10H), 4.0 (s, 3H), 4.35 (m, 2H), 6.12 (s, 2H), 7.0 (s, 1H), 7.1 (s, 1H), 7.38 (s, 1H), 8.15 (s, 1H), 8.85 (s, 1H); Mass Spectrum: M+H⁺ 472 and 474

EXAMPLE 12

4-(6-chloro-2,3-methylenedioxyanilino)-7-[3-(4-cyanomethylpiperazin-1-yl)propoxy]-6-methoxyquinazoline A mixture of 4-(6-chloro-2,3-methylenedioxyanilino)-6-methoxy-7-(3-piperazin-1-ylpropoxy)quinazoline (0.19 g), 2-chloroacetonitrile (0.038 ml), potassium iodide (0.020 g), potassium carbonate (0.139 g) and DMF (2.5 ml) was stirred at ambient temperature for 16 hours. The reaction mixture was partitioned between ethyl acetate and water. The organic phase was washed with water and with brine, dried over magnesium sulphate and evaporated. The crude product was purified by column chromatography on silica using a 93:7 mixture of methylene chloride and methanol as eluent. There was thus obtained the title compound (0.13 g) as a solid; NMR Spectrum: (DMSOd$_6$ and CF$_3$CO$_2$D) 2.3 (m, 2H), 2.6 (m, 2H), 3.05 (m, 2H), 3.15 (m, 2H), 3.35 (m, 2H), 3.65 (m, 2H), 3.9 (s, 2H), 4.05 (s, 3H), 4.35 (m, 2H), 6.15 (s, 2H), 7.05 (d, 1H), 7.15 (d, 1H), 7.4 (s, 1H), 8.15 (s, 1H), 8.9 (s, 1H); Mass Spectrum: [M–H]$^-$ 509 and 511; Elemental Analysis: Found C, 58.41; H, 5.62; N, 15.93. C$_{25}$H$_{27}$ClN$_6$O$_4$.0.2H$_2$O requires C, 58.35; H. 5.37; N, 16.33%.

EXAMPLE 13

6-methoxy-4-(2,3-methylenedioxyanilino)-7-(3-piperazin-1-ylpropoxy)quinazoline dihydrochloride salt Using an analogous procedure to that described in Example 11, 7-[3-(tert-butoxycarbonylpiperazin-1-yl)propoxy]-6-methoxy-4-(2,3-methylenedioxyanilino)quinazoline was reacted with trifluoroacetic acid to give the title compound; NMR Spectrum: (DMSOd$_6$ and CF$_3$CO$_2$D) 2.3–2.4 (m, 2H), 3.2–3.95 (m, 10H), 4.05 (s, 3H), 4.38 (m, 2H), 6.1 (s, 2H), 7.0 (s, 3H), 7.4 (s, 1H), 8.2 (s, 1H), 8.9 (s, 1H); Mass Spectrum: M+H$^+$ 438.

EXAMPLE 14

7-[3-(4-cyanomethylpiperazin-1-yl)propoxy]-6-methoxy-4-(2,3-methylenedioxyanilino)quinazoline Using an analogous procedure to that described in Example 12, 6-methoxy-4-(2,3-methylenedioxyanilino)-7-(3-piperazin-1-ylpropoxy)quinazoline was reacted with 2-chloroacetonitrile to give the title compound as a solid; NMR Spectrum: (DMSOd$_6$) 2.1 (m, 2H), 2.45–2.7 (m, 1H), 3.5 (s, 2H), 4.0 (s, 3H), 4.25 (t, 2H), 6.0 (s, 2H), 6.7 (d, 1H), 6.9 (t, 1H), 7.0 (m, 21), 7.75 (d, 1H), 8.7 (s, 1H); Mass Spectrum: M+H$^+$ 477.

EXAMPLE 15

4-(6-bromo-2,3-methylenedioxyanilino)-6-methoxy-7-(3-piperidinopropoxy)quinazoline Sodium hexamethyldisilazane (1M solution in THF; 0.626 ml) was added to a solution of 6-bromo-2,3-methylenedioxyaniline (0.135 g) in DMF (2 ml) and the mixture was stirred at ambient temperature for 30 minutes. A solution of 4-chloro-6-methoxy-7-(3-piperidinopropoxy)quinazoline (0.1 g) in DMF (3.5 ml) was added and the resultant mixture was stirred at ambient temperature for 3 hours. The reaction mixture was diluted with water and extracted with ethyl acetate (2×). The organic phase was washed with water and with brine, dried over magnesium sulphate and evaporated. The residue was purified by column chromatography on silica using an 80:17:3 mixture of methylene chloride, methanol and a saturated methanolic ammonia solution as eluent. There was thus obtained the title compound as a solid (0.045 g); NMR Spectrum: (DMSOd$_6$ and CF$_3$CO$_2$D) 1.4 (m, 1H), 1.7 (m, 3H), 1.85 (m, 2H]), 2.3 (m, 2H), 2.95 (m, 2H), 3.25 (m, 2H), 3.55 (m, 2H), 4.05 (s, 3H), 4.3 (m, 2H), 6.15 (s, 2H), 7.05 (d, 1H), 7.3 (d, 1H), 7.4 (s, 1H), 8.15 (s, 1H), 8.9 (s, 1H); Mass Spectrum: M+H$^+$ 515 and 517; Elemental Analysis: Found C, 55.74; H, 5.30; N, 10.76. C$_{24}$H$_{27}$BrN$_4$O$_4$ requires C, 55.93; H, 5.28; N, 10.87%.

EXAMPLE 16

4-(6-bromo-2,3-methylenedioxyamino)-6-methoxy-7-[3-(4-methylpiperazin-1-yl)propoxy]quinazoline Using an analogous procedure to that described in Example 15, 4-chloro-6-methoxy-7-[3-(4-methylpiperazin-1-yl)propoxy]quinazoline was reacted with 6-bromo-2,3-methylenedioxyaniline to give the title compound as a solid; NMR Spectrum: (DMSOd$_6$ and CF$_3$CO$_2$D) 2.3 (m, 2H), 2.95 (s, 3H), 3.2–3.9 (br s, 8H), 3.4 (m, 2H), 4.0 (s, 3H), 4.35 (m, 2H), 6.15 (s, 2H), 7.05 (d, 1H), 7.3 (d, 1H), 7.4 (s, 1H), 8.15 (s, 1H), 8.9 (s, 1H); Mass Spectrum: M+H$^+$ 530 and 532; Elemental Analysis: Found C, 54.25; H, 5.54; N, 12.8. C$_{24}$H$_{28}$BrN$_5$O$_4$ requires C, 54.35; H, 5.32; N, 13.2%.

EXAMPLE 17

7-[2-(4-hydroxypiperidin-4-yl)ethoxy]-6-methoxy-4-(2,3-methylenedioxyanilino)quinazoline A mixture of 7-[2-(N-tert-butoxycarbonyl-4-hydroxypiperidin-4-yl)ethoxy]-6-methoxy-4-(2,3-methylenedioxyanilino)quinazoline (0.067 g), trifluoro acetic acid (0.5 ml) and methylene chloride (3 ml) was stirred at ambient temperature for 1 hour. The solvent was evaporated and the residue was partitioned between methylene chloride and a saturated aqueous sodium bicarbonate solution. The organic phase was washed with brine, dried over magnesium sulphate and evaporated. There was thus obtained the title compound (0.015 g); NMR Spectrum: (DMSOd$_6$ and CF$_3$CO$_2$D) 1.75 (m, 4H), 2.05 (t, 2H), 3.1 (m, 4H), 4.0 (s, 3H), 4.35 (t, 2H), 6.1 (s, 2H), 6.95 (m, 3H), 7.4 (s, 1H), 8.1 (s, 1H), 8.85 (s, 1H); Mass Spectrum: M+H$^+$ 439.

EXAMPLE 18

7-[2-(4-hydroxy-N-methylpiperidin-4-yl)ethoxy]-6-methoxy-4-(2,3-methylenedioxyanilino)quinazoline A mixture of 7-[2-(4-hydroxypiperidin-4-yl)ethoxy]-6-methoxy-4-(2,3-methylenedioxyanilino)quinazoline (0.065 g), formaldehyde (40% aqueous solution; 0.2 ml) and formic acid (2 ml) was stirred and heated to 100° C. for 1.5 hours. The mixture was basified to pH9.5 by the addition of 2N aqueous sodium hydroxide solution and extracted with ethyl acetate. The organic phase was washed with water and with brine, dried over magnesium sulphate and evaporated. The residue was purified by column chromatography on silica using an 80:17:3 mixture of methylene chloride, methanol and a saturated methanolic ammonia solution as eluent. There was thus obtained the title compound as a solid (0.021 g); NMR Spectrum: (DMSOd$_6$ and CF$_3$CO$_2$D) 1.8 (m, 4H), 2.05 (m, 2H), 2.8 (s, 3H), 3.15 (m, 2H), 3.3 (m, 2H), 4 (s, 3H), 4.35 (m, 2H), 6.05 (s, 2H), 6.95 (m, 3H), 7.4 (s, 1H), 8.1 (s, 1H), 8.85 (s, 1H); Mass Spectrum: M+H$^+$ 453.

EXAMPLE 19

4-(6-chloro-2,3-methylenedioxyanilino)-6-methoxy-7-(piperidin-4-ylmethoxy)quinazoline dihydrochloride salt Using an analogous procedure to that described in Example 11, 7-(N-tert-butoxycarbonylpiperidin-4-ylmethoxy)-4-(6-chloro-2,3-methylenedioxyanilino)-6-methoxyquinazoline was reacted with trifluoroacetic acid. The material so obtained was triturated under a 6M solution of hydrogen chloride in diethyl ether. There was thus obtained the title compound; NMR Spectrum: (DMSOd$_6$) 1.5–1.65 (m, 2H), 2.0 (d, 2H), 2.2 (m, 1H), 2.95 (m, 2H), 3.2–3.4 (m, 2H), 4.02 (s, 3H), 4.12 (d, 2H), 6.15 (s, 2H), 7.05 (d, 1H), 7.15 (d, 1H), 7.42 (s, 1H), 8.22 (s, 1H), 8.8 (s, 1H); Mass Spectrum: M+H$^+$ 443 and 445.

EXAMPLE 20

4-(6-chloro-2,3-methylenedioxyanilino)-7-(N-cyanomethylpiperidin-4-ylmethoxy)-6-methoxyquinazoline Using an analogous procedure to that described in Example 12, 4-(6-chloro-2,3-methylenedioxyanilino)-6-methoxy-7-(piperidin-4-ylmethoxy)quinazoline was reacted with 2-chloroacetonitrile to give the title compound as a solid; NMR Spectrum: (DMSOd$_6$) 1.65 (m, 2H), 2.1 (m, 2H), 2.2 (m, 1H), 3.15 (m, 2H), 3.6 (m, 2H), 4.05 (s, 3H), 4.15 (m, 2H), 4.55 (s, 2H), 6.15 (s, 2H), 7.05 (d, 1H), 7.15 (d, 1H), 7.4 (s, 1H), 8.15 (s, 1H), 8.9 (s, 1H); Mass Spectrum: M–H$^-$ 480 and 482.

EXAMPLE 21

7-(2-hydroxy-3-morpholinopropoxy)-6-methoxy-4-(2,3-methylenedioxyanilino)quinazoline dihydrochloride salt A mixture of 7-(2-acetoxy-3-morpholinopropoxy)-6-methoxy-4-(2,3-methylenedioxyanilino)quinazoline dihydrochloride (0.104 g) and a saturated methanolic ammonia solution (3 ml) was stirred at ambient temperature for 16 hours. The mixture was evaporated and the residue was purified by column chromatography on silica (Isolute ammonia-treated silica from International Sorbent Technology Limited, catalogue reference 9470-0100) using a 19:1 mixture of methylene chloride and methanol as eluent. The material so obtained was dissolved in methylene chloride (3 ml) and a 6M solution of hydrogen chloride in isopropanol (0.3 ml) was added with stirring. Diethyl ether (10 ml) was added and the resultant precipitate was isolated, washed with diethyl ether and dried under vacuum. There was thus obtained the title compound (0.095 g); NMR Spectrum: (DMSOd$_6$ and CF$_3$CO$_2$D) 3.15–3.45 (m, 4H), 3.54 (d, 2H), 3.743.91 (d, 2H), 3.97 (d, 2H), 4.02 (s, 3H), 4.24 (d, 2H), 4.49–4.58 (m, 1H), 6.08 (s, 2H), 6.96–7.04 (m, 3H), 7.47 (s, 1H), 8.23 (s, 1H), 8.88 (s, 1H); Mass Spectrum: M+H$^+$ 455.

EXAMPLE 22

Using an analogous procedure to that described in Example 21, the appropriate 7-(2-acetoxypropoxy)quinazoline was cleaved to give the compounds described in Table IV. Unless otherwise stated, each compound described in Table IV was obtained as a dihydrochloride salt.

TABLE IV

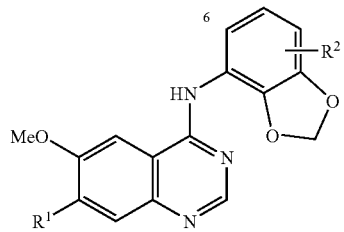

| Compound No. & Note | R$^1$ | R$^2$ |
|---|---|---|
| [1] | 2-hydroxy-3-pyrrolidin-1-ylpropoxy | hydrogen |
| [2] | 2-hydroxy-3-piperidinopropoxy | hydrogen |
| [3] | 3-(4-cyanomethylpiperazin-1-yl)-2-hydroxypropoxy | hydrogen |
| [4] | 2-hydroxy-3-(N-isopropyl-N-methylamino)propoxy | hydrogen |

Notes

[1] The product gave the following characterising data; NMR Spectrum: (DMSOd$_6$ and CF$_3$CO$_2$D) 1.85–1.98(m, 2H), 1.99–2.1(m, 2H), 3.07–3.2(m, 2H), 3.33–3.42(m, 2H), 3.57–3.68(m, 2H), 4.02(s, 3H), 4.22(d, 2H), 4.34–4.43(m, 1H), 6.08(s, 2H), 6.94–7.04(m, 3H), 7.45(s, 1H), 8.22(s, 1H), 8.87(s, 1H); Mass Spectrum: M + H$^+$ 439.

[2] The product gave the following characterising data; NMR Spectrum: (DMSOd$_6$ and CF$_3$CO$_2$D) 1.36–1.51(m, 1H), 1.65–1.78(m, 2H), 1.79–1.92 (m, 3H), 2.93–3.11(m, 2H), 3.2–3.74(m, 2H), 3.54(t, 2H), 4.02(s, 3H), 4.24(d, 2H), 4.46–4.54(m, 1H), 6.08(s, 2H), 6.95–7.03(m, 3H), 7.44(s, 1H), 8.2(s, 1H), 8.88(s, 1H); Mass Spectrum: M + H$^+$ 453.

[3] The product gave the following characterising data; NMR Spectrum: (DMSOd$_6$ and CF$_3$CO$_2$D) 2.54–3.12(m, 4H), 3.13–3.48(m, 3H), 3.55–3.73 (m, 2H), 3.89(s, 3H), 4.03(s, 3H), 4.22–4.3(m, 2H), 4.46–4.59(m, 1H), 6.08(s, 2H), 7.95–7.03(m, 3H), 7.49(s, 1H), 8.27(s, 1H), 8.87(s, 1H); Mass Spectrum: M + H$^+$ 493.

[4] The product gave the following characterising data; NMR Spectrum: (DMSOd$_6$ and CF$_3$CO$_2$D) 1.2–1.36(m, 6H), 2.78(d, 3H), 3.04–3.71(m, 3H), 4.03(s, 3H), 4.24(d, 2H), 4.41–4.55(m, 1H), 6.05(s, 2H), 5.88–6.06 (m, 3H), 7.48(d, 1H), 8.36(s, 1H), 8.82(s, 1H), 9.5–10.1(m, 1H), 11.65(s, 1H); Mass Spectrum: M + H$^+$ 441.

EXAMPLE 23

7-[(2R)-2-hydroxy-3-pyrrolidin-1-ylpropoxy]-6-methoxy-4-(2,3-methylenedioxyanilino)quinazoline dihydrochloride salt A mixture of pyrrolidine (0.016 ml), 7-[(2R)-2,3-ethoxypropoxy]-6-methoxy-4-(2,3-methylenedioxyanilino) quinazoline (0.03 g), chloroform (0.5 ml) and ethanol (0.5 ml) was stirred and heated to 40° C. for 7 hours. The mixture was evaporated and the residue was dissolved in methylene chloride (4 ml). A polystyrene isocyanate resin (prepared according to J. Amer. Chem. Soc., 1997, 119, 4882; loading: 1 mmol/g; 0.3 g) was added and the mixture was shaken at ambient temperature for 1.5 hours. The resin was removed by filtration and washed with methylene chloride. The filtrate was evaporated and the crude product so

TABLE V

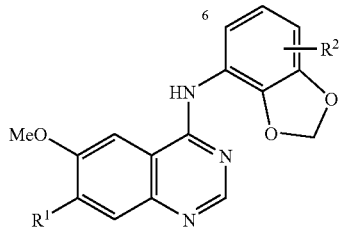

Compound No. & Note | R¹ | R²
---|---|---
[1] | (2R)-2-hydroxy-3-piperidinopropoxy | hydrogen
[2] | (2R)-3-homopiperidin-1-yl-2-hydroxypropoxy | hydrogen
[3] | (2R)-2-hydroxy-3-(N-isopropyl-N-methylamino)propoxy | hydrogen
[4] | (2R)-2-hydroxy-3-(N-isobutyl-N-methylamino)propoxy | hydrogen
[5] | 3-[(2S)-2-(N,N-dimethylcarbamoyl)pyrrolidin-1-yl]-(2R)-2-hydroxypropoxy | hydrogen
[6] | (2R)-3-(N-allyl-N-cyclopentylamino)-2-hydroxypropoxy | hydrogen
[7] | (2R)-3-(N-allyl-N-methylamino)-2-hydroxypropoxy | hydrogen
[8] | (2R)-2-hydroxy-3-pyrrolidin-1-ylpropoxy | 6-chloro
[9] | (2R)-2-hydroxy-3-piperidinopropoxy | 6-chloro
[10] | (2R)-3-homopiperidin-1-yl-2-hydroxypropoxy | 6-chloro
[11] | (2R)-2-hydroxy-3-(N-isopropyl-N-methylamino)propoxy | 6-chloro
[12] | (2R)-2-hydroxy-3-(N-isobutyl-N-methylamino)propoxy | 6-chloro
[13] | 3-[(2S)-2-(N,N-dimethylcarbamoyl)pyrrolidin-1-yl]-(2R)-2-hydroxypropoxy | 6-chloro
[14] | (2R)-3-(N-allyl-N-methylamino)-2-hydroxypropoxy | 6-chloro Notes

[1] The product gave the following characterising data; NMR Spectrum: (DMSOd$_6$ and CF$_3$CO$_2$D) 1.35–1.5(m, 1H), 1.65–1.94(m, 5H), 2.93–3.13 (m, 2H), 3.2–3.4(m, 2H), 3.49–3.61(m, 2H), 4.03(s, 3H), 4.24(d, 2H), 4.47–4.57(m, 1H), 6.08(s, 2H), 6.94–7.05(m, 3H), 7.47(s, 1H), 8.24(s, 1H), 8.88(s, 1H); Mass Spectrum: M−H⁻ 451.

[2] The product gave the following characterising data; NMR Spectrum: (DMSOd$_6$ and CF$_3$CO$_2$D) 1.55–1.75(m, 4H), 1.76–1.96(m, 4H), 3.2–3.34 (m, 3H), 3.38–3.57(m, 3H), 4.03(s, 3H), 4.24(d, 2H), 4.42–4.52(m, 1H), 6.09(s, 2H), 6.94–7.04(m, 3H), 7.45(s, 1H), 8.21(s, 1H), 8.88(s, 1H); Mass Spectrum: M + H⁺ 467.

[3] The product gave the following characterising data; NMR Spectrum: (DMSOd$_6$ and CF$_3$CO$_2$D) 1.21–1.39(m, 6H), 2.81(s, 3H), 3.08–3.77(m, 3H), 4.02(s, 3H), 4.26(d, 2H), 4.39–4.53(m, 1H), 6.08(s, 2H), 6.92–7.05 (m, 3H), 7.46(s, 1H), 8.22(s, 1H), 8.83(s, 1H); Mass Spectrum: M − H⁻ 439.

[4] The product gave the following characterising data; NMR Spectrum: (DMSOd$_6$ and CF$_3$CO$_2$D) 0.91–1.1(m, 6H), 2.05–2.22(s, 1H), 2.91(br s, 3H), 2.92–3.04(m, 1H), 3.08–3.48(m, 3H), 4.03(s, 3H), 4.17–4.34(m, 2H), 4.45–4.59(m, 1H), 6.08(s, 2H), 6.92–7.06(m, 3H), 7.49(s, 1H), 8.28(br s, 1H), 8.87(s, 1H); Mass Spectrum: M + H⁺ 455.

[5] The amine starting material was N,N-dimethyl-L-prolinamide. The product gave the following characterising data; NMR Spectrum: (DMSOd$_6$ and CF$_3$CO$_2$D) 1.78–2.0(m, 2H), 2.09–2.2(m, 1H), 2.52–2.63(m, 1H), 2.95 (s, 3H), 3.02(m, 3H), 3.23–3.36(m, 2H), 3.51(m, 1H), 3.86–3.96(m, 1H), 4.03(s, 3H), 4.16–4.3(m, 2H), 4.39–4.48(m, 1H), 4.85(m, 1H), 6.09(s, 2H), 6.93–7.06(m, 3H), 7.44(s, 1H), 8.23(s, 1H), 8.88(s, 1H); Mass Spectrum: M + H⁺ 510.

[6] The product gave the following characterising data; NMR Spectrum: (DMSOd$_6$ and CF$_3$CO$_2$D) 1.5–2.16(m, 8H), 3.25–3.44(m, 2H), 3.65–4.02 (m, 2H), 3.92(d, 1H), 4.03(s, 3H), 4.19–4.33(m, 2H), 4.42–4.57(m, 1H), 5.55–5.73(m, 2H), 6.02–6.17(m, 3H), 6.96–7.03(m, 3H), 7.41(s, 1H), 8.18 (s, 1H), 8.89(s, 1H); Mass Spectrum: M + H⁺ 493.

[7] The product gave the following characterising data; NMR Spectrum: (DMSOd$_6$ and CF$_3$CO$_2$D) 2.86(br s, 3H), 3.19–3.46(m, 2H), 3.76–3.98(m, 2H), 4.03(s, 3H), 4.25(d, 2H), 4.42–4.53(m, 1H), 5.52–5.65(m, 2H), 5.94–6.06(m, 1H), 6.08(s, 2H), 6.94–7.05(m, 3H), 7.43(br s, 1H), 8.18(s, 1H), 8.89(s, 1H); Mass Spectrum: M − H⁻ 437.

[8] The product gave the following characterising data; NMR Spectrum: (DMSOd$_6$ and CF$_3$CO$_2$D) 1.8–1.99(m, 2H), 2.0–2.11(m, 2H), 3.08–3.22 (m, 2H), 3.33–3.46(m, 2H), 3.59–3.71(m, 2H), 4.03(s, 3H), 4.25(d, 2H), 4.36–4.45(m, 1H), 6.16(d, 1H), 7.07(d, 1H), 7.16(d, 1H), 7.49(s, 1H), 8.24 (s, 1H), 8.91(s, 1H); Mass Spectrum: M − H⁻ 471 and 473.

The 4-(6-chloro-2,3-methylenedioxyanilino)-7-[(2R)-2,3-epoxypropoxy]-6-methoxyquinazoline used as a starting material was prepared by the reaction of 4-(6-chloro-2,3-methylenedioxyanilino)-7-hydroxy-6-methoxyquinazoline and (2R)-(−)-glycidyl tosylate using an analogous procedure to that described in the portion of Example 23 that is concerned with the preparation of starting materials. The material so obtained gave the following characterising data; NMR Spectrum: (DMSOd$_6$ and CF$_3$CO$_2$D) 2.85 (m, 1H), 2.95(t, 1H), 3.45(m, 1H), 4.05(s, 3H), 4.65(m, 1H), 6.15(s, 2H), 7.05(d, 1H), 7.15(d, 1H), 7.35(s, 1H), 8.15(s, 1H), 8.9(s, 1H); Mass Spectrum: M − H⁻ 400 and 402.

[9] The product gave the following characterising data; NMR Spectrum: (DMSOd$_6$ and CF$_3$CO$_2$D) 1.31–1.52(m, 1H), 1.65–1.97(m, 5H), 2.9–3.13 (m, 2H), 3.19–3.42(m, 2H), 3.47–3.61(m, 2H), 4.03(s, 3H), 4.26(d, 2H), 4.45–4.59(m, 1H), 6.16(s, 2H), 7.07(d, 1H), 7.16(d, 1H), 7.49(s, 1H), 8.24 (s, 1H), 8.91(s, 1H); Mass Spectrum: M − H⁻ 485 and 487.

[10] The product gave the following characterising data; NMR Spectrum: (DMSOd$_6$ and CF$_3$CO$_2$D) 1.52–1.76(m, 4H), 1.77–2.02(m, 4H), 3.15–3.34 (m, 3H), 3.36–3.59(m, 3H), 4.03(s, 3H), 4.26(d, 2H), 4.42–4.57(m, 1H), 6.52(s, 2H), 7.06(d, 1H), 7.16(d, 1H), 7.53(s, 1H), 8.29(s, 1H), 8.9(s, 1H); Mass Spectrum: M − H⁻ 499 and 501.

[11] The product gave the following characterising data; NMR Spectrum: (DMSOd$_6$ and CF$_3$CO$_2$D) 1.2–1.4(m, 6H), 2.81(s, 3H), 3.07–3.74(m, 3H), 4.04(s, 3H), 4.27(d, 2H), 4.4–4.54(m, 1H), 6.16(m, 2H), 7.07(d, 1H), 7.15 (d, 1H), 7.51(br s, 1H), 8.28(br s, 1H), 8.9(s, 1H); Mass Spectrum: M − H⁻ 473 and 475.

[12] The product gave the following characterising data; NMR Spectrum: (DMSOd$_6$ and CF$_3$CO$_2$D) 0.91–1.13(m, 6H), 2.06–2.22(m, 1H), 2.91(s, 3H), 2.92–3.04(m, 1H), 3.06–3.47(m, 3H), 4.04(s, 3H), 4.26(d, 2H), 4.44–4.61(m, 1H), 6.16(s, 2H), 7.07(d, 1H), 7.16(d, 1H), 7.51(s, 1H), 8.28 (s, 1H), 8.9(s, 1H); Mass Spectrum: M − H⁻ 487 and 489.

[13] The product gave the following characterising data; NMR Spectrum: (DMSOd$_6$ and CF$_3$CO$_2$D) 1.77–2.01(m, 2H), 2.08–2.22(m, 1H), 2.53–2.63 (m, 1H), 2.95(s, 3H), 3.01(s, 3H), 3.22–3.56(m, 2H), 3.51(m, 1H), 3.85–3.96(m, 1H), 4.03(s, 3H), 4.17–4.3(m, 2H), 4.39–4.49(m, 1H), 4.84(t, 1H), 6.16(s, 2H), 7.07(d, 1H), 7.16(d, 1H), 7.45(s, 1H), 8.22(s, 1H), 8.91 (s, 1H); Mass Spectrum: M − H⁻ 542 and 544.

[14] The product gave the following characterising data; NMR Spectrum: (DMSOd$_6$ and CF$_3$CO$_2$D) 2.83(br s, 3H), 3.16–3.44(m, 2H), 3.73–4.0(m, 2H), 4.03(s, 3H), 4.26(d, 2H), 4.42–4.55(m, 1H), 5.51–5.64(m, 2H), 5.91–6.02(m, 1H), 6.16(s, 2H), 7.07(d, 1H), 7.16(d, 1H), 7.50(br s, 1H), 8.27(br s, 1H), 8.9(s, 1H); Mass Spectrum: M − H⁻ 471 and 473.

EXAMPLE 25

4-(2,2-difluoro-1,3-benzodioxol-4-ylamino)-6-methoxy-7-(3-morpholinopropoxy)quinazoline dihydrochloride salt Using an analogous procedure to that described in Example 1, except that isopropanol was used in place of pentan-2-ol as the reaction solvent and the reaction mixture was heated to 80° C. for 3.5 hours, 4-chloro-6-methoxy-7-(3-morpholinopropoxy)quinazoline (0.15 g) was reacted with 2,2-difluoro-1,3-benzodioxol-4-ylamine (0.092 g). The precipitate so obtained was purified by column chromatography on silica using a 19:1 mixture of methylene chloride and a saturated methanolic ammonia solution as eluent. The material so obtained was dissolved in methylene chloride and a 6M solution of hydrogen chloride in diethyl ether was added. The dihydrochloride salt so obtained was isolated and dried to give the title compound (0.045 g); NMR Spectrum: (DMSOd$_6$ and CF$_3$CO$_2$D) 2.35 (m, 2H), 3.15 (m, 2H), 3.35 (m, 2H), 3.55 (d, 2H), 3.8 (t, 2H), 3.9 (m, 2H), 4.0 (s, 3H), 4.35 (t, 2H), 7.35 (m, 2H), 7.45 (m, 2H), 8.3 (s, 1H), 8.95 (s, 1H); Mass Spectrum: M+H⁺ 475.

EXAMPLE 26

6-methoxy-7-[2-(5-methyl-2-morpholinomethylimidazol-1-yl)ethoxy]-4-(2,3-methylenedioxyanilino)quinazoline Di-tert-butyl azodicarboxylate (0.063 g) was added dropwise to a stirred mixture of 7-hydroxy-6-methoxy-4-(2,3-methylenedioxyanilino)quinazoline (0.055 g), 1-(2-hydroxyethyl)-5-methyl-2-morpholinomethylimidazole (0.046 g), triphenylphosphine (0.072 g) and methylene chloride (1 ml). The reaction mixture was stirred at ambient temperature for 2 hours. The resultant precipitate was isolated, washed with methylene chloride and dried under vacuum to give the title compound (0.052 g); NMR Spectrum: (DMSOd$_6$ and CF$_3$CO$_2$D) 2.55 (s, 3H), 3.1 (br s, 4H), 3.8 (br s, 4H), 4.05 (s, 3H), 4.6 (s, 2H), 4.9 (m, 2H), 6.1 (s, 2H), 7.0 (m, 3H), 7.3 (s, 1H), 7.6 (s, 1H), 8.12 (s, 1H), 8.9 (s, 1H); Mass Spectrum: M+H$^+$ 519.

The 1-(2-hydroxyethyl)-5-methyl-2-morpholinomethylimidazole used as a starting material was prepared as follows:

A mixture of 4-methyl-1-tritylimidazole (*J. Heterocyclic Chem.*, 1982, 19, 253; 32.5 g), methyl bromoacetate (11.4 ml) and acetone (500 ml) was heated to reflux for 2 hours. The solvent was removed by evaporation and the residue was dissolved in methanol (100 ml) and heated to reflux for 45 minutes. The mixture was evaporated and the residue was triturated under diethyl ether. The resultant precipitate was isolated and stirred at ambient temperature for 1 hour in a mixture of diethyl ether (200 ml) and a saturated methanolic ammonia solution (20 ml). The mixture was filtered and the filtrate was evaporated. The residue was purified by column chromatography on silica using a 49:1 mixture of methylene chloride and methanol as eluent. There was thus obtained methyl 2-(5-methylimidazol-1-yl)acetate (6 g); NMR Spectrum: (CDCl$_3$) 2.16 (s, 3H), 3.78 (s, 3H), 4.61 (s, 3H), 6.8 (s, 1H), 7.42 (s, 1H).

A solution of a portion (1.7 g) of the material so obtained in diethyl ether (20 ml) was added dropwise to a stirred suspension of lithium aluminium hydride (0.76 g) in diethyl ether (70 ml) which was cooled to 0° C. The resultant mixture was stirred at ambient temperature for 1 hour. The mixture was cooled to 0° C. and a 6N aqueous sodium hydroxide solution (0.8 ml) and water (2.4 ml) were added dropwise in turn. The mixture was stirred at ambient temperature for 30 minutes and then evaporated. The residue was dissolved in methylene chloride, dried over magnesium sulphate and evaporated to give 1-(2-hydroxyethyl)-5-methylimidazole (1.1 g); NMR Spectrum: (CDCl$_3$) 2.17 (s, 3H), 3.81 (t, 2H), 3.92 (t, 2H), 6.6 (s, 1H), 7.24 (s, 1H).

Tert-butyldimethylsilyl chloride (9.05 g) was added to a stirred mixture of 1-(2-hydroxyethyl)-5-methylimidazole (6.4 g), imidazole (7.5 g) and methylene chloride (30 ml) which was cooled to 0° C. The reaction mixture was stirred at ambient temperature for 4 hours. The mixture was poured into water. The organic layer was washed with brine, dried over magnesium sulphate and evaporated to give 1-(2-tert-butyldimethylsilyloxyethyl)-5-methylimidazole (11.7 g); NMR Spectrum: (CDCl$_3$) −0.04 (s, 6H), 0.85 (s, 6H), 2.2 (s, 3H), 3.8 (m, 2H), 3.94 (m, 2H), 6.75 (s, 1H), 7.43 (s, 1H).

The material so obtained was dissolved in THF (400 ml) and the solution was cooled at −60° C. n-Butyllithium (2.5M in hexane, 40 ml) was added dropwise and the mixture was stirred at −50° C. for 1 hour. The mixture was cooled to −60° C. and DMF (12.5 ml) was added dropwise. The resultant mixture was allowed to warm to ambient temperature and was stirred for 2 hours. Diethyl ether (500 ml) was added and the reaction mixture was poured into a saturated aqueous ammonium chloride solution. The organic layer was separated, washed with brine, dried over magnesium sulphate and evaporated. The material so obtained was purified by column chromatography on silica using increasingly polar mixtures of methylene chloride and a saturated methanolic ammonia solution as eluent. There was thus obtained 1-(2-tert-butyldimethylsilyloxyethyl)-2-formyl-5-methylimidazole (11 g); NMR Spectrum: (CDCl$_3$) −0.1 (s, 6H), 0.79 (s, 9H), 2.32 (s, 3H), 3.91 (t, 2H), 4.4 (t, 2H), 7.07 (s, 1H), 9.71 (s, 1H).

A portion (0.79 g) of the material so obtained was dissolved in methylene chloride (24 ml) and morpholine (0.263 ml) and acetic acid (0.175 ml) were added. Sodium borohydride triacetate (0.8 g) was added portionwise and the mixture was stirred at ambient temperature for 16 hours. The mixture was evaporated and the residue was purified by column chromatography on silica using a 49:1 mixture of methylene chloride and a saturated methanolic ammonia solution as eluent. There was thus obtained 1-(2-tert-butyldimethylsilyloxyethyl)-5-methyl-2-morpholinomethylimidazole (0.5 g); NMR Spectrum: (CDCl$_3$) 0 (s, 6H), 0.82 (s, 9H), 2.25 (s, 3H), 2.45 (m, 4H), 3.6 (s, 2H), 3.68 (m, 4H), 3.85 (t, 2H), 4.1 (t, 2H), 6.7 (s, 1H).

A mixture of the material so obtained, 12N aqueous hydrochloric acid (0.26 ml) and methanol (10 ml) was stirred at ambient temperature for 5 hours. The mixture was evaporated and the residue was triturated under pentane. The resultant solid was isolated and dried under vacuum. The solid was stirred at ambient temperature for 1 hour in a mixture of methylene chloride and a saturated methanolic ammonia solution. The mixture was filtered and the filtrate was evaporated. The residue was purified by column chromatography on silica using a 19:1 mixture of methylene chloride and a saturated methanolic ammonia solution as eluent. There was thus obtained 1-(2-hydroxyethyl)-5-methyl-2-morpholinomethylimidazole (0.25 g); NMR Spectrum: (CDCl$_3$) 2.2 (s, 3H), 2.6 (br s, 4H), 3.58 (s, 2H), 3.7 (m, 4H), 3.85 (t, 2H), 4.1 (t, 2H), 6.5–6.9 (br s, 1H), 6.65 (s, 1H).

EXAMPLE 27

Unless otherwise stated, each compound described in Table VI was obtained as a dihydrochloride salt.

TABLE VI

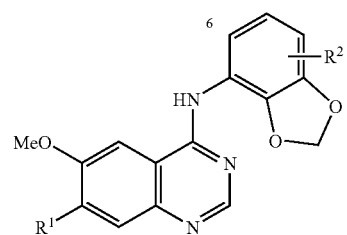

| No. & Note | R$^1$ | R$^2$ |
|---|---|---|
| [1] | 2-[2-(N,N-dimethylcarbamoyl)pyrrolidin-1-yl]ethoxy | hydrogen |
| [2] | 2-[2-(N-methylcarbamoyl)pyrrolidin-1-yl]ethoxy | hydrogen |
| [3] | 2-(2-carbamoylpyrrolidin-1-yl)ethoxy | hydrogen |

TABLE VI-continued

| [4]  | 2-(2-piperidinocarbonylpyrrolidin-1-yl)ethoxy | hydrogen |
| [5]  | 2-(2-morpholinocarbonylpyrrolidin-1-yl)ethoxy | hydrogen |
| [6]  | 2-[2-(4-methylpiperazin-1-ylcarbonyl)pyrrolidin-1-yl]ethoxy | hydrogen |
| [7]  | 2-[2-(pyrrolidin-1-ylcarbonyl)pyrrolidin-1-yl]ethoxy | hydrogen |
| [8]  | 2-(2-methylpyrrolidin-1-yl)ethoxy | hydrogen |
| [9]  | 2-(2-methoxymethylpyrrolidin-1-yl)ethoxy | hydrogen |
| [10] | 3-pyridylmethoxy | hydrogen |
| [11] | 4-pyridylmethoxy | hydrogen |

Notes

[1] The free base was obtained from the chromatographic purification and gave the following data; NMR Spectrum: (DMSOd$_6$ and CF$_3$CO$_2$D) 1.8–1.95(m, 3H), 2.05–2.2(m, 1H), 2.7(s, 3H), 3.0(s, 3H), 3.35(m, 1H), 3.8–3.9(m, 2H), 4.02(s, 3H), 4.5(m, 2H), 4.8(m, 2H), 6.06(s, 2H), 6.96(s, 3H), 7.35(s, 1H), 8.15(s, 1H), 8.9(s, 1H); Mass Spectrum: M + H$^+$ 480.
The (2S)-1-(2-hydroxyethyl)-N,N-dimethylpyrrolidine-2-carboxamide used as a starting material was prepared as follows:-
A mixture of 1-(tert-butoxycarbonyl)-L-proline (10.75 g), 1-(3-dimethylaminopropyl)-3-ethylcarbodiimide hydrochloride (10.6 g), dimethylamine hydrochloride (5.33 g), 4-dimethylaminopyridine (6.1 g) and methylene chloride (200 ml) was stirred at ambient temperature for 4 hours. The mixture was poured into water. The organic layer was separated, washed in turn with a 1N aqueous potassium hydrogen sulphate solution, with a 5% aqueous sodium bicarbonate solution and brine, dried over magnesium sulphate and evaporated to give 1-(tert-butoxycarbonyl)-N,N-dimethyl-L-prolinamide (11.2 g); NMR Spectrum: (CDCl$_3$) 1.4 and 1.5(2s, 9H), 1.8–1.9(m, 2H), 1.95–2.2(m, 2H), 3.0 and 3.1(2d, 6H), 3.35–3.6(m, 2H), 4.55 and 4.7(2m, 1H).
A mixture of a portion (0.24 g) of the material so obtained and trifluoroacetic acid (3 ml) was stirred at ambient temperature for 2 hours. The mixture was evaporated and the residue was triturated under diethyl ether. A slight excess of a 2M solution of hydrogen chloride in diethyl ether was added and the precipitate was isolated and dried under vacuum to give N,N-dimethyl-L-prolinamide hydrochloride salt (0.25 g); NMR Spectrum: (DMSOd$_6$ and CF$_3$CO$_2$D) 1.7–2.0(m, 3H), 2.3–2.5(m, 1H), 2.95(s, 3H), 3.05(s, 3H), 3.1–3.4(m, 2H), 4.6(m, 1H).
A mixture of N,N-dimethyl-L-prolinamide hydrochloride salt (6.3 g), 2-bromoethanol (3.8 ml), potassium carbonate (14 g) and acetonitrile (70 ml) was stirred and heated to reflux for 16 hours. The mixture was filtered and the filtrate was evaporated. The residue was purified by column chromatography on silica using a 24:1 mixture of methylene chloride and a saturated methanolic ammonia solution as eluent. There was thus obtained (2S)-1-(2-hydroxyethyl)-N,N-dimethylpyrrolidine-2-carboxamide (3.4 g); NMR Spectrum: (CDCl$_3$) 1.6(m, 1H), 1.6–2.0(m, 4H), 2.1–2.3(m, 2H), 2.4(m, 1H), 2.9(m, 1H), 3.0(s, 3H), 3.05(s, 3H), 3.25–3.4(m, 2H), 3.75(m, 1H), 3.9(m, 1H), 5.1(br s, 1H); Mass Spectrum: M + H$^+$ 187.
[2] (2S)-1-(2-Hydroxyethyl)-N-methylprolinamide was used as a starting material. The dihydrochloride salt gave the following data; Mass Spectrum: M + H$^+$ 466.
The (2S)-1-(2-hydroxyethyl)-N-methylprolinamide used as a starting material was obtained as follows:-
A mixture of 1-(tert-butoxycarbonyl)-L-proline (5.4 g), 1-(3-dimethylaminopropyl)-3-ethylcarbodiimide (5.3 g), methylamine hydrochloride (2.2 g), 4-dimethylaminopyridine (3 g) and methylene chloride (50 ml) was stirred at ambient temperature for 16 hours. The resultant mixture was poured in water and the organic layer was separated, washed in turn with a 1 M aqueous potassium hydrogen sulphate solution, a saturated aqueous sodium bicarbonate solution and brine, dried over magnesium sulphate and evaporated. There was thus obtained 1-(tert-butoxycarbonyl)-N-methyl-L-prolinamide (5.6 g); Mass Spectrum: M + H$^+$ 229.
A mixture of a portion (4.4 g) of the material so obtained and trifluoroacetic acid (10 ml) was stirred at ambient temperature for 2 hours. The mixture was evaporated and the residue was triturated under diethyl ether. The resultant solid was isolated, washed with diethyl ether and dried under vacuum. There was thus obtained to give N-methyl-L-prolinamide trifluoroacetic acid salt (3.7 g); NMR Spectrum: (DMSOd$_6$ and CF$_3$CO$_2$D) 1.85–2.05(m, 3H), 2.2–2.3(m, 1H), 2.73(s, 3H), 3.2–3.4(m, 2H), 4.2(m, 1H).

A mixture of a portion (2.5 g) of the material so obtained, 2-bromoethanol (2.15 ml), potassium carbonate (5.5 g) and acetonitrile (20 ml) was stirred and heated to reflux for 18 hours. The mixture was cooled to ambient temperature, filtered and evaporated and the residue was purified by column chromatography on silica using a 49:1 mixture of methylene chloride and a saturated methanolic ammonia solution as eluent. There was thus obtained (2S)-1-(2-hydroxyethyl)-N-methylprolinamide (0.5 g); NMR Spectrum: (CDCl$_3$) 1.6–2.0(m, 4H), 2.1–2.3(m, 1H), 2.3–2.45(m, 1H), 2.6–2.7(m, 1H), 2.85(d, 3H), 2.8–2.9(m, 1H), 3.1–3.2(m, 1H), 3.2–3.3(m, 1H), 3.6–3.8(m, 2H); Mass Spectrum: M + H$^+$ 173.
[3] (2S)-1-(2-Hydroxyethyl)prolinamide was used as a starting material. The dihydrochloride salt gave the following data; NMR Spectrum: (DMSOd$_6$ and CF$_3$CO$_2$D) 1.75–2.02(m, 2H), 2.03–2.19(m, 1H), 2.56–2.67(m, 1H), 3.3–3.43(m, 1H), 3.7–3.91(m, 3H), 4.03(s, 3H), 4.28–4.43(m, 1H), 4.45–4.65(m, 2H), 6.08(s, 2H), 6.94–7.04(m, 3H), 7.42(s, 1H), 8.21(s, 1H), 8.88(s, 1H); Mass Spectrum: M + H$^+$ 452.
The (2S)-1-(2-hydroxyethyl)prolinamide used as a starting material was prepared by the reaction of L-prolinamide and 2-bromoethanol using an analogous procedure to that described in Note [2] immediately above. There was thus obtained the required starting material; NMR Spectrum: (CDCl$_3$) 1.6–2.0(m, 4H), 2.1–2.25(m, 1H), 2.35–2.45(m, 1H), 2.6–2.7(m, 1H), 2.8–3.0(m, 1H), 3.1(m, 1H), 3.2–3.3(m, 1H), 3.6–3.8(m, 2H), 5.6(br s, 1H), 7.4(br s, 1H); Mass Spectrum: M + H$^+$ 159.
[4] (2S)-1-(2-Hydroxyethyl)-2-piperidinocarbonylpyrrolidine was used as a starting material. The dihydrochloride salt gave the following data; NMR Spectrum: (DMSOd$_6$ and CF$_3$CO$_2$D) 1.28–1.75(m, 7H), 1.76–1.99(m, 2H), 2.02–2.25(m, 1H), 3.02–3.19(m, 1H), 3.22–3.5(m, 3H), 3.53–3.65(m, 1H), 3.68–3.9(m, 3H), 4.04(s, 3H), 4.44–4.63(m, 2H), 4.74–4.89(m, 1H), 6.36 (s, 2H), 6.91–7.07(m, 3H), 7.45(s, 1H), 8.25(s, 1H), 8.89(s, 1H); Mass Spectrum: M + H$^+$ 520.
The (2S)-1-(2-hydroxyethyl)-2-piperidinocarbonylpyrrolidine used as a starting material was prepared as follows:-
Using analogous procedures to those described in Note [2] immediately above, 1-(tert-butoxycarbonyl)-L-proline was reacted with piperidine to give (2S)-1-(tert-butoxycarbonyl)-2-piperidinocarbonylpyrrolidine which was deprotected and reacted with 2-bromoethanol. There was thus obtained the required starting material; NMR Spectrum: (CDCl$_3$) 1.5–1.9 (m, 10H), 1.9–2.0(m, 1H), 2.1–2.2(m, 1H), 2.4–2.5(m, 1H), 2.55–2.65(m, 1H), 2.8–2.9(m, 1H), 3.3–3.7(m, 6H), 4.3(br s, 1H); Mass Spectrum: M + H$^+$ 227.
[5] (2S)-1-(2-Hydroxyethyl)-2-morpholinocarbonylpyrrolidine was used as a starting material. The dihydrochloride salt gave the following data; NMR Spectrum: (DMSOd$_6$ and CF$_3$CO$_2$D) 1.3–1.5(m, 2H), 1.8–2.0(m, 3H), 2.15 (m, 2H), 3.2(m, 1H), 3.3–3.9(m, 8H), 4.05(s, 3H), 4.55(m, 2H), 4.8(m, 1H), 6.1(s, 2H), 7.0(m, 3H), 7.4(s, 1H), 8.2(s, 1H), 8.9(s, 1H); Mass Spectrum: M + H$^+$ 522.
The (2S)-1-(2-hydroxyethyl)-2-morpholinocarbonylpyrrolidine used as a starting material was prepared as follows:-
Using analogous procedures to those described in Note [2] immediately above, 1-(tert-butoxycarbonyl)-L-proline was reacted with morpholine to give (2S)-1-(tert-butoxycarbonyl)-2-morpholinocarbonylpyrrolidine which was deprotected and reacted with 2-bromoethanol. There was thus obtained the required starting material; NMR Spectrum: (CDCl$_3$) 1.7–2.0 (m, 4H), 2.1–2.2(m, 1H), 2.4–2.5(m, 1H), 2.6–2.7(m, 1H), 2.8–2.9(m, 1H), 3.3–3.4(m, 2H), 3.4–3.8(m, 10H); Mass Spectrum: M + H$^+$ 229.
[6] (2S)-1-(2-Hydroxyethyl)-2-(4-methylpiperazin-1-ylcarbonyl)pyrrolidine was used as a starting material. The free base was obtained from the chromatographic purification and gave the following data; NMR Spectrum: (CDCl$_3$) 1.41–1.49(m, 2H), 1.81–1.91(m, 2H), 1.92–2.02(m, 1H), 2.09–2.2 (m, 1H), 2.28(s, 3H), 2.29–2.36(m, 2H), 2.37–2.48(m, 2H), 2.49–2.57(m, 1H), 2.93–3.03(m, 1H), 3.19–3.28(m, 1H), 3.35–3.42(m, 1H), 3.56–3.77 (m, 3H), 4.01(s, 3H), 4.25–4.38(m, 2H), 6.03(s, 2H), 6.4–6.45(m, 1H), 6.69(d, 1H), 6.91(m, 1H), 7.04(s, 1H), 7.24(s, 1H), 7.52(d, 1H); Mass Spectrum: M + H$^+$ 535.
The (2S)-1-(2-hydroxyethyl)-2-(4-methylpiperazin-1-ylcarbonyl)pyrrolidine used as a starting material was prepared as follows:-
Using analogous procedures to those described in Note [2] immediately above, 1-(tert-butoxycarbonyl)-L-proline was reacted with 1-methylpiperazine to give (2S)-1-(tert-butoxycarbonyl)-2-(4-methylpiperazin-1-ylcarbonyl)pyrrolidine which was deprotected and reacted with 2-bromoethanol. There was thus obtained the required starting material; NMR Spectrum: (CDCl$_3$) 1.7–2.05(m, 4H), 2.1–2.25(m, 1H), 2.32(s, 3H), 2.35–2.5(m, 4H), 2.6–2.7(m, 1H), 2.8–2.9(m, 1H), 3.3–3.7(m, 8H), 4.15(br s, 1H); Mass Spectrum: M + H$^+$ 242.
[7] (2S)-1-(2-Hydroxyethyl)-2-(pyrrolidin-1-ylcarbonyl)pyrrolidine was used as a starting material. The dihydrochloride salt gave the following data; NMR Spectrum: (DMSOd$_6$ and CF$_3$CO$_2$D) 1.29–1.52(m, 2H), 1.55–2.03(m, 5H), 2.07–2.23(m, 1H), 2.93–3.08(m, 1H), 3.18–3.45(m, 3H), 3.46–3.59(m, 1H), 3.72–3.93(m, 3H), 4.03(s, 3H), 4.43–4.71(m, 3H), 6.09(s, 2H), 7.94–7.06(m, 3H), 7.39(s, 1H), 8.2(s, 1H), 8.89(s, 1H); Mass Spectrum: M − H$^-$ 504.

TABLE VI-continued

The (2S)-1-(2-hydroxyethyl)-2-(pyrrolidin-1-ylcarbonyl)pyrrolidine used as a starting material was prepared as follows:-

Using analogous procedures to those described in Note [2] immediately above, 1-(tert-butoxycarbonyl)-L-proline was reacted with pyrrolidine to give (2S)-1-(tert-butoxycarbonyl)-2-(pyrrolidin-1-ylcarbonyl)pyrrolidine which was deprotected and reacted with 2-bromoethanol. There was thus obtained the required starting material; NMR Spectrum: (CDCl$_3$) 1.7–2.05 (m, 8H), 2.1–2.3(m, 1H), 2.4–2.5(m, 1H), 2.55–2.7(m, 1H), 2.8–2.9(m, 1H), 3.2–3.3(m, 2H), 3.4–3.7(m, 5H), 4.1(br s, 1H); Mass Spectrum: M + H$^+$ 213.

[8] (2R)-1-(2-Hydroxyethyl)-2-methylpyrrolidine was used as a starting material. The dihydrochloride salt gave the following data; NMR Spectrum: (DMSOd$_6$ and CF$_3$CO$_2$D) 1.45(d, 3H), 1.6–1.7(m, 1H), 1.9–2.1(m, 2H), 2.1–2.3(m, 1H), 3.35(m, 1H), 3.5–3.7(m, 2H), 3.7–3.8(m, 1H), 3.9(m, 1H), 4.05(s, 3H), 4.6(br s, 2H), 6.1(s, 2H), 7.0(s, 3H), 7.45(s, 1H), 8.25(s, 1H), 8.9(s, 1H); Mass Spectrum: M + H$^+$ 423.

The (2R)-1-(2-hydroxyethyl)-2-methylpyrrolidine used as a starting material was obtained as follows:-

A mixture of (2R)-2-methylpyrrolidine (0.853 g), 2-bromoethanol (1.1 ml), potassium carbonate (2.8 g) and acetonitrile (10 ml) was stirred and heated to reflux for 18 hours. The mixture was filtered and the filtrate was evaporated. The resultant residue was purified by column chromatography on silica using a 49:1 mixture of methylene chloride and a saturated methanolic ammonia solution as eluent. There was thus obtained (2R)-1-(2-hydroxyethyl)-2-methylpyrrolidine (0.35 g); NMR Spectrum: (CDCl$_3$) 1.1(d, 3H), 1.3–1.5(m, 1H), 1.6–1.8(m, 3H), 1.95(m, 1H), 2.15(m, 1H), 2.28(m, 1H), 2.4–2.5(m, 1H), 2.95–3.05(m, 1H), 3.2(m, 1H), 3.5–3.8(m, 2H); Mass Spectrum: M + H$^+$ 130.

[9] (2S)-1-(2-Hydroxyethyl)-2-methoxymethylpyrrolidine was used as a starting material. The dihydrochloride salt gave the following data; NMR Spectrum: (DMSOd$_6$ and CF$_3$CO$_2$D) 1.4–1.5(m, 1H), 1.65–1.8(m, 1H), 1.8–2.0(m, 1H), 2.0–2.12(m, 1H), 2.12–2.25(m, 1H), 3.35(s, 3H), 3.7(m, 4H), 3.8–4.0(m, 2H), 4.05(s, 3H), 4.6(m, 2H), 6.1(s, 2H), 7.0(m, 3H), 7.45 (s, 1H), 8.25(s, 1H), 8.9(s, 1H); Mass Spectrum: M + H$^+$ 453.

The (2S)-1-(2-hydroxyethyl)-2-methoxymethylpyrrolidine used as a starting material was obtained as follows:-

Using an analogous procedure to those described in Note [8] immediately above, (2S)-2-methoxymethylpyrrolidine was reacted with 2-bromoethanol to give (2S)-1-(2-hydroxyethyl)-2-methoxymethylpyrrolidine; NMR Spectrum: (CDCl$_3$) 1.5–1.65(m, 1H), 1.65–1.8(m, 2H), 1.8–2.0(m, 2H), 2.3(m, 1H), 2.6(m, 1H), 2.8(m, 1H), 2.95–3.05(m, 1H), 3.17(m, 1H), 3.3(t, 1H), 3.35(t, 1H), 3.37(s, 3H), 3.5–3.7 (m, 2H).

[10] The dihydrochloride salt gave the following data; NMR Spectrum: (DMSOd$_6$ and CF$_3$CO$_2$D) 4.05(s, 3H), 5.6(s, 2H), 6.1(s, 2H), 7.0(s, 3H), 7.6(s, 1H), 8.2(m, 1H), 8.3(s, 1H), 8.8(d, 1H), 8.9(s, 1H), 9.05(d, 1H), 9.2(s, 1H); Mass Spectrum: M + H$^+$ 403.

[11] The dihydrochloride salt gave the following data; NMR Spectrum: (DMSOd$_6$ and CF$_3$CO$_2$D) 4.1(s, 3H), 5.75(s, 2H), 6.1(s, 2H), 7.0(s, 3H), 7.5(s, 1H), 8.2(d, 2H), 8.3(s, 1H), 8.9(s, 1H), 9.05(d, 2H); Mass Spectrum: M + H$^+$ 403.

EXAMPLE 28

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (e) | Injection I | (50 mg/ml) |
|---|---|---|
| | Compound X | 5.0% w/v |
| | 1 M Sodium hydroxide solution | 15.0% v/v |
| | 0.1 M Hydrochloric acid | |
| | (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1M Sodium hydroxide solution | 15.0% v/v |
| | Water for injection to 100% | |

| (g) | Injection III | (1 mg/ml, buffered to pH 6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |

-continued

| | | |
|---|---|---|
| Trichlorofluoromethane | 67.5 | |
| Dichlorodifluoromethane | 1086.0 | |
| Dichlorotetrafluoroethane | 191.6 | |
| (l) Ointment | | ml |
| Compound X | 40 mg | |
| Ethanol | 300 μl | |
| Water | 300 μl | |
| 1-Dodecylazacycloheptan-2-one | 50 μl | |
| Propylene glycol | to 1 ml | |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:

1. A method for the treatment of an autoimmune disease or medical condition selected from transplant rejection and rheumatoid arthritis in a warm-blooded animal in need thereof which comprises administering to said animal an effective amount of a quinazoline derivative of the Formula I

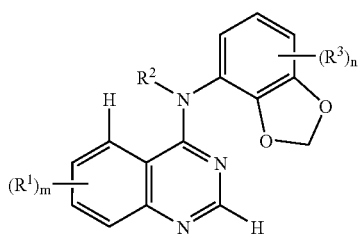

wherein:
m is 2 and
the first $R^1$ group is a 6-methoxy group and
the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino) propoxy, 4-(N-isopropyl-N-methylamino)butoxy, 2-(N-isobutyl-N-methylamino)ethoxy, 3-(N-isobutyl-N-methylamino)propoxy, 4-(N-isobutyl-N-methylamino)butoxy, 2-(N-allyl-N-methylamino)ethoxy, 3-(N-allyl-N-methylamino)propoxy, 4-(N-allyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl) ethoxy, 3-piperidin-4-ylpropoxy, 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl) butoxy, 2-(2-piperazin-1-ylethoxy)ethoxy, 2-[2-(4-methylpiperazin-1-yl)ethoxy]ethoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any $CH_2$ group within the second $R^1$ group that is attached to two carbon atoms optionally bears a hydroxy group on said $CH_2$ group, and wherein any heteroaryl group within the second $R^1$ group optionally bears 1 or 2 substituents selected from chloro, cyano, hydroxy and methyl, and any heterocyclyl group within the second $R^1$ group optionally bears 1 or 2 substituents selected from hydroxy, methyl and oxo;

$R^2$ is hydrogen; and
n is 0 or n is 1 and
the $R^3$ group is located at the 6-position of the 2,3-methylenedioxyphenyl group and is selected from chloro and bromo;

or a pharmaceutically-acceptable acid-addition salt thereof.

2. The method as claimed in claim 1 wherein:
m is 2 and
the first $R^1$ group is a 6-methoxy group and
the second $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl) ethoxy, 3-(1,1-dioxotetrahydro-4H-1,4-thiazin-4-yl) propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl) propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-methylsulphonylethoxy, 3-methylsulphonylpropoxy, 2-(4-pyridyloxy)ethoxy, 3-pyridylmethoxy and 2-cyanopyrid-4-ylmethoxy;

$R^2$ is hydrogen; and
n is 0 or n is 1 and the R³ group is located at the 6-position of the 2,3-methylenedioxyphenyl group and is selected from chloro and bromo;

or a pharmaceutically-acceptable acid-addition salt thereof.

3. The method as claimed in claim 1 wherein:

m is 2 and the first R¹ group is a 6-methoxy group and the second R¹ group is located at the 7-position and is selected from 3-(N-isopropyl-N-methylamino)propoxy, 3-pyrrolidin-1-ylpropoxy, 3-morpholinopropoxy, 3-(1,1-dioxotetrahydro-4H-1,4-thiazin-4-yl)propoxy, 3-piperidinopropoxy, N-methylpiperidin-4-ylmethoxy, 2-(4-methylpiperazin-1-yl)ethoxy, 3-(4-methylpiperazin-1-yl)propoxy, 3-(4-cyanomethylpiperazin-1-yl)propoxy and 2-[2-(4-methylpiperazin-1-yl)ethoxy]ethoxy, and wherein any CH₂ group within the second R¹ group that is attached to two carbon atoms optionally bears a hydroxy group on said CH₂ group;

R² hydrogen; and n is 0;

or a pharmaceutically-acceptable acid-addition salt thereof.

4. The method as claimed in claim 1 wherein the quinazoline derivative of the Formula I selected from:

6-methoxy-4-(2,3-methylenedioxyanilino)-7-(3-morpholinopropoxy)quinazoline, 6-methoxy-4-(2,3-methylenedioxyanilino)-7-[3-(1,1-dioxotetrahydro-4H-1,4-thiazin-4-yl)propoxy]quinazoline, 6-methoxy-4-(2,3-methylenedioxyanilino)-7-(3-pyrrolidin-1-ylpropoxy)quinazoline, 6-methoxy-4-(2,3-methylenedioxyanilino)-7-[2-(4-methylpiperazin-1-yl)ethoxy]quinazoline, 6-methoxy-4-(2,3-methylenedioxyanilino)-7-[3-(4-methylpiperazin-1-yl)propoxy]quinazoline, 6-methoxy-4-(2,3-methylenedioxyanilino)-7-(3-pipendinopropoxy)quinazoline, 6-methoxy-4-(2,3-methylenedioxyanilino)-7-(N-methylpiperidin-4-ylmethoxy)quinazoline, 7-(2-hydroxy-3-pyrrolidin-1-ylpropoxy)-6-methoxy-4-(2,3-methylenedioxyanilino)quinazoline, 7-[2-hydroxy-3-(N-isopropyl-N-methylamino)propoxy]-6-methoxy-4-(2,3-methylenedioxyanilino)quinazoline, 7-[3-(4-cyanomethylpiperazin-1-yl)-2-hydroxypropoxy]-6-methoxy-4-(2,3-methylenedioxyanilino)quinazoline, 6-methoxy-4-(2,3-methylenedioxyanilino)-7-{2-[2-(4-methylpiperazin-1-yl)ethoxy]ethoxy}quinazoline, 4-(6-chloro-2,3-methylenedioxyanilino)-7-[3-(4-cyanomethylpiperazin-1-yl)propoxy]-6-methoxyquinazoline, 4-(6-chloro-2,3-methylenedioxyanilino)-6-methoxy-7-(3-pyrrolidin-1-ylpropoxy)quinazoline, 4-(6-chloro-2,3-methylenedioxyanilino)-6-methoxy-7-(3-piperidinopropoxy)quinazoline, 4-(6-bromo-2,3-methylenedioxyaniiino)-6-methoxy-7-(3-piperidinopropoxy)quinazoline, 6-methoxy-4-(2,3-methylenedioxyanilino)-7-[2-(N-methylpiperidin-4-yl)ethoxy]quinazoline, 6-methoxy-4-(2,3-methylenedioxyanilino)-7-[2-(4-pyridyloxy)ethoxy]quinazoline, 6-methoxy-4-(2,3-methylenedioxyanilino)-7-(3-pyridylmethoxy)quinazoline, 4-(6-chloro-2,3-methylenedioxyanilino)-7-(2-cyanopyrid-4-ylmethoxy)-6-methoxyquinazoline and 4-(6-chloro-2,3-methylenedioxyanilino)-6-methoxy-7-(N-methylpiperidin-4-ylmethoxy)quinazoline;

or a pharmaceutically-acceptable acid-addition salt thereof.

5. The method as claimed in claim 1 wherein the quinazoline derivative of the Formula I selected from:

6-methoxy-4-(2,3-methylenedioxyanilino)-7-(3-pyrrolidin-1-ylpropoxy)quinazoline, 4-(6-chloro-2,3-methylenedioxyanilino)-7-[3-(4-cyanomethylpiperazin-1-yl)propoxy]-6-methoxyquinazoline, 6-methoxy-4-(2,3-methylenedioxyanilino)-7-(N-methylpiperidin-4-ylmethoxy)quinazoline, 6-methoxy-4-(2,3-methylenedioxyanilino)-7-[2-(N-methylpiperidin-4-yl)ethoxy]quinazoline and 7-(2-hydroxy-3-pyrrolidin-1-ylpropoxy)-6-methoxy-4-(2,3-methylenedioxyanilino)quinazoline;

or a pharmaceutically-acceptable acid-addition salt thereof.

6. The method of claim 1 for the treatment of transplant rejection.

7. The method of claim 1 for treating or preventing acute rejection of a transplanted organ.

8. The method of claim 1 for the treatment of rheumatoid arthritis.

* * * * *